United States Patent
Brauns et al.

(10) Patent No.: US 11,718,683 B2
(45) Date of Patent: Aug. 8, 2023

(54) ANTIGEN-BINDING FUSION PROTEINS WITH MODIFIED HSP70 DOMAINS

(71) Applicants: The General Hospital Corporation, Boston, MA (US); Apensys, Inc., Cumming, GA (US)

(72) Inventors: Timothy Brauns, Brookline, MA (US); Mark C. Poznansky, Newton Center, MA (US); Jeffrey A. Gelfand, Cambridge, MA (US); Huabiao Chen, Winchester, MA (US); Stephen J. McCormack, Las Vegas, NV (US)

(73) Assignees: Aperisys, Inc., Cumming, GA (US); The General Hospital Corporation, Boston, MA (US)

( * ) Notice: Subject to any disclaimer, the term of this patent is extended or adjusted under 35 U.S.C. 154(b) by 109 days.

(21) Appl. No.: 16/532,200

(22) Filed: Aug. 5, 2019

(65) Prior Publication Data

US 2020/0095332 A1    Mar. 26, 2020

Related U.S. Application Data

(63) Continuation of application No. 15/456,196, filed on Mar. 10, 2017, now abandoned.

(60) Provisional application No. 62/306,168, filed on Mar. 10, 2016.

(51) Int. Cl.
| | | |
|---|---|---|
| C07K 16/30 | (2006.01) | |
| C07K 14/35 | (2006.01) | |
| C07K 19/00 | (2006.01) | |
| A61K 39/00 | (2006.01) | |
| A61K 38/00 | (2006.01) | |

(52) U.S. Cl.
CPC .......... C07K 16/3069 (2013.01); C07K 14/35 (2013.01); C07K 16/30 (2013.01); A61K 38/00 (2013.01); A61K 2039/505 (2013.01); C07K 19/00 (2013.01); C07K 2317/622 (2013.01); C07K 2317/76 (2013.01); C07K 2319/30 (2013.01); C07K 2319/33 (2013.01); C07K 2319/70 (2013.01); C07K 2319/74 (2013.01)

(58) Field of Classification Search
CPC .............. C07K 14/35; C07K 2317/622; C07K 2319/33; C07K 2319/74; A61K 2039/505
See application file for complete search history.

(56) References Cited

U.S. PATENT DOCUMENTS

| | | | |
|---|---|---|---|
| 4,215,051 A | 7/1980 | Schroeder et al. | |
| 4,554,101 A | 11/1985 | Hopp | |
| 4,816,567 A | 3/1989 | Cabilly et al. | |
| 5,225,539 A | 7/1993 | Winter | |
| 5,951,988 A | 9/1999 | Littel-van den Hurk et al. | |
| 6,734,173 B1 * | 5/2004 | Wu | C07K 14/475 514/44 R |
| 7,749,501 B2 | 7/2010 | Gelfand | |
| 7,932,055 B2 | 4/2011 | Spee et al. | |
| 7,943,133 B2 * | 5/2011 | Gelfand | C07K 14/35 424/134.1 |
| 8,143,387 B2 | 3/2012 | Gelfand | |
| 8,435,494 B2 | 5/2013 | Gelfand | |
| 2002/0146426 A1 * | 10/2002 | Huang | A61P 37/04 424/185.1 |
| 2003/0035807 A1 | 2/2003 | McCormick et al. | |
| 2004/0063173 A1 | 4/2004 | Multhoff et al. | |
| 2005/0079170 A1 | 4/2005 | Le Gall et al. | |
| 2006/0264609 A1 * | 11/2006 | Lehner | C07K 14/47 530/350 |
| 2008/0085539 A1 | 4/2008 | Scholler et al. | |
| 2009/0068184 A1 | 3/2009 | Gelfand | |
| 2009/0155269 A1 | 6/2009 | Gelfand | |
| 2009/0162405 A1 * | 6/2009 | Qian | A61K 39/0011 424/277.1 |
| 2012/0134992 A1 | 5/2012 | Gelfand | |
| 2014/0301993 A1 | 10/2014 | Powell et al. | |

FOREIGN PATENT DOCUMENTS

| | | | |
|---|---|---|---|
| CN | 105481985 A * | 4/2016 | |
| EP | 0125023 | 11/1984 | |
| EP | 0171496 | 2/1986 | |
| EP | 0173494 | 3/1986 | |
| EP | 0184187 | 6/1986 | |
| WO | WO 86/01533 | 3/1986 | |
| WO | WO 87/02671 | 5/1987 | |
| WO | WO 94/00153 | 1/1994 | |
| WO | WO 95/17210 | 6/1995 | |
| WO | WO 96/02555 | 2/1996 | |
| WO | WO 96/33739 | 10/1996 | |
| WO | WO 97/06685 | 2/1997 | |
| WO | WO 99/57150 | 11/1999 | |
| WO | WO-2007054658 A1 * | 5/2007 | C07K 14/47 |

(Continued)

OTHER PUBLICATIONS

Baldo et al., Amatuximab and novel agents targeting mesothelin for solid tumors, Onco Targets and Therapy, 2017: 10:5337-5353.*

(Continued)

*Primary Examiner* — Hong Sang

(74) *Attorney, Agent, or Firm* — Fish & Richardson P.C.

(57) ABSTRACT

The invention relates to fusion proteins comprising an antigen binding domain fused with a modified heat shock 70 protein. The invention further relates to methods of using the fusion proteins to induce an immune response to antigens and to treat diseases associated With antigens.

7 Claims, 6 Drawing Sheets

Figure 2A:
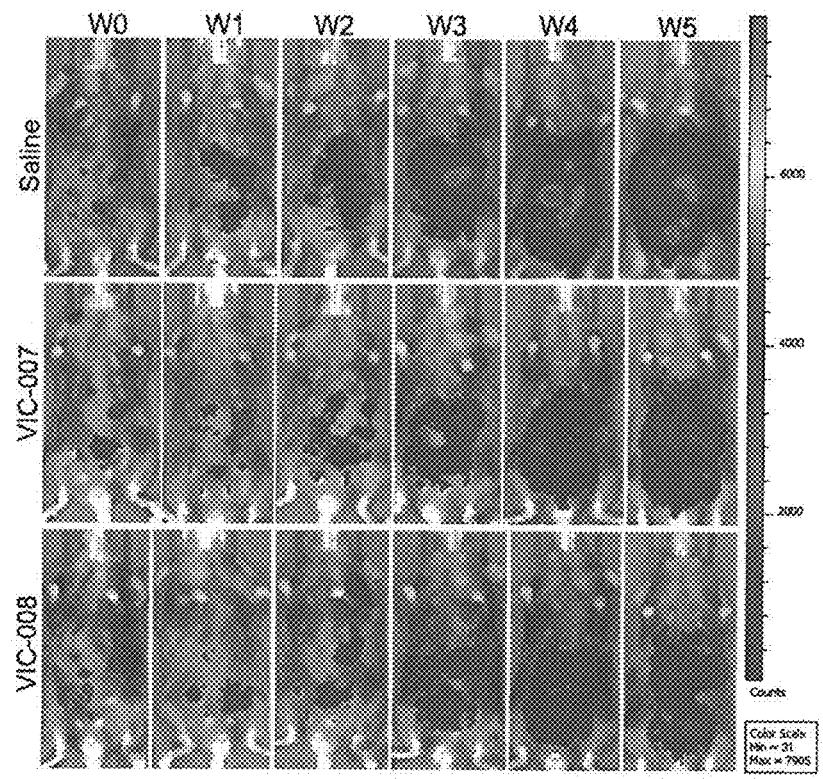

Specification includes a Sequence Listing.

(56) References Cited

FOREIGN PATENT DOCUMENTS

WO    WO 2007/136892    11/2007

OTHER PUBLICATIONS

Paul, Fundamental Immunology, 3rd Edition, 1993, pp. 292-295.*
Colman, Research in Immunology, 1994, 145:33-36.*
Rudikoff et al., Proc. Natl. Acad. Sci. USA, 1982, 79(6):1979-1983.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
English translation of CN-105481985-A, pub. date: Apr. 13, 2016.*
Ali et al., "The use of DNA viruses as vectors for gene therapy," Gene Therapy, Nov. 1994, 1(6):367-84.
Altschul et al., "Basic local alignment search tool," Journal of Molecular Biology, Oct. 5, 1990, 215(3):403-10.
Altschul et al., "Gapped BLAST and PSI-BLAST: a new generation of protein database search programs," Nucleic Acids Research, Sep. 1, 1997, 25(17):3389-402.
Altschul et al., "Local alignment statistics," Methods in Enzymology, May 1996, 266(21:460-80.
Argani et al., "Mesothelin is overexpressed in the vast majority of ductal adenocarcinomas of the pancreas: identification of a new pancreatic cancer marker by serial analysis of gene expression (SAGE)," Clinical Cancer Research, Dec. , 2001, 7(12):3862-8.
Baggiolini et al., "Chemokines and leukocyte traffic," Nature, Apr. 1998, 392(6676):565-8.
Bast et al., "The biology of ovarian cancer: new opportunities for translation," Nature Reviews Cancer, Jun. 2009, 9(6):415-28.
Beidler et al., "Cloning and high level expression of a chimeric antibody with specificity for human carcinoembryonic antigen," The Journal of Immunology, Dec. 1, 1988, 141(11):4053-60.
Ben-Bassat et al., "Processing of the initiation methionine from proteins: properties of the *Escherichia coli* methionine aminopeptidase and its gene structure," Journal of Bacteriology, Feb. 1, 1987, 169(2):751-7.
Bergan et al., "Development and in vitro validation of anti-mesothelin biobodies that prevent CA125/Mesothelin-dependent cell attachment," Cancer Letters, Oct. 8, 2007, 255(2):263-74.
Berkner et al., "Development of adenovirus vectors for the expression of heterologous genes," Biotechniques, Aug. 1988, 6(7):616-29.
Better et al., "*Escherichia coli* secretion of an active chimeric antibody fragment," Science, May 20, 1988, 240(4855):1041-3.
Bienenstock et al., "A common mucosal immunologic system involving the bronchus, breast and bowel," Secretory Immunity and Infection, 1978, 53-9.
Brisson et al., "Expression of a bacterial gene in plants by using a viral vector," Nature, Aug. 1984, 310(5977):511-4.
Broglie et al., "Light-regulated expression of a pea ribulose-1, 5-bisphosphate carboxylase small subunit gene in transformed plant cells," Science, May 25, 1984, 224:838-44.
Bujarski et al., "DNA inserted two bases down from the initiation site of a SP6 polymerase transcription vector is transcribed efficiently in vitro," Nucleic Acids Research, Feb. 11, 1987, 15(3):1337.
Cebra et al., "Origin and differentiation of lymphocytes involved in the secretory IgA response," Cold Spring Harbor Symposia on Quantitative Biology, Cold Spring Harbor Laboratory Press, Jan. 1, 1977, 41:201-215.
Cepko et al., "Construction and applications of a highly transmissible murine retrovirus shuttle vector," Cell, Jul. 1, 1984, 37(3):1053-62.
Chang et al., "Molecular cloning of mesothelin, a differentiation antigen present on mesothelium, mesotheliomas, and ovarian cancers," Proceedings of the National Academy of Sciences, Jan. 9, 1996, 93(1):136-40.

Cheng et al., "The structure of bacteriophage T7 lysozyme, a zinc amidase and an inhibitor of T7 RNA polymerase," Proceedings of the National Academy of Sciences, Apr. 26, 1994, 91(9):4034-8.
Ciupitu et al., "Immunization with a lymphocytic choriomeningitis virus peptide mixed with heat shock protein 70 results in protective antiviral immunity and specific cytotoxic T lymphocytes," The Journal of Experimental Medicine, Mar. 2, 1998, 187(5):685-91.
Coruzzi el al., "Tissue-specific and light-regulated expression of a pea nuclear gene encoding the small subunit of ribulose-1, 5-bisphosphate carboxvlase," The EMBO Journal, August 1.1984. 3(8):1671-9.
De Lorenzo et al., "Operator sequences of the aerobactin operon of plasmid ColV-K30 binding the ferric uptake regulation (fur) repressor," Journal of Bacteriology, Jun. 1, 1987, 169(6):2624-30.
Devereux et al., "A comprehensive set of sequence analysis programs for the VAX," Nucleic Acids Research, Jan. 11, 1984, 12:387-95.
Drinkwater et al., "Chemically induced mutagenesis in a shuttle vector with a low-background mutant frequency," Proceedings of the National Academy of Sciences, May 1, 1986, 83(10):3402-6.
Dubendorf et al., "Controlling basal expression in an inducible T7 expression system by blocking the target T7 promoter with lac repressor," Journal of Molecular Biology, May 5, 1991, 219(1):45-59.
Eisenbraun et al., "Examination of parameters affecting the elicitation of humoral immune responses by particle bombardment-mediated genetic immunization," DNA and Cell Biology, Nov. 1993, 12(9):791-7.
Feng et al., "Progressive sequence alignment as a prerequisiteto correct phylogenetic trees," Journal of Molecular Evolution, Aug. 1, 1987, 25(4):351-60.
Floto et al., "Dendritic cell stimulation by mycobacterial Hsp70 is mediated through CCR5," Science, Oct. 20, 2006, 314(5798):454-8.
Friedmann, "Progress toward human gene therapy," Science, Jun. 16, 1989, 244(4910):1275-81.
Frierson et al., "Large-scale molecular and tissue microarray analysis of mesothelin expression in common human carcinomas," Human Pathology, Jun. 1, 2003, 34(6):605-9.
Frydman et al., "Folding of nascent polypeptide chains in a high molecular mass assembly with molecular chaperones," Nature, Jul. 14, 1994, 370(6485):111-7.
Geller et al., "An efficient deletion mutant packaging system for defective herpes simplex virus vectors: potential applications to human gene therapy and neuronal physiology," Proceedings of the National Academy of Sciences, Nov. 1, 1990, 87(22):8950-4.
Goldberg et al., "Transcriptional regulation by iron of a Vibrio cholerae virulence gene and homology of the gene to the *Escherichia coli* fur system," Journal of Bacteriology, Dec. 1, 1990, 172(12):6863-70.
Gurley et al., "Upstream sequences required for efficient expression of a soybean heat shock gene," Molecular and Cellular Biology, Feb. 1, 1986, 6(2):559-65.
Hantke, "Regulation of ferric iron transport in *Escherichia coli* K12: isolation of a constitutive mutant," Molecular and General Genetics MGG, Jul. 1, 1981, 182(2):288-92.
Hassan et al., "Mesothelin targeted cancer immunotherapy," European Journal of Cancer, Jan. 1, 2008, 44(1):46-53.
Hassan et al., "Phase I clinical trial of the chimeric anti-mesothelin monoclonal antibody MORAb-009 in patients with mesothelin-expressing cancers," Clinical Cancer Research, Dec. 15, 2010, 16(24):6132-8.
Headley et al., "Expression of aerobactin genes by Shigella flexneri during extracellular and intracellular growth," Infection and Immunity, Feb. 1, 1997, 65(2):818-21.
Higgins et al., "Fast and sensitive multiple sequence alignments on a microcomputer," Bioinformatics, Apr. 1, 1989, 5(2):151-3.
Ho et al., "Mesothelin expression in human lung cancer," Clinical Cancer Research, Mar. 1, 2007, 13(5):1571-5.
Holliger et al., "Diabodies: small bivalent and bispecific antibody fragments," Proceedings of the National Academy of Sciences, Jul. 15, 1993, 90(14):6444-8.
Holliger et al., "Engineered antibody fragments and the rise of single domains," Nature Biotechnology, Sep. 2005, 23(9):1126-36.

(56) References Cited

OTHER PUBLICATIONS

Horwitz et al., "Selection of new biological activities from random nucleotide sequences: evolutionary and practical considerations," Genome, Jan. 1, 1989, 31(1):112-7.

Huang et al., "In vivo cytotoxic T lymphocyte elicitation by mycobacterial heat shock protein 70 fusion proteins maps to a discrete domain and is CD4+ T cell independent," The Journal of Experimental Medicine, Jan. 17, 2000, 191(2):403-8.

Hunt et al., "Promoter and operator determinants for fur-mediated iron regulation in the bidirectional fepA-fes control region of the Escherichia coli enterobactin gene system," Journal of Bacteriology, Jul. 1, 1994, 176(13):3944-55.

Inouye et al., "Up-promoter mutations in the lpp gene of Escherichia coli," Nucleic Acids Research, May 10, 1985, 13(9):3101-10.

Jaffee et al., "High efficiency gene transfer into primary human tumor explants without cell selection," Cancer Research, May 15, 1993, 53(10):2221-6.

Jones et al., "Replacing the complementarity-determining regions in a human antibody with those from a mouse," Nature, May 1986. 321(6069):522-5.

Karlin et al., "Applications and statistics for multiple high-scoring segments in molecular sequence," Proceedings of the National Academy of Sciences, Jun. 15, 1993, 90(12):5873-7.

Kipriyanov et al., "Bispecific tandem diabody for tumor therapy with improved antigen binding and pharmacokinetics," Journal of Molecular Biology, Oct. 15, 1999, 293(1):41-56.

Kreitman et al., "Phase I trial of continuous infusion anti-mesothelin recombinant immunotoxin SS1P," Clinical Cancer Research, Aug. 15, 2009, 15(16):5274-9.

Kyte et al., "A simple method for displaying the hydropathic character of a protein," Journal of Molecular Biology, May 5, 1982, 157(1):105-32.

Le Gall et al., "Di-, tri-and tetrameric single chain Fv antibody fragments against human CD19: effect of valency on cell binding," FEBS Letters, Jun. 18, 1999, 453(1-2):164-8.

Liao et al., "A simple high-efficiency method for random mutagenesis of cloned genes using forced nucleotide misincorporation," Gene, Mar. 30, 1990, 88(1):107-11.

Ling et al., "Immunization against the murine malaria parasite Plasmodium yoelii using a recombinant protein with adjuvants developed for clinical use," Vaccine, Oct. 1, 1997, 15(14):1562-7.

Liu et al., "Chimeric mouse-human IgG1 antibody that can mediate lysis of cancer cells," Proceedings of the National Academy of Sciences, May 1, 1987, 84(10):3439-43.

Liu et al., "Production of a mouse-human chimeric monoclonal antibody to CD20 with potent Fc-dependent biologic activity," The Journal of Immunology, Nov. 15, 1987, 139(10):3521-6.

Lu et al., "Di-diabody: a novel tetravalent bispecific antibody molecule by design," Journal of Immunological Methods, Aug. 1, 2003, 279(1-2):219-32.

MacAry et al., "HSP70 peptide binding mutants separate antigen delivery from dendritic cell stimulation," Immunity, Jan. 1, 2004, 20(1):95-106.

Mantia-Smaldone et al., "Immunotherapy in ovarian cancer," Human Vaccines & Immunotherapeutics, Sep. 16, 2012, 8(9):1179-91.

McCaughan et al., "Immune system of the gastrointestinal tract," International Review of Physiology, 1983, 28:131-57.

McNabb et al., "Host defense mechanisms at mucosal surfaces," Annual Reviews in Microbiology, Oct. 1981, 35(1):477-96.

Miller et al., "Improved retroviral vectors for gene transfer and expression," Biotechniques, Oct. 1989, 7(9):980-9.

Miller et al., "N-terminal methionine-specific peptidase in Salmonella typhimurium," Proceedings of the National Academy of Sciences, May 1, 1987, 84(9):2718-22.

Morrison et al., "Chimeric human antibody molecules: mouse antigen-binding domains with human constant region domains," Proceedings of the National Academy of Sciences, Nov. 1, 1984,81(21):6851-5.

Morrison, "Transfectomas provide novel chimeric antibodies," Science, Sep. 20, 1985, 229(4719):1202-7.

Muro-Cacho et al., "Gene transfer in human lymphocytes using a vector based on adeno-associated virus," Journal of Immunotherapy: Official Journal of the Society for Biological Therapy, May 1992, 11(4):231-7.

Murray et al., "Stress and immunological recognition in host-pathogen interactions," Journal of Bacteriology, Jul. 1992, 174(13):4193-6.

Needleman et al., "A general method applicable to the search for similarities in the amino acid sequence of two proteins," Journal of Molecular Biology, Mar. 28, 1970, 48(3):443-53.

Nishimura et al., "Recombinant human-mouse chimeric monoclonal antibody specific for common acute lymphocytic leukemia antigen," Cancer Research, Feb. 15, 1987, 47(4):999-1005.

O'Brien et al., "Stimulation of a major subset of lymphocytes expressing T cell receptor γδ by an antigen derived from Mycobacterium tuberculosis," Cell, May 19, 1989, 57(4):667-74.

Ochsner et al., "Role of the ferric uptake regulator of Pseudomonas aeruginosa in the regulation of siderophores and exotoxin A expression: purification and activity on iron-regulated promoters," Journal of Bacteriology Dec. 1, 1995, 177(24):7194-201.

Oi et al., "Chimeric antibodies," BioTechniques, 1986, 4(3):214-21.

Ordóñez, "Application of mesothelin immuno staining in tumor diagnosis," The American Journal of Surgical Pathology, Nov. 1, 2003, 27(11):1418-28.

Pääbo et al., "Structural and functional dissection of an MHC class I antigen-binding adenovirus glycoprotein," The EMBO Journal, Aug. 1, 1986, 5(8):1921-7.

Pearson et al., "Improved tools for biological sequence comparison," Proceedings of the National Academy of Sciences, Apr. 1, 1988, 85(8):2444-8.

Prince et al., "Regulation of toxA and regA by the Escherichia coli fur gene and identification of a Fur homologue in Pseudomonas aeruginosa PA103 and PA01," Molecular Microbiology, Nov. 1991, 5(11):2823-31.

Rabinovich et al., "Vaccine technologies: view to the future," Science, Sep. 2, 1994, 265(5177):1401-4.

Righi et al., "CXCL12/CXCR4 blockade induces multimodal antitumor effects that prolong survival in an immunocompetent mouse model of ovarian cancer," Cancer Research, Aug. 15, 2011, 71(16):5522-34.

Roby et al., "Development of a syngeneic mouse model for events related to ovarian cancer," Carcinogenesis, Apr. 1, 2000, 21(4):585-91.

Sagawa et al., "A tightly regulated expression system in Escherichia coli with SP6 RNA polymerase," Gene, Jan. 1, 1996, 168(1):37-41.

Schmitt et al., "Genetic analysis of the enterobactin gene cluster in Shigella flexneri," Journal of Bacteriology, Jan. 1, 1991, 173(2):816-25.

Shaw et al., "Mouse/human chimeric antibodies to a tumor-associated antigen: biologic activity of the four human IgG subclasses," JNCI: Journal of the National Cancer Institute, Dec. 7, 1988, 80(19):1553-9.

Siegel et al., "Cancer treatment and survivorship statistics, 2012," CA: A Cancer Kournal for Clinicians, Jul. 2012, 62(4):220-41.

Smith et al., "Comparison of biosequences," Advances in Applied Mathematics, Dec. 1, 1981, 2(4):482-9.

Smith et al., "Molecular engineering of the Autographa califomica nuclear polyhedrosis virus genome: deletion mutations within the polyhedrin gene," Journal of Virology, May 1, 1983, 46(2):584-93.

Studier et al., "Use of T7 RNA polymerase to direct expression of cloned genes," Methods Enzymol, Jun. 11, 1990;185:60-89.

Sun et al., "Chimeric antibody with human constant regions and mouse variable regions directed against carcinoma-associated antigen 17-1A," Proceedings of the National Academy of Sciences, Jan. 1, 1987, 84(1):214-8.

Suto et al., "A mechanism for the specific immunogenicity of heat shock protein-chaperoned peptides," Science, Sep. 15, 1995, 269(5230):1585-8.

Sutter et al., "Nonreplicating vaccinia vector efficiently expresses recombinant genes," Proceedings of the National Academy of Sciences, Nov. 15, 1992, 89(22):10847-51.

(56) References Cited

OTHER PUBLICATIONS

Suzue et al., "Adjuvant-free hsp70 fusion protein system elicits humoral and cellular immune responses to HIV-1 p24," The Journal of Immunology, Jun. 15, 1996, 156(2):873-9.

Svinarich et al., "Regulation of the SLT-1A toxin operon by a ferric uptake regulatory protein in toxinogenic strains of Shigella dysenteriae type 1," Journal of Diarrhoeal Diseases Research, Sep. 1992, 1:139-45.

Takamatsu et al., "Expression of bacterial chloramphenicol acetyltransferase gene in tobacco plants mediated by TMV-RNA," The EMBO Journal, Feb. 1, 1987, 6(2):307-11.

Tang et al., "The role of mesothelin in tumor progression and targeted therapy," Anti-Cancer Agents in Medicinal Chemistry (Formerly Current Medicinal Chemistry—Anti-Cancer Agents), Feb. 1, 2013, 13(2):276-80.

Udono et al., "Heat shock protein 70-associated peptides elicit specific cancer immunity," The Journal of Experimental Medicine, Oct. 1, 1993, 178(4):1391-6.

Van Eden et al., "Cloning of the mycobacterial epitope recognized by T lymphocytes in adjuvant arthritis," Nature, Jan. 1988, 331(6152):171-3.

Verhoeyen et al., "Reshaping human antibodies: grafting an antilysozyme activity," Science, Mar. 25, 1988, 239(4847):1534-6.

Wang et al., "CD40 is a cellular receptor mediating mycobacterial heat shock protein 70 stimulation of CC-chemokines," Immunity, Dec. 1, 2001, 15(6):971-83.

Wang et al., "Second-generation adenovirus vectors," Nature Medicine, Jun. 1996, 2(6):714-6.

Weisz-Carrington et al., "Organ and isotype distribution of plasma cells producing specific antibody after oral immunization: evidence for a generalized secretory immune system," The Journal of Immunology, Oct. 1, 1979, 123(4):1705-8.

Williams et al., "Inhibition of bacterial adherence by secretory immunoglobulin A: a mechanism of antigen disposal," Science, Aug. 25, 1972, 177(4050):697-9.

Winter et al., "Man-made antibodies," Nature, Jan. 1991, 349(6307):293-9.

Wood et al., "The synthesis and in vivo assembly of functional antibodies in yeast," Nature, Apr. 4, 1985, 314(6010):446-9.

Young et al., Stress proteins, infection, and immune surveillance, Cell, Oct. 6, 1989, 59(1):5-8.

Yuan et al., "A novel mycobacterial Hsp70-containing fusion protein targeting mesothelin augments antitumor immunity and prolongs survival in murine models of ovarian cancer and mesothelioma," Journal of Hematology & Oncology, Dec. 1, 2014, 7(1):15.

Zatloukal et al., "In vivo production of human factor VII in mice after intrasplenic implantation of primary fibroblasts transfected by receptor-mediated, adenovirus-augmented gene delivery," Proceedings of the National Academy of Sciences, May 24, 1994, 91(11):5148-52.

International Preliminary Report on Patentability In International Appln. No. PCT/US2017/021911, dated Sep. 20, 2018, 9 pages.

International Search Report and Written Opinion in International Appln. No. PCT/US2017/021911, dated Aug. 29, 2017, 13 pages.

Wang et al., "Identification of Stimulating and Inhibitory Epitopes within the Heat Shock Protein 70 Molecule That Modulate Cytokine Production and Maturation of Dendritic Cells," J Immunol., 2005, 174:3306-3316.

Office Action in Chinese Appln. No. 201780029242.5, dated Mar. 10, 2022, 17 pages (with English translation).

Office Action in Mexican Appln. No. MX/a/2018/010961, dated Sep. 14, 2022, 18 pages (with English machine translation).

\* cited by examiner

FIG. 1

(SEQ ID NO: 28)
GSSQVQLQQSGPGLVTPSQTLSLTCAISGDSVSSNSATWNWIRQSPSRGLEWLGRTYYRS
KWYNDYAVSVKSRMSINPDTSKNQFSLQLNSVTPEDTAVYYCARGMMTYYYGMDVWGQGT
TVTVSSGILGSGGGGSGGGGSGGGGSQPVLTQSSSLSASPGASASLTCTLRSGINVGPYR
IYWYQQKPGSPPQYLLNYKSDSDKQQGSGVPSRFSGSKDASANAGVLLISGLRSEDEADY
YCMIWHSSAAVFGGGTQLTVLSGILEQQGGGGGSGGGGSGGGGSAAAMRSMARAVGIDLG
TTNSVVSVLEGGDPVVVANSEGSRTTPSIVAFARNGEVLVGQPAKNQAVTNVDRTVRSVK
RHMGSDWSIEIDGKKYTAPEISARILMKLKRDAEAYLGEDITDAVITTPAYFNDAQRQAT
KDAGQIAGLNVLRIVNEPTAAALAYGLDKGEKEQRILVFDLGGGTFDVSLLEIGEGVVEV
RATSGDNHLGGDDWDQRVVDWLVDKFKGTSGIDLTKDKMAMQRLREAAEKAKIELSSSQS
TSINLPYITVDADKNPLFLDEQLTRAEFQRITQDLLDRTRKPFQSVIADTGISVSEIDHV
VLVGGSTRMPAVTDLVKELTGGKEPNKGVNPDEVVAVGAALQAGVLKGEVKDVLLLDVTP
LSLGIETKGGVMTRLIERNTTIPTKRSETFTTADDNQPSVQIQVYQGEREIAAHNKLLGS
FELTGIPPAPRGIPQIEVTFDIDANGIVHVTAKDKGTGKENTIRIQEGSGLSKEDIDRMI
KDAEAHAEEDRKRREEADVRNQAETLVYQTEKFVKEQREAEGGSKVPEDTLNKVDAAVAE
AKAALGGSDISAIKSAMEKLGQESQALGQAIYEAAQAASQATGAAHPGGEPGGAHPGSAD
DVVDAEVVDDGREAK (SEQ ID NO: 27)
QVQLQQSGPGLVTPSQTLSLTCAISGDSVSSNSATWNWIRQSPSRGLEWLGRTYYRSKWY
NDYAVSVKSRMSINPDTSKNQFSLQLNSVTPEDTAVYYCARGMMTYYYGMDVWGQGTTVT
VSSGILGSGGGGSGGGGSGGGGSQPVLTQSSSLSASPGASASLTCTLRSGINVGPYRIYW
YQQKPGSPPQYLLNYKSDSDKQQGSGVPSRFSGSKDASANAGVLLISGLRSEDEADYYCM
IWHSSAAVFGGGTQLTVLGGGSGGGGSGGGGSMARAVGIDLGTTNSVVSVLEGGDPVVV
ANSEGSRTTPSIVAFARNGEVLVGQPAKNQAVTNVDRTVRSVKRHMGSDWSIEIDGKKYT
APEISARILMKLKRDAEAYLGEDITDAVITTPAYFNDAQRQATKDAGQIAGLNVLRIVNE
PTAAALAYGLDKGEKEQRILVFDLGGGTFDVSLLEIGEGVVEVRATSGDNHLGGDDWDQR
VVDWLVDKFKGTSGIDLTKDKMAMQRLREAAEKAKIELSSSQSTSINLPYITVDADKNPL
FLDEQLTRAEFQRITQDLLDRTRKPFQSVIADTGISVSEIDHVVLVGGSTRMPAVTDLVK
ELTGGKEPNKGVNPDEVVAVGAALQAGVLKGEVKDVLLLDVTPLSLGIETKGGFMTRLIE
RNTTIPTKRSETFTTADDNQPSVQIQVYQGEREIAAHNKLLGSFELTGIPPAPRGIPQIE
VTFDIDANGIVHVTAKDKGTGKENTIRIQEGSGLSKEDIDRMIKDAEAHAEEDRKRREEA
DVRNQAETLVYQTEKFVKEQREAEGGSKVPEDTLNKVDAAVAEAKAALGGSDISAIKSAM
EKLGQESQALGQAIYEAAQAASQATGAAHPGGEPGGAHPGSADDVVDAEVVDDGREAK

US 11,718,683 B2

ANTIGEN-BINDING FUSION PROTEINS WITH MODIFIED HSP70 DOMAINS

STATEMENT OF PRIORITY

This application is a continuation of and claims priority to U.S. patent application Ser. No. 15/456,196, filed Mar. 10, 2017 which claims the benefit of U.S. Provisional Application No. 62/306,168, filed Mar. 10, 2016, the entire contents of each of which are incorporated by reference herein.

STATEMENT OF FEDERAL SUPPORT

This invention was made with government support under Grant No. W81XWH-14-1-0206 awarded by the Department of Defense. The government has certain rights in this invention.

STATEMENT REGARDING ELECTRONIC FILING OF A SEQUENCE LISTING

A Sequence Listing in ASCII text format, submitted under 37 C.F.R. § 1.821, entitled 1417-3CT_ST25.txt, 76,887 bytes in size, generated on Aug. 5, 2019 and filed via EFS-Web, is provided in lieu of a paper copy. This Sequence Listing is hereby incorporated by reference into the specification for its disclosures.

STATEMENT REGARDING ELECTRONIC FILING OF A SEQUENCE LISTING

A Sequence Listing in ASCII text format, submitted under 37 C.F.R. § 1.821, entitled 40978-0439002_SL_ST26, 84,498 bytes in size, generated on Feb. 15, 2023 and filed via EFS-Web, is provided in lieu of a paper copy.

FIELD OF THE INVENTION

The invention relates to fusion proteins comprising an antigen binding domain fused with a modified heat shock 70 protein. The invention further relates to methods of using the fusion proteins to induce an immune response to antigens and to treat diseases associated with antigens.

BACKGROUND OF THE INVENTION

Mesothelin is a differentiation antigen whose expression in normal human tissues is limited to mesothelial cells lining the pleura, pericardium and peritoneum. However, mesothelin is highly expressed in several human cancers, including mesotheliomas, pancreatic adenocarcinomas, ovarian cancers and lung adenocarcinomas. Mesothelin is an appropriate target for methods of disease prevention or treatment and antibodies specific for mesothelin, and vaccines comprising mesothelin are useful for prophylactic and therapeutic methods.

Classical monoclonal antibodies are currently produced in mammalian cells. Drawbacks of this method of production include the difficulty of producing and selecting appropriate clones, and the expense of culturing mammalian cells. The "next generation" of monoclonal antibodies are being engineered in *E. coli*. Recently, microbial expression of $V_H$ and $V_L$ domains tethered together by polypeptide linkers has created the capability of generating engineered "mini-antibodies." These mini-bodies can be generated in *E. coli* in a virtually combinatorial fashion. These artificially created Fab or single chain FAT (scFv) can be linked together to form multimers, e.g., diabodies, triabodies and tetrabodies. Although they are capable of binding to antigens with almost antibody-like efficiency, these engineered, Fc deficient mini-antibodies lack the ability to interact with antigen presenting cells and are poorly immunogenic. Existing solutions to the lack of immunogenicity of engineered antibodies involve directing one of the antigen binding sites to bind directly with immune cells. This brings them in apposition, but does not result in the same MHC class I priming as would be observed for a monoclonal antibody.

Immunization with vaccines remains a cornerstone of protection against threat of disease and infection. The key difficulty in vaccine development is rapidly matching a vaccine, or antitoxin, to a specific threat. Current vaccine development strategies rely on the identification and characterization of antigens that can be targeted to successfully eradicate infection or disease. Current vaccine development strategies are time- and labor-intensive and can only commence once a threat emerges. Such strategies are also impractical for generating personalized vaccines to combat disease for which target antigens varies among individuals. Current vaccine development strategies are therefore insufficient if a new and serious threat were to emerge, for which sufficient time were not available to identify and characterize target antigens before such a threat could be contained. Current vaccine development strategies are also insufficient for generating personalized vaccines for the general population.

U.S. Pat. Nos. 7,749,501 and 7,943,133 describe fusion proteins comprising an engineered antibody fused to a stress protein to enhance the immune response to an antigen.

The present invention addresses previous shortcomings in the art by disclosing modified fusion proteins with enhanced immunostimulatory and therapeutic properties.

SUMMARY OF THE INVENTION

The present invention is based, in part, on the development of several modifications of *Mycobacterium tuberculosis* heat shock protein 70 (HSP70) that, alone or in combination, enhance the effectiveness of an antigen-binding fusion protein comprising the modified HSP70 to stimulate an immune response against an antigen and to treat diseases associated with an antigen.

Thus, one aspect of the invention relates to a fusion protein comprising an antigen binding domain fused in frame to a fragment of *Mycobacterium tuberculosis* heat shock protein 70 (HSP70) of less than 200 amino acids, wherein the HSP70 fragment comprises a minimal HSP70 sequence.

Another aspect of the invention relates to a fusion protein comprising an antigen binding domain fused in frame to a fragment of *Mycobacterium tuberculosis* heat shock protein 70 (HSP70) of at least 100 amino acids and comprising no more than amino acids 1-495 of SEQ ID NO:1.

A further aspect of the invention relates to a fusion protein comprising an antigen binding domain fused in frame to a fragment of *Mycobacterium tuberculosis* heat shock protein 70 (HSP70) comprising the amino acid sequence of SEQ ID NO:26 (sequence from provisional).

Another aspect of the invention relates to a fusion protein comprising an antigen binding domain fused in frame to a chimeric *Mycobacterium tuberculosis* heat shock protein 70 (HSP70), wherein the chimeric HSP70 comprises a backbone of a human HSP70 amino acid sequence wherein a beta sheet domain of about amino acid residues 367 to 479 (numbering based on SEQ ID NO:29) are substituted with a beta sheet domain of about amino acid residues 395 to 541 of *M. tuberculosis* HSP70 (numbering based on SEQ ID NO:1).

An additional aspect of the invention relates to a pharmaceutical composition comprising an effective amount of the fusion protein of the invention and a pharmaceutically acceptable carrier.

Another aspect of the invention relates to an immunogenic composition or vaccine comprising the fusion protein of the invention.

A further aspect of the invention relates to a kit comprising the fusion protein of the invention and packaging means thereof.

An additional aspect of the invention relates to an isolated nucleic acid encoding the fusion protein of the invention and expression vectors and cells comprising the nucleic acid.

Another aspect of the invention relates to a method for inducing an immune response to an antigen in a subject, comprising administering to the subject the fusion protein of the invention that specifically binds the antigen, thereby inducing an immune response.

A further aspect of the invention relates to a method of treating a disease associated with an antigen in a subject in need thereof, comprising administering to the subject a therapeutically effective amount of the fusion protein of the invention that specifically binds the antigen, thereby treating the disease.

These and other aspects of the invention are set forth in more detail in the description of the invention below.

BRIEF DESCRIPTION OF THE DRAWINGS

FIG. 1 shows the amino acid sequences of VIC-007 (SEQ ID NO:28) and VIC-008 (SEQ ID NO:27). VIC-008 was reconstructed from VIC-007 by removal of redundant amino acids GSS, SGILEQQG, and AAAMRS indicated in bold and italic and introduction of a single amino acid mutation, phenylalanine (F) in place of valine (V), at position 381 of MtbHsp70.

FIGS. 2A-2B show tumor growth. Quantitative analysis of bioluminescence signals was performed using IVIS Spectrum on Luc-ID8 tumor inoculated mice (n=8 or 9) at a week after tumor inoculation and subsequently weekly. (A) Longitudinal images of a representative mouse from each treatment group were presented from a week after tumor inoculation before treatment (W0) and subsequent five weeks (W1-W5). (B) The arrows indicated 4 treatments at 7-day intervals starting at a week after tumor inoculation. Total photons were calculated by IVIS Lumina Series III. Statistical differences were analyzed using Two-Way ANOVA followed by Tukey's multiple comparison tests. ****, $p<0.0001$. Data were indicated as the mean±sem.

FIG. 3 shows mouse survival after treatment. The mice were observed daily 1 week after treatment. At the endpoint the mice were euthanized and the survival time were calculated as life span from the day of tumor inoculation. The median survival and p values were determined using the Log-rank test.

FIG. 4 shows ovarian cancer tumor growth in the first five weeks after start of therapy (week 0). C57BL/6 mice intraperitoneally injected with $5\times10^6$ luciferase-expressing ID8 mouse ovarian cancer cells. 10 mice in saline-treated control group; 11 mice in VIC-008 treatment group. Mice received four weekly treatments starting one week after tumor introduction. Treatment dose of VIC-008 was 20 μg per mouse. Luciferase signal was monitored by IVIS. Statistical significance was established using two-way ANOVA test.

FIG. 5 shows mouse survival after injection with ovarian cancer cells. C57BL/6 mice intraperitoneally injected with $5\times10^6$ luciferase-expressing ID8 mouse ovarian cancer cells. 10 mice in saline-treated control group; 11 mice in VIC-008 treatment group. Mice received four weekly treatments starting one week after tumor introduction. Treatment dose of VIC-008 was 20 μg per mouse. Statistical significance was established using log-rank (Mantel-Cox) test.

FIG. 6 shows intratumoral CD8+ T cell infiltration. Tumor samples were collected two weeks after the fourth and final treatment of either saline or VIC-008. Tumor tissue was collected and immunoprofiled using flow cytometry to detect CD3+ CD8+ T cells. T cells were counted as a percentage of gated live cells.

FIG. 7 shows intratumoral Treg T cell infiltration. Tumor samples were collected two weeks after the fourth and final treatment of either saline or VIC-008. Tumor tissue was collected and immunoprofiled using flow cytometry to detect CD4+CD25+FoxP3+ T regulatory cells. T regulatory cells were counted as a percentage of all CD3+CD4+ cells.

FIG. 8 shows the ratio of CD8+ T cells to T regulatory cells in tumor. Tumor samples were collected two weeks after the fourth and final treatment of either saline or VIC-008. Tumor tissue was collected and immunoprofiled using flow cytometry to detect both CD3+CD8+ T cells and CD4+CD25+ FoxP3+ T regulatory cells. Ratio was calculated based on percentages of the observed population.

FIG. 9 shows intratumoral central memory CD8+ T cell infiltration. Tumor samples were collected two weeks after the fourth and final treatment of either saline or VIC-008. Tumor tissue was collected and immunoprofiled using flow cytometry to detect CD8+CD44+CD27+ central memory T cells. CD8+ central memory T cells were counted as a percentage of all CD3+CD8+ cells.

DETAILED DESCRIPTION OF THE INVENTION

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

Amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

In this disclosure, "comprises," "comprising," "containing," and "having" and the like have the open-ended meaning ascribed to them in U.S. patent law and mean "includes," "including," and the like.

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polypeptide or polynucleotide sequence of this invention, means a polypeptide or polynucleotide that consists of both the recited sequence (e.g., SEQ ID NO) and a total often or less (e.g., 1, 2, 3, 4, 5, 6, 7, 8, 9, or 10) additional amino acids on the N-terminal and/or C-terminal ends of the recited sequence or additional nucleotides on the 5' and/or 3'ends such that the function of the polypeptide or polynucleotide is not materially altered. The total often or less additional amino acids or nucleotides includes the total number of additional amino acids or nucleotides on both ends added together. The term "materially altered," as applied to polypeptides of the invention, refers to an increase or decrease in immunostimulatory activity (e.g., towards a mesothelin-containing tumor) of at least about 50% or more as compared to the activity of a polypeptide consisting of the recited sequence. The term "materially altered," as applied to polynucleotides of the invention. refers to an increase or decrease in ability to express an encoded polypeptide of at least about 50% or more as compared to the activity of a polynucleotide consisting of the recited sequence.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

The term "contact" or grammatical variations thereof as used with respect to a polypeptide and a calcium channel, refers to bringing the polypeptide and the calcium channel in sufficiently close proximity to each other for one to exert a biological effect on the other. In some embodiments, the term contact means binding of the polypeptide to the calcium channel.

By the terms "treat," "treating," or "treatment of," it is intended that the severity of the subject's condition is reduced or at least partially improved or modified and that some alleviation, mitigation or decrease in at least one clinical symptom is achieved.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "prophylactically effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein "mesothelin" refers to a differentiation antigen whose expression in normal human tissues is limited to mesothelial cells lining the pleura, pericardium and peritoneum. However, mesothelin is highly expressed in several human cancers, including mesotheliomas, pancreatic adenocarcinomas, ovarian cancers and lung adenocarcinomas. The mesothelin gene encodes a precursor protein of 71 kDa that is processed to a 31 kDa shed protein called megakaryocyte potentiating factor (MPF) and a 40 kDa fragment, mesothelin, that is attached to the cell membrane by a glycosyl-phosphatidylinositol (GPI) anchor.

There are three (3) variants of mesothelin: soluble mesothelin-1, a unique mesothelin-2 transcript, and a mesothelin-3 variant with an extended C-terminus. Mesothelin-1 is found in pleura, pericardium and peritoneum and on surface epithelium of the ovaries, tonsils, and fallopian tubes (Ordonez, 2003). Mesothelin is also overexpressed in mesotheliomas, pancreatic adenocarcinomas, and squamous cell carcinomas of the head, neck, lung, esophagus, cervix, and vulva (Chang and Pastan 1992, 1996; Frierson et al. 2003).

The term "administering" includes any method of delivery of a compound of the present invention, including but not limited to, a pharmaceutical composition or therapeutic agent, into a subject's system or to a particular region in or on a subject, including systemic or localized administration. The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration "Parenteral administration" and "administered parenterally" means modes of administration other than enteral and topical administration, usually by injection, and includes, without limitation, intravenous, intramuscular, intralesional, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection, oral, epidural, intranasal and infusion The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, IgE and IgY. In exemplary embodiments, antibodies used with the methods and compositions described herein are derivatives of the IgG class. The term "antibody" also includes an antibody fragment as defined herein.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')$_2$ fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY). Examples of engineered antibodies include enhanced single chain monoclonal antibodies and enhanced monoclonal antibodies. Examples of engineered antibodies are further described in PCT/US2007/061554, the entire contents of which are incorporated herein by reference. An "engineered antibody" includes an engineered antibody fragment, according to the method of the invention, and as defined herein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific," "bispecific," "trispecific," "tetraspecific," etc., refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

An "antigen" refers to a target of an immune response induced by a composition described herein. An antigen may be a protein antigen and is understood to include an entire protein, fragment of the protein exhibited on the surface of a virus or an infected, foreign, or tumor cell of a subject, as well as a peptide displayed by an infected, foreign, or tumor cell as a result of processing and presentation of the protein, for example, through the typical MHC class 1 or II pathways. Examples of such foreign cells include bacteria, fungi, and protozoa. Examples of bacterial antigens include Protein A (PrA), Protein G (PrG), and Protein L (PrL).

The term "antigen binding site" refers to a region of an antibody or fragment thereof, that specifically binds an epitope on an antigen.

The term "costimulatory molecule" as used herein includes any molecule which is able to either enhance the stimulating effect of an antigen-specific primary T cell stimulant or to raise its activity beyond the threshold level required for cellular activation, resulting in activation of naive T cells. Such a costimulatory molecule can be a membrane-resident receptor protein.

The term "effective amount" refers to that amount of a compound, material, or composition which is sufficient to effect a desired result. An effective amount of a compound can be administered in one or more administrations.

A "fusion protein" or "fusion polypeptide" refers to a hybrid polypeptide which comprises polypeptide portions from at least two different polypeptides. A "fusion protein" as defined herein, is a fusion of a first amino acid sequence (protein) comprising, for example a stress protein of the invention, joined to a second amino acid sequence comprising an antibody or fragment thereof that binds specifically to mesothelin or a biotin-binding protein. A fusion protein also includes a fusion protein comprising a first amino acid sequence comprising a stress protein, and a second amino acid sequence comprising a biotin binding protein. A fusion protein also includes a fusion protein comprising a first amino acid sequence comprising a stress protein and second amino acid sequence comprising an antibody binding protein. A fusion protein also includes a fusion protein comprising a first amino acid sequence comprising an antibody or fragment thereof that binds specifically to mesothelin and a second amino acid sequence comprising a biotin binding protein or an antibody binding protein.

The portions may be from proteins of the same organism, in which case the fusion protein is said to be "interspecies," "intergenic," etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "linker" is art-recognized and refers to a molecule (including but not limited to unmodified or modified nucleic acids or amino acids) or group of molecules (for example, 2 or more, e.g., 2, 3, 4, 5, 6, 7, 8, 9, 10, 15, 20, 25, 30, 35, 40, 45, 50, 55, 60, 65, 70, 75, 80, 85, 90, 95, 100 or more) connecting two compounds, such as two polypeptides. The linker may be comprised of a single linking molecule or may comprise a linking molecule and at least one spacer molecule, intended to separate the linking molecule and a compound by a specific distance.

A "spacer molecule" includes any amino acid segment that is not related to the two protein segments it separates. For example, in a fusion consisting of a stress protein and a biotin protein, a spacer molecule would consist of a stretch of amino acids that is unrelated to the proteins comprising the fusion protein. A "spacer molecule" useful according to the invention includes neutral amino acids such as glycine, leucine, valine, alanine, rather than acidic or basic amino acids like aspartate, or arginine respectively.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc.), may be transfected into cells, e.g., in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

"Host cell" refers to a cell that may be transduced with a specified transfer vector. The cell is optionally selected from in vitro cells such as those derived from cell culture, ex vivo cells, such as those derived from an organism, and in vivo cells, such as those in an organism. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "including" is used herein to mean "including but not limited to." "Including" and "including but not limited to" are used interchangeably.

The term "immunogenic" refers to the ability of a substance to elicit an immune response. An "immunogenic composition" or "immunogenic substance" is a composition or substance which elicits an immune response. An "immune response" refers to the reaction of a subject to the presence of an antigen, which may include at least one of the following: antibody production, inflammation, developing immunity, developing hypersensitivity to an antigen, the response of antigen specific lymphocytes to antigen, tolerance, and transplant or graft rejection.

As used herein, "an immune response to an antigen" means, for example, a humoral or cellular response to the antigen.

If a patient is mounting a humoral immune response to the antigen, anti-antigen antibody titer is measured. A typical immunoassay consists of coating the wells of an immunoassay plate with the antigen (for example by adding recombinant antigen or using a capture anti-antigen antibody) and then adding serial dilutions of patient serum to the wells. After washing away the sera, human immunoglobulins are detected with a conjugated anti-human immunoglobulin.

A cellular immune response is measured by using a cell-killing assay. Patients peripheral blood lymphocytes (PBL) are isolated and added at different ratios to a CHO cell line expressing the antigenn (non-transfected CHO cells or CHO cells transfected with a non-antigen construct are used as negative control). The antigen expressing CHO cells are transfected with an antigen construct and selected to express antigen on their surface. Killing is measured using radioactivity or release of a specific dye.

As used herein, "treating a disease" means reducing the amount of soluble antigen in the plasma of patients. Treating a disease also refers to reducing the tumor burden as measured by clinical means (for example by ecography or other methods known in the art. Treating a disease also refers to reducing tumor size/mass and/or prevention of metastases.

The enhanced mesothelin antibody as described herein, will reduce (eliminate) the tumor burden in patients diagnosed with, e.g., ovarian cancer, meningiomas, gliomas and metastases to the leptomininges, mesotheliomas, adenocarcinoma of the uterus, malignant mesothelioma, pancreatic cancer, and lung adenocarcinoma.

The term "isolated polypeptide" or "isolated protein" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

"Isolating" a polypeptide or protein refers to the process of removing a polypeptide from a tissue, cell or any mixture of polypeptides which are not polypeptides or proteins of interest. An isolated polypeptide or protein will be generally free from contamination by other polypeptides or proteins. An isolated polypeptide or protein can exist in the presence of a small fraction of other polypeptides or proteins which do not interfere with the utilization of the polypeptide or protein of interest. Isolated polypeptides or proteins will generally be at least 30%, 35%, 40%, 45%, 50%, 55%, 60%, 65%, 70%, 75%, 80%, 85%, 90%, 95%, 96%, 97%, 98%, 99% or 100% pure. In one embodiment, isolated polypeptides or proteins according to the invention will be at least 98% or 99% pure.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

"Isolating" a nucleic acid refers to the process of removing a nucleic acid from a tissue, cell or any mixture of nucleic acids which are not nucleic acids of interest. An isolated nucleic acid will be generally free from contamination by other nucleic acids. An isolated nucleic acid can exist in the presence of a small fraction of other nucleic acids which do not interfere with the utilization of the nucleic acid of interest. Isolated nucleic acids will generally be at least 30%, 35%, 40%, 45%, 50%, 55%, 60%, 65%, 70%, 75%, 80%, 85%, 90%, 95%, 96%, 97%, 98%, 99% or 100% pure. In one embodiment, isolated nucleic acids according to the invention will be at least 98% or 99% pure.

It will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature (See, e.g., Table 1).

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

When referring to "polypeptide" herein, a person of skill in the art will recognize that a protein can be used instead, unless the context clearly indicates otherwise. A "protein" may also refer to an association of one or more polypeptides.

The term "nucleic acid" refers to a polymeric form of nucleotides, either ribonucleotides or deoxynucleotides, a combination of ribo and deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

Unless the context clearly indicates otherwise, "protein," "polypeptide," and "peptide" are used interchangeably herein when referring to a gene expression product, e.g., an amino acid sequence as encoded by a coding sequence. A "protein" may also refer to an association of one or more proteins, such as an antibody. A "protein" may also refer to a protein fragment. A protein may be a post-translationally modified protein such as a glycosylated protein.

A "protein" according to the invention includes a protein wherein one or more (for example, 1, 2, 3, 4, 5, 6, 7, 8, 9, 10, 20, 30, 40, 50, 60, 70, 80, 90, 100 or more) amino acids are not identical to the amino acids of the corresponding wild type protein. A "protein" according to the invention includes a protein wherein one or more (for example, 1, 2, 3, 4, 5, 6, 7, 8, 9, 10, 20, 30, 40, 50, 60, 70, 80, 90, 100 or more) amino acids have been deleted as compared to the corresponding wild type protein. A "protein" according to the invention includes a protein wherein one or more (for example, 1, 2, 3, 4, 5, 6, 7, 8, 9, 10 or more) amino acids have been added and/or substituted as compared the corresponding wild type protein It will be understood that the polypeptides specifically disclosed herein will typically tolerate substitutions (e.g., conservative substitutions) in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 1

| Amino Acid | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, *J Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors. DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (-0.4); proline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4).

Thus, the hydrophilicity of the amino acid (or amino acid sequence) may be considered when identifying additional polypeptides beyond those specifically disclosed herein.

As used herein, the term "homolog" is used to refer to a molecule which differs from a naturally occurring polypeptide by minor modifications to the naturally occurring polypeptide, but which significantly retains a biological activity of the naturally occurring polypeptide. Minor modifications include, without limitation, changes in one or a few amino acid side chains, changes to one or a few amino acids (including deletions, insertions, and/or substitutions), changes in stereochemistry of one or a few atoms, and minor derivatizations, including, without limitation, methylation, glycosylation, phosphorylation, acetylation, myristoylation, prenylation, palmitoylation, amidation, and addition of glycosylphosphatidyl inositol. The term "substantially retains," as used herein, refers to a fragment, homolog, or other variant of a polypeptide that retains at least about 50% of the activity of the naturally occurring polypeptide (e.g., binding to or inhibiting a calcium channel), e.g., about 70%, 80%, 90% or more. Other biological activities, depending on the polypeptide, may include pH sensitivity, enzyme activity, receptor binding, ligand binding, induction of a growth factor, a cell signal transduction event, etc.

In certain embodiments, the polypeptide of the invention comprises at least one modified terminus, e.g., to protect the polypeptide against degradation. In some embodiments, the N-terminus is acetylated and/or the C-terminus is amidated. In some embodiments, the polypeptide comprises one or two D-alanines at the amino- and/or carboxyl-terminal ends.

In certain embodiments, the polypeptide of the invention comprises at least one non-natural amino acid (e.g., 1, 2, 3, or more) or at least one terminal modification (e.g., 1 or 2).

In some embodiments, the peptide comprises at least one non-natural amino acid and at least one terminal modification.

By "gene expression product" is meant a molecule that is produced as a result of transcription of an entire gene or a portion of a gene. Gene products include RNA molecules transcribed from a gene, as well as proteins translated from such transcripts. Proteins may be naturally occurring isolated proteins or may be the product of recombinant or chemical synthesis. The term "protein fragment" refers to a protein in which amino acid residues are deleted as compared to the reference protein itself, but where the remaining amino acid sequence is usually identical to or substantially identical (for example, 100%, 99%, 95%, 90%, 85%, 80%, 75%, 70%, 65%, or 60% identical) to that of the reference protein. Such deletions may occur at the amino-terminus or carboxy-terminus of the reference protein, or alternatively both. Deletions may also occur internally.

Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. Fragments may be obtained using proteinases to fragment a larger protein, or by recombinant methods, such as the expression of only part of a protein-encoding nucleotide sequence (either alone or fused with another protein-encoding nucleic acid sequence). In various embodiments, a fragment may comprise an enzymatic activity and/or an interaction site of the reference protein to, e.g., a cell receptor. In another embodiment, a fragment may have immunogenic properties. The proteins may include mutations introduced at particular loci by a variety of known techniques, which do not adversely effect, but may enhance, their use in the methods provided herein. A fragment can retain one or more of the biological activities of the reference protein.

As used herein, a "functional" peptide or "functional fragment" is one that substantially retains at least one biological activity normally associated with that peptide (e.g., binding to or inhibiting a calcium channel). In particular embodiments, the "functional" peptide or "functional fragment" substantially retains all of the activities possessed by the unmodified peptide. By "substantially retains" biological activity, it is meant that the peptide retains at least about 50%, 60%, 75%, 85%, 90%, 95%, 97%, 98%, 99%, or more, of the biological activity of the native polypeptide (and can even have a higher level of activity than the native peptide). A "non-functional" peptide is one that exhibits little or essentially no detectable biological activity normally associated with the peptide (e.g., at most, only an insignificant amount, e.g., less than about 10% or even 5%). Biological activities such as protein binding and calcium channel inhibitory activity can be measured using assays that are well known in the art and as described herein.

A "patient" or "subject" or "host" refers to either a human or non-human animal.

A "subject" includes both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A "pharmaceutically-acceptable salt" refers to the relatively non-toxic, inorganic and organic acid addition salts of compounds.

As used herein, a "stress protein," also known as a "heat shock protein" or "Hsp," is a protein that is encoded by a stress gene, and is therefore typically produced in significantly greater amounts upon the contact or exposure of the stressor to the organism. The term "stress protein" as used herein is intended to include such portions and peptides of a stress protein A "stress gene," also known as "heat shock gene", as used herein, refers to a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Stress gene" also includes homologous genes within known stress gene families, such as certain genes within the Hsp70 and Hsp90 stress gene families, even though such homologous genes are not themselves induced by a stressor. Each of the terms stress gene and stress protein as used in the present specification may be inclusive of the other, unless the context indicates otherwise.

The term "vaccine" refers to a substance that elicits an immune response and also confers protective immunity upon a subject.

"Vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids" which refer generally to circular double stranded DNA loops, which, in their vector form are not bound to the chromosome. In the present specification, "plasmid" and "vector" are used interchangeably as the plasmid is the most commonly used form of vector. However, as will be appreciated by those skilled in the art, the invention is intended to include such other forms of expression vectors, such as viral vectors, which serve equivalent functions and which become subsequently known in the art.

As used herein, "specifically binds" means via covalent or hydrogen bonding or electrostatic attraction.

As used herein, an "immune response" or a "detectable response" includes a detectable level of a response that occurs in a subject that has been exposed to a fusion protein of the invention, as described herein, but not in a subject that has not been exposed to a fusion protein of the invention. A "response" that is detected includes but is not limited to an increase in an immune response or an increase in immunogenicity.

A "detectable response" means a response that is at least 0.01%, 0.5%, 1% or more than the response of a subject that has not been exposed to a fusion protein of the invention. A "detectable response" also means a response that is at least 0.5, 1, 2, 3, 4, 5, 10, 20, 30, 40, 50, 60, 70, 80, 90, 100, 1000-fold or more greater than the response of a subject that has not been exposed to a fusion protein of the invention.

As used herein, "immunogenicity" refers to the ability, for example the ability of a fusion protein of the invention to induce humoral and/or cell-mediated immune responses.

As used herein, "immune response" refers to a response made by the immune system of an organism to a substance, which includes but is not limited to foreign or self proteins. There are three general types of "immune response" including, but not limited to mucosal, humoral and cellular "immune responses." A "mucosal immune response" results from the production of secretory IgA (sIgA) antibodies in secretions that bathe all mucosal surfaces of the respiratory tract, gastrointestinal tract and the genitourinary tract and in secretions from all secretory glands (McGhee, J. R. et al., 1983, Annals NY Acad. Sci. 409). These sIgA antibodies act to prevent colonization of pathogens on a mucosal surface (Williams, R. C. et al., Science 177, 697 (1972); McNabb, P. C. et al., Ann. Rev. Microbiol. 35, 477 (1981)) and thus act as a first line of defense to prevent colonization or invasion through a mucosal surface. The production of sIgA can be stimulated either by local immunization of the secretory gland or tissue or by presentation of an antigen to either the gut-associated lymphoid tissue (GALT or Peyer's patches) or the bronchial-associated lymphoid tissue (BALT; Cebra, J. J. et al., Cold Spring Harbor Symp. Quant. Biol. 41, 210 (1976); Bienenstock, J. M., Adv. Exp. Med. Biol. 107, 53 (1978); Weisz-Carrington, P. et al., J. Immunol. 123, 1705 (1979); McCaughan, G. et al., Internal Rev. Physiol 28, 131 (1983)). Membranous microfold cells, otherwise known as M cells, cover the surface of the GALT and BALT and may be associated with other secretory mucosal surfaces. M cells act to sample antigens from the luminal space adjacent to the mucosal surface and transfer such antigens to antigen-presenting cells (dendritic cells and macrophages), which in turn present the antigen to a T lymphocyte (in the case of T-dependent antigens), which process the antigen for presentation to a committed B cell. B cells are then stimulated to proliferate, migrate and ultimately be transformed into an antibody-secreting plasma cell producing IgA against the presented antigen. When the antigen is taken up by M cells overlying the GALT and BALT, a generalized mucosal immunity results with sIgA against the antigen being produced by all secretory tissues in the body (Cebra et al., supra; Bienenstock et al., supra; Weinz-Carrington et al., supra; McCaughan et al., supra). Oral immunization is therefore an important route to stimulate a generalized mucosal immune response and, in addition, leads to local stimulation of a secretory immune response in the oral cavity and in the gastrointestinal tract.

An "immune response" may be measured using techniques known to those of skill in the art. For example, serum, blood or other secretions may be obtained from an organism for which an "immune response" is suspected to be present, and assayed for the presence of the above mentioned immunoglobulins using an enzyme-linked immuno-absorbant assay (ELISA; U.S. Pat. No. 5,951,988; Ausubel et al., Short Protocols in Molecular Biology 3.sup.rd Ed. John Wiley & Sons, Inc. 1995). A statistical test known in the art may be used to determine the difference in measured immunoglobulin levels including, but not limited to ANOVA, Student's T-test, and the like, wherein the P value is at least <0.1, <0.05, <0.01, <0.005, <0.001, and even <0.0001.

An "immune response" may be measured using other techniques such as immunohistochemistry using labeled antibodies which are specific for portions of the immunoglobulins raised during the "immune response." Microscopic data obtained by immunohistochemistry may be quantitated by scanning the immunohistochemically stained tissue sample and quantitating the level of staining using a computer software program known to those of skill in the art including, but not limited to NIH Image (National Institutes of Health, Bethesda, Md.). According to the present invention, a fusion protein of the present invention can be said to stimulate an "immune response" if the quantitative measure of immunohistochemical staining in a subject treated with a fusion protein is statistically different from the measure of immunohistochemical staining detected in a subject not treated with a fusion protein. A statistical test known in the art may be used to determine the difference in measured immunohistochemical staining levels including, but not limited to ANOVA, Student's T-test, and the like, wherein the P value is at least <0.1, <0.05, <0.01, <0.005, <0.001, and even <0.0001.

1. Engineered Fusion Proteins

Provided are fusion proteins comprising an antigen binding domain fused in frame to a modified Mycobacterium tuberculosis heat shock protein 70 (HSP70).

The antigen binding domain may be an engineered antibody or antibody mimetic and may comprise, for example, at least one scFv, at least one Fab fragment, at least one Fv fragment, etc. It may be monovalent or it may be multivalent. In embodiments wherein the engineered antibody is multivalent, it may be bivalent, trivalent, tetravalent, etc. The multivalent antibodies may be monospecific or multispecific, e.g., bispecific, trispecific, tetraspecific, etc. The multivalent antibodies may be in any form, such as a diabody, triabody, tetrabody, etc. In certain embodiments, the engineered antibody is a Tandab. The modified HSP70 may be, for example, a fragment of the natural sequence, a modification of the natural amino acid sequence (e.g., a deletion, addition, and/or substitution) or any combination thereof. The full-length polypeptide sequence of Mycobacterium tuberculosis HSP70 is shown in SEQ ID NO:1.

```
                                          (SEQ ID NO: 1)
MARAVGIDLG  TTNSVVSVLE  GGDPVVVANS  EGSRTTPSIV

AFARNGEVLV  GQPAKNQAVT  NVDRTVRSVK  RHMGSDWSIE

IDGKKYTAPE  ISARILMKLK  RDAEAYLGED  ITDAVITTPA

YFNDAQRQAT  KDAGQIAGLN  VLRIVNEPTA  AALAYGLDKG

EKEQRILVFD  LGGGTFDVSL  LEIGEGVVEV  RATSGDNHLG

GDDWDQRVVD  WLVDKFKGTS  GIDLTKDKMA  MQRLREAAEK

AKIELSSSQS  TSINLPYITV  DADKNPLFLD  EQLTRAEFQR

ITQDLLDRTR  KPFQSVIADT  GISVSEIDHV  VLVGGSTRMP

AVTDLVKELT  GGKEPNKGVN  PDEVVAVGAA  LQAGVLKGEV

KDVLLLDVTP  LSLGIETKGG  VMTRLIERNT  TIPTKRSETF

TTADDNQPSV  QIQVYQGERE  IAAHNKLLGS  FELTGIPPAP

RGIPQIEVTF  DIDANGIVHV  TAKDKGTGKE  NTIRIQEGSG

LSKEDIDRMI  KDAEAHAEED  RKRREEADVR  NQAETLVYQT

EKFVKEQREA  EGGSKVPEDT  LNKVDAAVAE  AKAALGGSDI

SAIKSAMEKL  GQESQALGQA  IYEAAQAASQ  ATGAAHPGGE

PGGAHPGSAD  DVVDAEVVDD  GREAK
```

Further details about antigen binding domains and modified HSP70 sequences which may be incorporated into the subject fusion polypeptides is provided below.

A. Antigen Binding Domains

An antigen binding domain is any peptide sequence that specifically binds to an antigen and can function as part of a fusion protein. The antigen binding domain may be a natural sequence, e.g., an antibody or a fragment thereof, a ficolin, a collectin, etc. The antigen binding domain may be a synthetic sequence, e.g., an engineered antibody, an antibody-like peptide, an antibody mimetic, an aptamer, etc.

The antigen binding domain may specifically bind to an antigen of interest. The antigen binding domain may specifically bind, e.g., to a tumor cell antigen of a cancer to be treated or prevented by the methods of the present invention. Such antigens include, but are not limited to, for example, antigens of a human sarcoma cell or carcinoma cell, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease cell.

The antigen binding domain may specifically bind other antigens, including disease-associated and/or viral antigens. The antigen binding domain may specifically bind diseased and/or virally infected cells expressing antigen on their surface.

Infectious diseases that can be treated or prevented by the methods of the present invention are caused by infectious agents. Such infectious agents or antigens derived therefrom, that may be targeted by the antigen binding domain of the present invention, include, but are not limited to, viruses, bacteria, fungi, and protozoa. The invention is not limited to treating or preventing infectious diseases caused by intracellular pathogens but is intended to include extracellular pathogens as well. Many medically relevant microorganisms have been described extensively in the literature, e.g., see C. G. A Thomas, Medical Microbiology, Bailliere Tindall, Great Britain 1983, the entire contents of which is hereby incorporated by reference.

Infectious viruses of both human and non-human vertebrates, include retroviruses, RNA viruses and DNA viruses expressing antigen. Examples of viral antigens include but are not limited to antigens of: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e., Hepatitis C); Norwalk and related viruses, and astroviruses).

Retroviral antigens that may be targeted include antigens of both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of antigens of RNA viruses that may be bound by an antigen binding domain include, but are not limited to, antigens of the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, ONyong-Nyong virus, Ross river virus, Venezuelan equine encephalitis virus, Western equine encephalitis virus), the genus Flavirus (Mosquito borne yellow fever virus, Dengue virus, Japanese encephalitis virus, St. Louis encephalitis virus, Murray Valley encephalitis virus, West Nile vims, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, ONyong-Nyong virus, Ross river virus, Venezuelan equine encephalitis virus, Western equine encephalitis virus), the genus Flavirus (Mosquito borne yellow fever virus, Dengue virus, Japanese encephalitis virus, St. Louis encephalitis virus, Murray Valley encephalitis virus, West Nile vims, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), ChanBipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronaviridae, including Infectious Bronchitis Virus (IBV), Mouse Hepatitis virus, Human enteric corona virus, and Feline infectious peritonitis (Feline coronavirus).

Illustrative DNA viral antigens include, but are not limited to antigens of the family Poxyiridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D, E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viral antigens may include viral antigens of viruses which do not fit into the above families such as Kuru and Creutzfeldt-Jacob disease viruses and chronic infectious neuropathic agents.

B. Engineered Antibodies

Natural antibodies are themselves dimers, and thus, bivalent. If two hybridoma cells producing different antibodies are artificially fused, some of the antibodies produced by the hybrid hybridoma are composed of two monomers with different specificities. Such bispecific antibodies can also be produced by chemically conjugating two antibodies. Natural antibodies and their bispecific derivatives are relatively large and expensive to produce. The constant domains of mouse antibodies are also a major cause of the human anti-mouse antibody (HAMA) response, which prevents their extensive use as therapeutic agents. They can also give rise to unwanted effects due to their binding of Fc-receptors. For these reasons, molecular immunologists have been concentrating on the production of the much smaller Fab- and Fv-fragments in microorganisms. These smaller fragments are not only much easier to produce, they are also less immunogenic, have no effector functions, and, because of their relatively small size, they are better able to penetrate tissues and tumors. In the case of the Fab-fragments, the constant domains adjacent to the variable domains play a major role in stabilizing the heavy and light chain dimer. Accordingly, while full-length or nearly full length engineered antibodies may comprise the subject fusion polypeptides, smaller, single domain engineered antibodies (that may be multivalent and multispecific) are preferred for use in the fusion polypeptides.

The Fv-fragment is much less stable, and a peptide linker may therefore be introduced between the heavy and light chain variable domains to increase stability. This construct is known as a single chain Fv(scFv)-fragment. A disulfide bond is sometimes introduced between the two domains for extra stability. Thus far, tetravalent scFv-based antibodies have been produced by fusion to extra polymerizing domains such as the streptavidin monomer that forms tetramers, and to amphipathic alpha helices. However, these extra domains can increase the immunogenicity of the tetravalent molecule.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular $V_H$-$V_L$ pairings with formation of a 60 kDa non-covalent scFv dimer "diabody" (Holliger et al., 1993, Proc. Natl. Acad. Sci. USA 90, 6444-6448). The diabody format can also be used for generation of recombinant bispecific antibodies, which are obtained by the noncovalent association of two single-chain fusion products, consisting of the $V_H$ domain from one antibody connected by a short linker to the $V_L$ domain of another antibody. Reducing the linker length still further below three residues can result in the formation of trimers ("triabody," about 90 kDa) or tetramers ("tetrabody," about 120 kDa) (Le Gall et al., 1999, FEBS Letters 453, 164-168). For a review of engineered antibodies, particularly single domain fragments, see Holliger and Hudson, 2005, Nature Biotechnology, 23:1126-1136. All of such engineered antibodies may be used in the fusion polypeptides provided herein.

Other multivalent engineered antibodies that may comprise the subject fusion polypeptides are described in Lu, et al., 2003, J. Immunol. Meth. 279:219-232 (di-diabodies or tetravalent bispecific antibodies); US Published Application 20050079170 (multimeric FAT molecules or ""flexibodies"), and WO99/57150 and Kipriyanov, et al., 1999, J. Mol. Biol. 293:41-56 (tandem diabodies, or "Tandabs").

Any of the above-described multivalent engineered antibodies may be developed by one of skill in the art using routine recombinant DNA techniques, for example as described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison (1985) Science 229:1202-1207; Oi et al. (1986) BioTechniques 4:214; U.S. Pat. No. 5,225,539; Jones et al. (1986) Nature 321:552-525; Verhoeyan et al. (1988) Science 239:1534; Beidler et al. (1988) J. Immunol. 141:4053-4060; and Winter and Milstein, Nature, 349, pp. 293-99 (1991)). Preferably non-human antibodies are "humanized" by linking the non-human antigen binding domain with a human constant domain (e.g., Cabilly et al., U.S. Pat. No. 4,816,567; Morrison et al., Proc. Natl. Acad. Sci. U.S.A., 81, pp. 6851-55 (1984)).

The antigen recognition sites or entire variable regions of the engineered antibodies may be derived from one or more parental antibodies directed against mesothelin. The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al., (Eds.), ANTIBODIES: A LABORATORY MANUAL; Cold Spring Harbor Laboratory; Cold Spring Harbor, N.Y., 1988, Chapter 6.

C. Stress Proteins

Any suitable stress protein (heat shock protein (hsp)) can be used in the fusion polypeptides of the present invention. The stress protein preferably is HSP70, e.g., from *M tuberculosis*.

A "heat shock protein" is encoded by a "heat shock gene" or a stress gene, refers to the protein product of a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Heat shock protein" also includes homologous proteins encoded by genes within known stress gene families, even though such homologous genes are not themselves induced by a stressor. A "heat shock protein fusion" refers to a heat shock protein or portion thereof, linked to an antigen binding domain.

Cells respond to a stressor (typically heat shock treatment) by increasing the expression of a group of genes commonly referred to as stress, or heat shock genes. Heat shock treatment involves exposure of cells or organisms to temperatures that are one to several degrees Celsius above the temperature to which the cells are adapted. In coordination with the induction of such genes, the levels of corresponding stress proteins increase in stressed cells.

For example, a heat shock protein may be C- or N-terminally joined to a antigen-specific antigen binding domain to generate a heat shock protein fusion. A heat shock protein fusion comprising a heat shock protein and an antigen binding domain is capable of stimulating humoral and/or cellular immune responses, including CD8 cytotoxic T cell (CTL) responses, to the antigen.

For example, but not by way of limitation, heat shock proteins which may be used according to the invention include BiP (also referred to as grp78), Hsp10, Hsp20-30, Hsp60 hsp70, hsc70, gp96 (grp94), hsp60, hsp40, and Hsp100-200, Hsp100, Hsp90, and members of the families thereof. Especially preferred heat shock proteins are BiP, gp96, and hsp70, as exemplified below. A particular group of heat shock proteins includes Hsp90, Hsp70, Hsp60, Hsp20-30, further preferably Hsp70 and Hsp60. Most preferred is a member of the hsp70 family.

In bacteria, the predominant stress proteins are proteins with molecular sizes of about 70 and 60 kDa, respectively, that are commonly referred to as Hsp70 and Hsp60, respectively. These and other specific stress proteins and the genes encoding them are discussed further below. In bacteria, Hsp70 and Hsp60 typically represent about 1-3% of cell protein based on the staining pattern using sodium dodecyl sulfate polyacrylamide gel electrophoresis and the stain Coomassie blue, but accumulate to levels as high as 25% under stressful conditions. Stress proteins appear to participate in important cellular processes such as protein synthesis, intracellular trafficking, and assembly and disassembly of protein complexes. It appears that the increased amounts of stress proteins synthesized during stress serve primarily to minimize the consequences of induced protein unfolding. Indeed, the preexposure of cells to mildly stressful conditions that induce the synthesis of stress proteins affords protection to the cells from the deleterious effects of a subsequent more extreme stress.

The major stress proteins appear to be expressed in every organism and tissue type examined so far. Also, it appears that stress proteins represent the most highly conserved group of proteins identified to date. For example, when stress proteins in widely diverse organisms are compared, Hsp90 and Hsp70 exhibit 50% or higher identity at the amino acid level and share many similarities at non-identical positions. It is noted that similar or higher levels of homology exist between different members of a particular stress protein family within species.

The stress proteins, particularly Hsp70, Hsp60, Hsp20-30 and Hsp 10, are among the major determinants recognized by the host immune system in the immune response to infection by Mycobacterium tuberculosis and Mycobacterium leprae. Young, R. A. and Elliott. T. J., Stress Proteins, Infection, And Immune Surveillance, Cell 50:5-8 (1989). Further, some rat arthritogenic T cells recognize Hsp60 epitopes. Van Eden, W. et al., Nature 331:171-173 (1988). However, individuals, including healthy individuals, with no history of mycobacterial infection or autoimmune disease also carry T cells that recognize both bacterial and human Hsp60 epitopes; a considerable fraction of T cells in healthy individuals that are characterized by expression of the gamma-delta T cell receptor recognize both self and foreign stress proteins. O'Brien, R. et al., Cell 57:664-674 (1989). Thus, individuals, even healthy individuals, possess T-cell populations that recognize both foreign and self stress protein epitopes.

This system recognizing stress protein epitopes presumably constitutes an "early defense system" against invading organisms. Murray, P. J. and Young, R. A., J. Bacteriol 174: 4193-6 (1992). The system may be maintained by frequent stimulation by bacteria and viruses. As discussed before, healthy individuals have T cell populations recognizing self stress proteins. Thus, the presence of autoreactive T cells is compatible with normal health and does not cause autoimmune disease; this demonstrates the safety of stress proteins within an individual. The safety of stress proteins is additionally demonstrated by the success and relative safety of BCG (Bacille Calmette Guerin, a strain of *Mycobacterium bovis*) vaccinations, which induce an immune response against stress proteins that is also protective against *Mycobacterium tuberculosis*.

Hsp70 examples include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin: referred to herein as Hsp71), DnaK from *Escherichia coli*, yeast, and other prokaryotes, and BiP and Grp78. Hsp70 is capable of specifically binding ATP as well as unfolded polypeptides and peptides, thereby participating in protein folding and unfolding as well as in the assembly and disassembly of protein complexes.

In particular embodiments, the stress proteins of the present invention are obtained from enterobacteria, mycobacteria (particularly *M leprae, M tuberculosis, M vaccae, M smegmatis* and *M bovis*), *E. coli*, yeast, *Drosophila*, vertebrates, avians, chickens, mammals, rats, mice, primates, or humans.

Naturally occurring or recombinantly derived mutants of heat shock proteins may be used according to the invention, including fragments and modified sequences. For example, but not by way of limitation, the present invention provides for the use of heat shock proteins mutated so as to facilitate their secretion from the cell (for example having mutation or deletion of an element which facilitates endoplasmic reticulum recapture, such as KDEL (SEQ ID NO:14) or its homologues; such mutants are described in PCT Application No. PCT/US96/13233 (WO 97/06685), which is incorporated herein by reference.

In particular embodiments, e.g., in cases involving chemical conjugates between a stress protein and an engineered antibody, the stress proteins used are isolated stress proteins, which means that the stress proteins have been selected and separated from the host cell in which they were produced. Such isolation can be carried out as described herein and using routine methods of protein isolation known in the art. The stress proteins may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance the increased biological activity of the stress protein. Due to code degeneracy, for example, there may be considerable variation in nucleotide sequences encoding the same amino acid sequence. Portions of stress proteins or peptides obtained from stress proteins may be used in the fusion polypeptides, provided such portions or peptides include the epitopes involved with enhancing the immune response. Portions of stress proteins may be obtained by fragmentation using proteinases, or by recombinant methods, such as the expression of only part of a stress protein-encoding nucleotide sequence (either alone or fused with another protein-encoding nucleic acid sequence). Peptides may also be produced by such methods, or by chemical synthesis. The stress proteins may include mutations introduced at particular loci by a variety of known techniques. See, e.g., Sambrook et al., Molecular Cloning: A Laboratory Manual. 2d Ed., Cold Spring Harbor Laboratory Press (1989); Drinkwater and Klinedinst Proc. Natl. Acad. Sci. USA 83:3402-3406 (1986); Liao and Wise, Gene 88:107-111 (1990): Horwitz et al., Genome 3:112-117 (1989).

The pharmaceutical compositions provided herein may have individual amino acid residues that are modified by oxidation or reduction. Furthermore, various substitutions, deletions, or additions may be made to the amino acid or nucleic acid sequences, the net effect of which is to retain or further enhance the increased biological activity of the heat shock protein. Due to codon degeneracy, for example, there may be considerable variation in nucleotide sequences encoding the same amino acid sequence.

The term "heat shock protein" is intended to encompass fragments of heat shock proteins obtained from heat shock proteins, provided such fragments include the epitopes involved with enhancing the immune response to mesothelin. Fragments of heat shock proteins may be obtained using proteinases, or by recombinant methods, such as the expression of only part of a stress protein-encoding nucleotide sequence (either alone or fused with another protein-encoding nucleic acid sequence). The heat shock proteins may include mutations introduced at particular loci by a variety of known techniques to enhance its effect on the immune system. See, e.g., Sambrook et al., Molecular Cloning: A Laboratory Manual, 2d Ed., Cold Spring Harbor Laboratory Press (1989); Drinkwater and Klinedinst Proc. Natl. Acad. Sci. USA 83:3402-3406 (1986); Liao and Wise, Gene 88:107-111 (1990); Horwitz et al., Genome 3:112-117 (1989).

In particular embodiments, the heat shock proteins used in the present invention are isolated heat shock proteins, which means that the heat shock proteins have been selected and separated from the host cell in which they were produced. Such isolation can be carried out as described herein and using routine methods of protein isolation known in the art. Maniatis et al., Molecular Cloning, A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182, Academic Press, Inc., San Diego, Calif. (1990).

C. Fusion Protein Embodiments

One aspect of the invention relates to a fusion protein comprising an antigen binding domain fused in frame to a fragment of Mycobacterium tuberculosis heat shock protein 70 (HSP70) of less than 200 amino acids, wherein the HSP70 fragment comprises a minimal HSP70 sequence. The HSP70 fragment may comprise, consist essentially of, or consist of the minimal HSP sequence.

The minimal HSP70 sequence refers to a fragment of HSP70 that provides all of the biological functions desired in the fusion proteins of the present invention. In some embodiments, the minimal HSP70 sequence is at least 40 amino acids in length, e.g., at least about 40, 50, 60, 70, 80, 90, 100, 110, or 120 amino acids in length. In some embodiments, the minimal HSP70 sequence is less than 400 amino acids in length, e.g., less than about 400, 350, 300, 250, 200, 190, 180, 170, 160, 150, 140, or 130 amino acids in length. In certain embodiments, the minimal HSP70 sequence comprises, consists essentially of, or consists of the fragment from about amino acid residues 368 (e.g., plus or minus 20, 15, 10, or 5 residues) to about amino acid residue495 (e.g., plus or minus 20, 15, 10, or 5 residues) ofM. tuberculosis HSP70 (SEQ ID NO:1). In some embodiments, the minimal HSP70 region is about amino acid residues 368-495 or about 368-479 of SEQ ID NO:1.

In one embodiment, the fusion protein comprising the minimal HSP sequence comprises, consists essentially of, or consist of the amino acid sequence of SEQ ID NO:3. The underline indicates the linker between the $V_H$ and $V_L$ domains of the scFv, the italics indicates the linker between the scFv and the HSP70, and the bold indicates the CD94 domain.

```
                                          (SEQ ID NO: 3)
QVQLQQSGPG LVTPSQTLSL TCAISGDSVS SNSATWNWIR

QSPSRGLEWL GRTYYRSKWY NDYAVSVKSR MSINPDTSKN

QFSLQLNSVT PEDTAVYYCA RGMMTYYYGM DVWGQGTTVT

VSSGILGSGG GGSGGGGSGG GGSQPVLTQS SSLSASPGAS

ASLTCTLRSG INVGPYRIYW YQQKPGSPPQ YLLNYKSDSD

KQQGSGVPSR FSGSKDASAN AGVLLISGLR SEDEADYYCM

IWHSSAAVFG GGTQLTVLGG GGSGGGGSGG GGSVTPLSLG

IETKGGFMTR LIERNTTIPT KRSETFTTAD DNQPSVQIQV

YQGEREIAAR NKLLGSFELT GIPPAPRGIP QIEVTFDIDA

NGIVHVTAKD KGTGKENTIR IQEGSGLSKE DIDRMIKDAE A
```

In some embodiments, the minimal HSP sequence comprises a modified CD94 domain, i.e., the amino acid sequence of the CD94 domain is modified. As used herein, the term "CD94 domain" refers to amino acid residues 422-435 of Mbt HSP70 (SEQ ID NO:1) having the sequence AAHNKLLGSFELTG (SEQ ID NO:15) or the equivalent sequence in other HSP70 proteins.

In some embodiments, the modified CD94 domain consists of an amino acid sequence selected from:

AAHNNLLGSFELTG (SEQ ID NO: 16)

AAHNNLLGRFELTG (SEQ ID NO: 17)

AAHNNLLGRFELSG (SEQ ID NO: 18)

TKENNLLGRFELSG (SEQ ID NO: 19)

TRDNNLLGRFELSG (SEQ ID NO: 20)

In certain embodiments, the modified CD94 domain consists of the amino acid sequence TKENNLLGRFELSG (SEQ ID NO:19). In one embodiment, the fusion protein comprising the minimal HSP sequence with the CD94 domain sequence TKENNLLGRFELSG (SEQ ID NO:19) comprises, consists essentially of, or consist of the amino acid sequence of SEQ ID NO:5.

```
                                              (SEQ ID NO: 5)
QVQLQQSGPG LVTPSQTLSL TCAISGDSVS SNSATWNWIR

QSPSRGLEWL GRTYYRSKWY NDYAVSVKSR MSINPDTSKN

QFSLQLNSVT PEDTAVYYCA RGMMTYYYGM DVWGQGTTVT

VSSGILGSGG GGSGGGGSGG GGSQPVLTQS SSLSASPGAS

ASLTCTLRSG INVGPYRIYW YQQKPGSPPQ YLLNYKSDSD

KQQGSGVPSR FSGSKDASAN AGVLLISGLR SEDEADYYCM

IWHSSAAVFG GGTQLTVLGG GGSGGGGSGG GGSVTPLSLG

IETKGGFMTR LIERNTTIPT KRSETFTTAD DNQPSVQIQV

YQGEREITKE NNLLGRFELS GIPPAPRGIP QIEVTFDIDA

NGIVHVTAKD KGTGKENTIR IQEGSGLSKE DIDRMIKDAE A
```

In certain embodiments, the modified CD94 domain consists of the amino acid sequence TKDNNLLGRFELSG (SEQ ID NO:35). In one embodiment, the fusion protein comprising the minimal HSP sequence with the CD94 domain sequence TKDNNLLGRFELSG (SEQ ID NO:35) comprises, consists essentially of, or consist of the amino acid sequence of SEQ ID NO:7.

```
                                              (SEQ ID NO: 7)
QVQLQQSGPG LVTPSQTLSL TCAISGDSVS SNSATWNWIR

QSPSRGLEWL GRTYYRSKWY NDYAVSVKSR MSINPDTSKN

QFSLQLNSVT PEDTAVYYCA RGMMTYYYGM DVWGQGTTVT

VSSGILGSGG GGSGGGGSGG GGSQPVLTQS SSLSASPGAS

ASLTCTLRSG INVGPYRIYW YQQKPGSPPQ YLLNYKSDSD

KQQGSGVPSR FSGSKDASAN AGVLLISGLR SEDEADYYCM

IWHSSAAVFG GGTQLTVLGG GGSGGGGSGG GGSVTPLSLG

IETKGGFMTR LIERNTTIPT KRSETFTTAD DNQPSVQIQV

YQGEREITKD NNLLGRFELS GIPPAPRGIP QIEVTFDIDA

NGIVHVTAKD KGTGKENTIR IQEGSGLSKE DIDRMIKDAE A
```

In certain embodiments, the minimal HSP70 sequence may contain one or more amino acid additions, deletions or substitutions that enhance the effectiveness of the fusion protein of the invention. In one embodiment, the minimal HSP70 sequence comprises a V381F substitution (numbering based on SEQ ID NO:1), which decreases the peptide binding activity of HSP70, thereby minimizing non-specific antigen delivery.

In some embodiments, the fusion protein further comprises a linker between the antibody binding domain and the HSP70 fragment. In certain embodiments, linker comprises, consists essentially of, or consists of an amino acid sequence selected from the group consisting of GGSSRSS (SEQ ID NO:21), (GGGSGGG)$_4$ (SEQ ID NO:22), GGGGSGGGGSGGGGS (SEQ ID NO:23), GGSSRSSSSGGGGSGGGG (SEQ ID NO:24), and GGSSESSSSGGGGSGGGG (SEQ ID NO:25).

In certain embodiments, the linker is GGSSRSSSSGGGGSGGGG (SEQ ID NO:24). In one embodiment, the fusion protein comprising the minimal HSP70 sequence and the linker GGSSRSSSSGGGGSGGGG (SEQ ID NO:24) comprises, consists essentially of, or consist of the amino acid sequence of SEQ ID NO:9.

```
                                              (SEQ ID NO: 9)
QVQLQQSGPG LVTPSQTLSL TCAISGDSVS SNSATWNWIR

QSPSRGLEWL GRTYYRSKWY NDYAVSVKSR MSINPDTSKN

QFSLQLNSVT PEDTAVYYCA RGMMTYYYGM DVWGQGTTVT

VSSGILGSGG GGSGGGGSGG GGSQPVLTQS SSLSASPGAS

ASLTCTLRSG INVGPYRIYW YQQKPGSPPQ YLLNYKSDSD

KQQGSGVPSR FSGSKDASAN AGVLLISGLR SEDEADYYCM

IWHSSAAVFG GGTQLTVLGG SSRSSSSGGG GSGGGGVTPL

SLGIETKGGF MTRLIERNTT IPTKRSETFT TADDNQPSVQ

IQVYQGEREI TKENNLLGRF ELSGIPPAPR GIPQIEVTFD

IDANGIVHVT AKDKGTGKEN TIRIQEGSGL SKEDIDRMIK DAEA
```

In certain embodiments, the linker is GGSSESSSSGGGGSGGGG (SEQ ID NO:25). In one embodiment, the fusion protein comprising the minimal HSP70 sequence and the linker GGSSESSSSGGGGSGGGG (SEQ ID NO:25) comprises, consists essentially of, or consist of the amino acid sequence of SEQ ID NO:11.

```
                                              (SEQ ID NO: 11)
QVQLQQSGPG LVTPSQTLSL TCAISGDSVS SNSATWNWIR

QSPSRGLEWL GRTYYRSKWY NDYAVSVKSR MSINPDTSKN

QFSLQLNSVT PEDTAVYYCA RGMMTYYYGM DVWGQGTTVT

VSSGILGSGG GGSGGGGSGG GGSQPVLTQS SSLSASPGAS

ASLICTLRSG INVGPYRIYW YQQKPGSPPQ YLLNYKSDSD

KQQGSGVPSR FSGSKDASAN AGVLLISGLR SEDEADYYCM

IWHSSAAVFG GGTQLTVLGG SSESSSSGGG GSGGGGVTPL

SLGIETKGGF MTRLIERNTT IPTKRSETFT TADDNQPSVQ

IQVYQGEREI TKENNLLGRF ELSGIPPAPR GIPQIEVTFD

IDANGIVHVT AKDKGTGKEN TIRIQEGSGL SKEDIDRMIK DAEA
```

A further aspect of the invention relates to a fusion protein comprising an antigen binding domain fused in frame to a fragment of Mycobacterium tuberculosis heat shock protein 70 (HSP70) of at least 100 amino acids and comprising no more than amino acids 1-495 of SEQ ID NO:1. This fragment does not comprise the C-terminal lid sequence, the deletion providing enhanced biological activity for the fusion proteins of the invention. The HSP70 lid deletion fragment of this aspect of the invention has a maximum length of 495 amino acid residues starting with amino acid 1 of the natural *M tuberculosis* amino acid sequence. The HSP lid deletion fragment may have a length of less than about 495, 490, 480, 470, 460, 450, 425, 400, 375, 350, 325, or 300 amino acid residues. The HSP fragment may have a length of at least about 100, 125, 150, 175, 200, 225, 250, 275, or 300 amino acid residues.

In certain embodiments, the HSP70 lid deletion fragment may contain one or more amino acid additions, deletions or substitutions that enhance the effectiveness of the fusion protein of the invention. In one embodiment, the HSP70 lid deletion fragment comprises one or more of the modifications (a) F176A orb) R318A (in the LPS binding site in subdomain II to alter LPS binding) or c) V381F (in the peptide binding domain to alter peptide binding) in any combination (numbering based on SEQ ID NO:1). In one embodiment, the fusion protein comprising the HSP70 lid deletion fragment and additional modifications comprises, consists essentially of, or consists of the amino acid sequence of SEQ ID NOS:12, 13, or 31.

```
                                                          (SEQ ID NO: 12)
QVQLQQSGPG LVTPSQTLSL TCAISGDSVS SNSATWNWIR QSPSRGLEWL

GRTYYRSKWY NDYAVSVKSR MSINPDTSKN QFSLQLNSVT PEDTAVYYCA

RGMMTYYYGM DVWGQGTTVT VSSGILGSGG GGSGGGGSGG GGSQPVLTQS

SSLSASPGAS ASLTCTLRSG INVGPYRIYW YQQKPGSPPQ YLLNYKSDSD

KQQGSGVPSR FSGSKDASAN AGVLLISGLR SEDEADYYCM IWHSSAAVFG

GGTQLTVLGG SSRSSSSGGG GSGGGGMARA VGIDLGTTNS VVSVLEGGDP

VVVANSEGSR TTPSIVAFAR NGEVLVGQPA KNQAVINVDR TVRSVRRHMG

SDWSIEIDGK KYTAPEISAR ILMKLKRDAE AYLGEDITDA VITTPAYFND

AQRQATKDAG QIAGLNVLRI VNEPTAAALA YGLDKGEKEQ RILVFDLGGG

TFDVSLLEIG EGVVEVRATS GDNHLGGDDW DQRVVDWLVD KFKGTSGIDL

TKDKMAMQRL REAAEKAKIE LSSSQSTSIN LPYITVDADK NPLFLDEQLT

RAEFQRITQD LLDRTRKPFQ SVIADTGISV SEIDHVVLVG GSTAMPAVTD

LVKELTGGKE PNKGVNPDEV VAVGAALQAG VLKGEVKDVL LLDVTPLSLG

IETKGGFMTR LIERNTTIPT KRSETFTTAD DNQPSVQIQV YQGEREITKE

NNLLGRFELS GIPPAPRGIP QIEVTFDIDA NGIVHVTAKD KGTGKENTIR

IQEGSGLSKE DIDRMIKDAE A
                                                          (SEQ ID NO: 13)
QVQLQQSGPG LVTPSQTLSL TCAISGDSVS SNSATWNWIR QSPSRGLEWL

GRTYYRSKWY NDYAVSVKSR MSINPDTSKN QFSLQLNSVT PEDTAVYYCA

RGMMTYYYGM DVWGQGTTVT VSSGILGSGG GGSGGGGSGG GGSQPVLTQS

SSLSASPGAS ASLTCTLRSG INVGPYRIYW YQQKPGSPPQ YLLNYKSDSD

KQQGSGVPSR FSGSKDASAN AGVLLISGLR SEDEADYYCM IWHSSAAVFG

GGTQLTVLGG SSESSSSGGG GSGGGGMARA VGIDLGTTNS VVSVLEGGDP

VVVANSEGSR TTPSIVAFAR NGEVLVGQPA KNQAVTNVDR TVRSVKRHMG

SDWSIEIDGK KYTAPEISAR ILMKLKRDAE AYLGEDITDA VITTPAYFND

AQRQATKDAG QIAGLNVLRI VNEPTAAALA YGLDKGEKEQ RILVFDLGGG

TFDVSLLEIG EGVVEVRATS GDNHLGGDDW DQRVVDWLVD KFKGTSGIDL

TKDKMAMQRL REAAEKAKIE LSSSQSTSIN LPYITVDADK NPLFLDEQLT

RAEFQRITQD LLDRTRKPFQ SVIADTGISV SEIDHVVLVG GSTAMPAVTD

LVKELTGGKE PNKGVNPDEV VAVGAALQAG VLKGEVKDVL LLDVTPLSLG
```

```
IETKGGFMTR LIERNTTIPT KRSETFTTAD DNQPSVQIQV YQGEREITKE
NNLLGRFELS GIPPAPRGIP QIEVTFDIDA NGIVHVTAKD KGTGKENTIR
IQEGSGLSKE DIDRMIKDAE A (SEQ ID NO: 31)
QVQLQQSGPG LVTPSQTLSL TCAISGDSVS SNSATWNWIR QSPSRGLEWL

GRTYYRSKWY NDYAVSVKSR MSINPDTSKN QFSLQLNSVT PEDTAVYYCA

RGMMTYYYGM DVWGQGTTVT VSSGILGSGG GGSGGGGSGG GGSQPVLTQS

SSLSASPGAS ASLTCTLRSG INVGPYRIYW YQQKPGSPPQ YLLNYKSDSD

KQQGSGVPSR FSGSKDASAN AGVLLISGLR SEDEADYYCM IWHSSAAVFG

GGTQLTVLGG SSESSSSGGG GSGGGGMARA VGIDLGTTNS VVSVLEGGDP

VVVANSEGSR TTPSIVAFAR NGEVLVGQPA KNQAVTNVDR TVRSVKRHMG

SDWSIEIDGK KYTAPEISAR ILMKLKRDAE AYLGEDITDA VITTPAYFND

AQRQATKDAG QIAGLNVLRI VNEPTAAALA YGLDKGEKEQ RILVFDLGGG

TFDVSLLEIG EGVVEVRATS GDNHLGGDDW DQRVVDWLVD KFKGTSGIDL

TKDKMAMQRL REAAEKAKIE LSSSQSTSIN LPYITVDADK NPLFLDEQLT

RAEFQRITQD LLDRTRKPFQ SVIADTGISV SEIDHVVLVG GSTAMPAVTD

LVKELTGGKE PNKGVNPDEV VAVGAALQAG VLKGEVKDVL LLDVTPLSLG

IETKGGFMTR LIERNTTIPT KRSETFTTAD DNQPSVQIQV YQGEREITKE
NNLLGRFELS GIPPAPRGIP QIEVTFDIDA NGIVHVTAKD KGTGKENTIR
IQEGSGLSKE DIDRMIKDAE A
```

In some embodiments, in any of the modified HSP70, including the sequence of SEQ ID NO:31, the Treg domain (amino acid residues 141-155) may be modified, e.g., to one of VLRIVNEPMAAALAY (SEQ ID NO:32), VLRIVNEPTAAALAF (SEQ ID NO:33), or VLRIVNEPMAAALAF (SEQ ID NO:34).

In some embodiments, the HSP70 lid deletion fragment further comprises a modified CD94 domain as described above.

In some embodiments, the fusion protein comprising the HSP70 lid deletion fragment further comprises a linker as described above.

In some embodiments, the HSP70 lid deletion fragment further comprises a modification to the Treg domain. The Treg domain of HSP70 is well known and corresponds to amino acid residues 141-155 of SEQ ID NO:1 or the equivalent domain from other HSP70 proteins. The Treg domain may be modified, for example, by replacing the domain from the M tuberculosis sequence with a Treg domain from another HSP70, e.g., a human HSP70 protein, or deleting and/or substituting one or more amino acid residues, e.g., one or more of the residues that are conserved among members of the HSP70 family.

An additional aspect of the invention relates to a fusion protein comprising an antigen binding domain fused in frame to a fragment of Mycobacterium tuberculosis heat shock protein 70 (HSP70) comprising, consisting essentially of, or consisting of the amino acid sequence of SEQ ID NO:26 (VIC-008 sequence from provisional).

```
                                                            (SEQ ID NO: 26)
           MARAVGIDLG TTNSVVSVLE GGDPVVVANS EGSRTTPSIV AFARNGEVLV

GQPAKNQAVT NVDRTVRSVK RHMGSDWSIE IDGKKYTAPE ISARILMKLK

RDAEAYLGED ITDAVITTPA YFNDAQRQAT KDAGQIAGLN VLRIVNEPTA

AALAYGLDKG EKEQRILVFD LGGGTFDVSL LEIGEGVVEV RATSGDNHLG

GDDWDQRVVD WLVDKFKGTS GIDLTKDKMA MQRLREAAEK AKIELSSSQS

TSINLPYITV DADKNPLFLD EQLTRAEFQR ITQDLLDRTR KPFQSVIADT

GISVSEIDHV VLVGGSTRMP AVTDLVKELT GGKEPNKGVN PDEVVAVGAA

LQAGVLKGEV KDVLLLDVTP LSLGIETKGG FMTRLIERNT TIPTKRSETF

TTADDNQPSV QIQVYQGERE IAAHNKLLGS FELTGIPPAP RGIPQIEVTF
```

-continued

```
DIDANGIVHV TAKDKGTGKE NTIRIQEGSG LSKEDIDRMI KDAEAHAEED

RKRREEADVR NQAETLVYQT EKFVKEQREA EGGSKVPEDT LNKVDAAVAE

AKAALGGSDI SAIKSAMEKL GQESQALGQA IYEAAQAASQ ATGAAHPGGE

PGGAHPGSAD DVVDAEVVDD GREAK
```

The modified HSP70 sequence of SEQ ID NO:26 may be part of a fusion protein comprising, consisting essentially of, or consisting of SEQ ID NO:27

```
                                              (SEQ ID NO: 27)
QVQLQQSGPG LVTPSQTLSL TCAISGDSVS SNSATWNWIR QSPSRGLEWL

GRTYYRSKWY NDYAVSVKSR MSINPDTSKN QFSLQLNSVT PEDTAVYYCA

RGMMTYYYGM DVWGQGTTVT VSSGILGSGG GGSGGGGSGG GGSQPVLTQS

SSLSASPGAS ASLTCTLRSG INVGPYRIYW YQQKPGSPPQ YLLNYKSDSD

KQQGSGVPSR FSGSKDASAN AGVLLISGLR SEDEADYYCM IWHSSAAVFG

GGTQLTVLGG GGSGGGGSGG GGSGGMARAV GIDLGTTNSV VSVLEGGDPV

VVANSEGSRT TPSIVAFARN GEVLVGQPAK NQAVTNVDRT VRSVKRHMGS

DWSIEIDGKK YTAPEISARI LMKLKRDAEA YLGEDITDAV ITTPAYFNDA

QRQATKDAGQ IAGLNVLRIV NEPTAAALAY GLDKGEKEQR ILVFDLGGGT

FDVSLLEIGE GVVEVRATSG DNHLGGDDWD QRVVDWLVDK FKGTSGIDLT

KDKMAMQRLR EAAEKAKIEL SSSQSTSINL PYITVDADKN PLFLDEQLTR

AEFQRITQDL LDRTRKPFQS VIADTGISVS EIDHVVLVGG STRMPAVTDL

VKELTGGKEP NKGVNPDEVV AVGAALQAGV LKGEVKDVLL LDVTPLSLGI

ETKGGFMTRL IERNTTIPTK RSETFTTADD NQPSVQIQVY QGEREIAAHN

KLLGSFELTG IPPAPRGIPQ IEVTFDIDAN GIVHVTAKDK GTGKENTIRI

QEGSGLSKED IDRMIKDAEA HAEEDRKRRE EADVRNQAET LVYQTEKFVK

EQREAEGGSK VPEDTLNKVD AAVAEAKAAL GGSDISAIKS AMEKLGQESQ

ALGQAIYEAA QAASQATGAA HPGGEPGGAH PGSADDVVDA EVVDDGREAK
```

The modified HSP70 of SEQ ID NO:26 or SEQ ID NO:27 may comprise one or more further modifications as described above, e.g., the CD94 domain and/or Treg domain and or LPS domain and/or peptide binding domain modifications and/or linker sequences described above.

Another aspect of the invention relates to a fusion protein comprising an antigen binding domain fused in frame to a chimeric M tuberculosis HSP70, wherein the chimeric HSP70 comprises a backbone of a human HSP70 amino acid sequence wherein the beta sheet structure (e.g., about residue 367 to about residue 479 (e.g., plus or minus 20, 15, 10, or 5 residues)) (numbering based on SEQ ID NO:29)) is substituted with the beta sheet structure (e.g., about residue 395 to about residue 541 (e.g., plus or minus 20, 15, 10, or 5 residues)) ofM tuberculosis HSP70 (numbering based on SEQ ID NO:1).

```
                                              (SEQ ID NO: 29)
MAKAAAIGID LGTTYSCVGV FQHGKVEIIA NDQGNRTTPS YVAFTDTERL

IGDAAKNQVA LNPQNTVFDA KRLIGRKFGD PVVQSDMKHW PFQVINDGDK

PKVQVSYKGD TKAFYPEEIS SMVLTKMKEI AEAYLGYPVT NAVITVPAYF

NDSQRQATKD AGVIAGLNVL RIINEPTAAA IAYGLDRTGK GERNVLIFDL

GGGTFDVSIL TIDDGIFEVK ATAGDTHLGG EDFDNRLVNH FVEEFKRKHK

KDISQNKRAV RRLRTACERA KRTLSSSTQA SLEIDSLFEG IDFYTSITRA

RFEELCSDLF RSTLEPVEKA LRDAKLDKAQ IHDLVLVGGS TRIPKVQKLL
```

-continued

```
QDFFNGRDLN KSINPDEAVA YGAAVQAAIL MGDKSENVQD LLLLDVAPLS

LGLETAGGVM TALIKRNSTI PTKQTQIFTT YSDNQPGVLI QVYEGERAMT

KDNNLLGRFE LSGIPPAPRG VPQIEVTFDI DANGILNVTA TDKSTGKANK

ITITNDKGRL SKEEIERMVQ EAEKYKAEDE VQRERVSAKN ALESYAFNMK

SAVEDEGLKG KISEADKKKV LDKCQEVISW LDANTLAEKD EFEHKRKELE

QVCNPIISGL YQGAGGPGPG GFGAQGPKGG SGSGPTIEEV D
```

The human HSP70 backbone may be from any known human HSP70 family member, e.g., HSP70-1a, HSP70-1b, HSP70-1t, HSP70-2, HSP70-5, HSP70-6, HSC70, and HSP70-9.

All of the modified HSP70 proteins described above may be fused to an antigen binding domain, which may be an engineered antibody or fragment thereof. In some embodiments, the antigen binding domain is an scFv.

The antigen binding domain may bind any antigen of interest. In some embodiments, the antigen is a cancer antigen. In some embodiments, the antigen binding domain binds specifically to mesothelin, e.g., a scFv that binds specifically to mesothelin. Examples of mesothelin antibodies include those disclosed in WO 2009/068204, incorporated by reference in its entirety. In one embodiment the scFv that binds specifically to mesothelin comprises, consists essentially of, or consists of the amino acid sequence of SEQ ID NO:30.

```
                                          (SEQ ID NO: 30)
QVQLQQSGPG LVTPSQTLSL TCAISGDSVS SNSATWNWIR

QSPSRGLEWL GRTYYRSKWY NDYAVSVKSR MSINPDTSKN

QFSLQLNSVT PEDTAVYYCA RGMMTYYYGM DVWGQGTIVT

VSSGILGSGG GGSGGGGSGG GGSQPVLTQS SSLSASPGAS

ASLTCTLRSG INVGPYRIYW YQQKPGSPPQ YLLNYKSDSD

KQQGSGVPSR FSGSKDASAN AGVLLISGLR SEDEADYYCM

IWHSSAAVFG GGTQLTVL
```

The fusion proteins of the invention may further comprise a leader sequence on the N-terminus, e.g., such that the fusion protein is secreted from the host cell in which it is expressed. The leader sequence may be any suitable leader sequence, e.g., from a secreted protein that is native to the host. In some embodiments, the leader sequence is a plant protein leader sequence, e.g., from Arabidopsis extensin, Nicotiana extensin, barley alpha amylase, or PR1A.

The fusion proteins of the present invention encompass variants of any of the sequences disclosed above, e.g., sequences that are at least about 80%, 85%, 90%, 91%, 92%, 93%, 94%, 95%, 96%, 97%, 98%, or 99% identical to one of the sequences disclosed above.

A further aspect of the invention relates to a composition comprising one or more of the fusion proteins of the present invention. In some embodiments, the composition is a pharmaceutical composition comprising an effective amount of the fusion protein of the invention and a pharmaceutically acceptable carrier. In some embodiments, the composition is an immunogenic composition or vaccine comprising the fusion protein of the invention.

2. Methods of Making the Fusion Proteins

Provided also are compositions and methods for making fusion proteins according to the invention. Any of the fusion proteins described herein can be produced by recombinant means. For example, a nucleic acid encoding a HSP70 protein can be joined to either end of a nucleic acid sequence encoding an antigen binding domain, such that the protein-coding sequences are sharing a common translational reading frame and can be expressed as a fusion protein including, for example, the antigen binding domain and the HSP70 protein.

The combined sequence is inserted into a suitable vector chosen based on the expression features desired and the nature of the host cell. In the examples provided hereinafter, the nucleic acid sequences are assembled in a vector suitable for protein expression in CHO cells. Following expression in the chosen host cell, the fusion protein can be purified by routine biochemical separation techniques or by immunoaffinity methods using an antibody to one of the components of the fusion protein. Alternatively, the selected vector can add a tag to the fusion protein sequence, e.g., an oligohistidine tag, permitting expression of a tagged fusion protein that can be purified by affinity methods using an antibody or other material having an appropriately high affinity for the tag. Sambrook et al., Molecular Cloning: A Laboratory Manual, 2d Ed., Cold Spring Harbor Laboratory Press (1989); Deutscher, M. Guide to Protein Purification Methods Enzymology, vol. 182. Academic Press, Inc. San Diego, Calif. (1990). If a vector suitable for expression in mammalian cells is used, e.g., one of the vectors discussed below, the fusion protein can be expressed and purified from mammalian cells. Alternatively, the mammalian expression vector (including fusion protein-coding sequences) can be administered to a subject to direct expression of a fusion protein according to the method of the invention in the subject's cells. If a vector suitable for expression in bacteria, yeast, insect cells, or the like is used, the fusion protein can be expressed and purified from cultures of the cells. If a vector suitable for expression in plants is used, the fusion protein can be expressed and purified from transgenic plants expressing the protein. A nucleic acid encoding the fusion protein of the invention can also be produced chemically and then inserted into a suitable vector for fusion protein production and purification or administration to a subject. Finally, a fusion protein can also be prepared chemically.

Techniques for making fusion genes are well known in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, Current Protocols in Molecular Biology, eds. Ausubel et al., John Wiley & Sons: 1992). Accordingly, provided is an isolated nucleic acid comprising a fusion gene of a gene encoding at least one engineered antibody and a gene encoding at least one stress protein. The isolated nucleic acid may be codon-optimized to maximize expression in a host cell.

The nucleic acid may be provided in a vector comprising a nucleotide sequence encoding an engineered fusion protein according to the invention, and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered. Such vectors may be administered in any biologically effective carrier, e.g., any formulation or composition capable of effectively transfecting cells either ex vivo or in vivo with genetic material encoding a chimeric polypeptide. Approaches include insertion of the nucleic acid into viral vectors including recombinant retroviruses, adenoviruses, adeno-associated viruses, human immunodeficiency viruses, and herpes simplex viruses-1, or recombinant bacterial or eukaryotic plasmids. Viral vectors may be used to transfect cells directly; plasmid DNA may be delivered alone with the help of, for example, cationic liposomes (lipofectin) or derivatized (e.g., antibody conjugated), polylysine conjugates, gramicidin S, artificial viral envelopes or other such intracellular carriers. Nucleic acids may also be directly injected. Alternatively, calcium phosphate precipitation may be carried out to facilitate entry of a nucleic acid into a cell.

The subject nucleic acids may be used to cause expression and over-expression of a fusion protein of the invention in cells propagated in culture, e.g., to produce fusion proteins or polypeptides.

Provided also is a host cell transfected with a recombinant gene in order to express an engineered fusion protein. The host cell may be any prokaryotic or eukaryotic cell. For example, a HSP70 fusion may be expressed in bacterial cells, such as E. coli, insect cells (baculovirus), yeast, insect, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the fusion polypeptide will be known to those in the art.

A cell culture includes host cells, media and other byproducts. Suitable media for cell culture are well known in the art. A fusion polypeptide may be secreted and isolated from a mixture of cells and medium comprising the polypeptide. Alternatively, a fusion polypeptide may be retained cytoplasmically and the cells harvested, lysed and the protein isolated. A fusion polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a fusion.

Thus, a nucleotide sequence encoding all or part of a fusion protein of the invention may be used to produce a recombinant form of a protein via microbial or eukaryotic cellular processes. Ligating the sequence into a polynucleotide construct, such as an expression vector, and transforming or transfecting into hosts, either eukaryotic (yeast, avian, insect, plant, or mammalian) or prokaryotic (bacterial cells), are standard procedures. Similar procedures, or modifications thereof, may be employed to prepare recombinant fusion polypeptides by microbial means or tissue-culture technology in accord with the subject invention.

Expression vehicles for production of a recombinant protein include plasmids and other vectors. For instance, suitable vectors for the expression of a fusion polypeptide include plasmids of the types: pBR322-derived plasmids, pEMBL-derived plasmids, pEX-derived plasmids, pBTac-derived plasmids, and pUC-derived plasmids for expression in prokaryotic cells, such as E. coli.

In another embodiment, the nucleic acid is a fusion protein operably linked to a bacterial promoter, e.g., the anaerobic E. coli, NirB promoter or the E. coli lipoprotein lip promoter, described, e.g., in Inouye et al. (1985) Nucl. Acids Res. 13:3101; Salmonella pagc promoter (Miller et al., supra), Shigella ent promoter (Schmitt and Payne, J. Bacteriol. 173:816 (1991)), the tet promoter on Tn10 (Miller et al., supra), or the ctx promoter of Vibrio cholera. Any other promoter can be used. The bacterial promoter can be a constitutive promoter or an inducible promoter. An exemplary inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB are known in the art and are described, e.g., in the following references: Headley, V. et al. (1997) Infection & Immunity 65:818; Ochsner, U. A. et al. (1995) Journal of Bacteriology 177: 7194; Hunt, M. D. et al. (1994) Journal of Bacteriology 176:3944; Svinarich, D. M. and S. Palchaudhuri. (1992) Journal of Diarrhoeal Diseases Research 10:139; Prince, R. W. et al. (1991) Molecular Microbiology 5:2823; Goldberg, M. B. et al. (1990) Journal of Bacteriology 172:6863; de Lorenzo, V. et al. (1987) Journal of Bacteriology 169:2624; and Hantke, K (1981) Molecular & General Genetics 182: 288.

A plasmid preferably comprises sequences required for appropriate transcription of the nucleic acid in bacteria, e.g., a transcription termination signal. The vector can further comprise sequences encoding factors allowing for the selection of bacteria comprising the nucleic acid of interest, e.g., gene encoding a protein providing resistance to an antibiotic, sequences required for the amplification of the nucleic acid, e.g., a bacterial origin of replication.

In one embodiment, the powerful phage T5 promoter, that is recognized by E. coli RNA polymerase is used together with a lac operator repression module to provide tightly regulated, high level expression or recombinant proteins in E. coli. In this system, protein expression is blocked in the presence of high levels of lac repressor. In one embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp. (Madison, Wis.) and InVitrogen (San Diego, Calif.), or can be obtained directly from the bacteriophage using standard recombinant DNA techniques (J. Sambrook, E. Fritsch, T. Maniatis, Molecular Cloning: A Laboratory Manual, Cold Spring Laboratory Press, 1989). Bacteriophage polymerases and promoters are further described, e.g., in the following references: Sagawa, H. et al. (1996) Gene 168:37; Cheng, X. et al. (1994) PNAS USA 91:4034; Dubendorff, J. W. and F. W. Studier (1991) Journal of Molecular Biology 219:45; Bujarski, J. J. and P. Kaesberg (1987) Nucleic Acids Research 15:1337; and Studier, F. W. et al. (1990) Methods in Enzymology 185:60). Such plasmids can be modified further according to the specific embodiment of the fusion polypeptide to be expressed.

In another embodiment, the bacterium further comprises a DNA encoding a second polymerase which is capable of mediating transcription from the second promoter, wherein the DNA encoding the second polymerase is operably linked to a third promoter. The third promoter may be a bacterial promoter. However, more than two different polymerases and promoters could be introduced in a bacterium to obtain high levels of transcription. The use of one or more polymerases for mediating transcription in the bacterium can provide a significant increase in the amount of polypeptide in the bacterium relative to a bacterium in which the DNA is directly under the control of a bacterial promoter. The selection of the system to adopt will vary depending on the specific use, e.g., on the amount of protein that one desires to produce.

Generally, a nucleic acid encoding a fusion protein of the invention is introduced into a host cell, such as by transfection, and the host cell is cultured under conditions allowing expression of the fusion polypeptide. Methods of introducing nucleic acids into prokaryotic and eukaryotic cells are well known in the art. Suitable media for mammalian and prokaryotic host cell culture are well known in the art. Generally, the nucleic acid encoding the subject fusion polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

When using a prokaryotic host cell, the host cell may include a plasmid which expresses an internal T7 lysozyme, e.g., expressed from plasmid pLysSL. Lysis of such host cells liberates the lysozyme which then degrades the bacterial membrane.

Other sequences that may be included in a vector for expression in bacterial or other prokaryotic cells include a synthetic ribosomal binding site; strong transcriptional terminators, e.g., $t_0$ from phage lambda and $t_4$ from the rrnB operon in E. coli, to prevent read through transcription and ensure stability of the expressed polypeptide; an origin of replication, e.g., ColE1; and beta-lactamase gene, conferring ampicillin resistance.

Other host cells include prokaryotic host cells. Even more preferred host cells are bacteria, e.g., E. coli. Other bacteria that can be used include Shigella spp., Salmonella spp., Listeria spp., Rickettsia spp., Yersinia spp., Escherichia spp., Klebsiella spp., Bordetella spp., Neisseria spp., Aeromonas spp., Francisella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Vibrio spp., Bacillus spp., and Erysipelothrix spp. Most of these bacteria can be obtained from the American Type Culture Collection (ATCC; 10801 University Blvd., Manassas, Va. 20110-2209).

A number of vectors exist for the expression of recombinant proteins in yeast. For instance, YEP24, YIPS, YEP51, YEP52, pYES2, and YRP17 are cloning and expression vehicles useful in the introduction of genetic constructs into S. cerevisiae (see, for example, Broach et al., (1983) in Experimental Manipulation of Gene Expression, ed. M. Inouye Academic Press, p. 83). These vectors may replicate in E. coli due to the presence of the pBR322 ori, and in S. cerevisiae due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, PMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the (3-gal comprising pBlueBac III).

In another variation, protein production may be achieved using in vitro translation systems. In vitro translation systems are, generally, a translation system which is a cell-free extract comprising at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. An RNA nucleotide for in vitro translation may be produced using methods known in the art. In vitro transcription and translation may be coupled in a one-pot reaction to produce proteins from one or more isolated DNAs.

When expression of a carboxy terminal fragment of a polypeptide is desired, i.e., a truncation mutant, it may be necessary to add a start codon (ATG) to the oligonucleotide fragment comprising the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) J. Bacteriol. 169:751-757) and *Salmonella typhimurium* and its in vitro activity has been demonstrated on recombinant proteins (Miller et al., (1987) PNAS USA 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

In cases where plant expression vectors are used, the expression of a fusion protein may be driven by any of a number of promoters, e.g., a promoter suitable for expression in tobacco. For example, viral promoters such as the 35S RNA and 19S RNA promoters of CaMV (Brisson et al., 1984, Nature, 310:511-514), or the coat protein promoter of TMV (Takamatsu et al., 1987, EMBO J., 6:307-311) may be used; alternatively, plant promoters such as the small subunit of RUBISCO (Coruzzi et al., 1994, EMBO J., 3:1671-1680; Broglie et al., 1984, Science, 224:838-843); or heat shock promoters, e.g., soybean hsp 17.5-E or hsp 17.3-B (Gurley et al., 1986, Mol. Cell. Biol., 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

An alternative expression system which can be used to express a polypeptide tag or fusion protein comprising a polypeptide tag is an insect system. In one such system, Autographa californica nuclear polyhedrosis virus (AcNPV) is used as a vector to express foreign genes. The virus grows in Spodoptera frugiperda cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol., 46:584, Smith, U.S. Pat. No. 4,215,051).

In a specific embodiment of an insect system, the DNA encoding fusion protein is cloned into the pBlueBac111 recombinant transfer vector (Invitrogen, San Diego, Calif.) downstream of the polyhedrin promoter and transfected into Sf9 insect cells (derived from Spodoptera frugiperda Spodoptera frugiperda ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5B1-4 cells derived from Trichoplusia ni egg cell homogenates; available from Invitrogen, San Diego, Calif.) insect cells, to produce large quantities of appropriately post-translationally modified subject polypeptide.

In other embodiments, the components of any the fusion proteins of the invention are produced separately and then linked, e.g., covalently linked, to each other.

For example, an antigen binding domain and a modified HSP70 protein are produced separately in vitro, purified, and mixed together under conditions under which a tag, for example, a biotin or antibody binding protein, will be able to be linked to the polypeptide of interest. For example, the HSP70 protein and/or the antigen binding domain can be obtained (isolated) from a source in which they are known to occur, can be produced and harvested from cell cultures, can be produced by cloning and expressing a gene encoding the desired HSP70 protein or antigen binding domain, or can be synthesized chemically. Furthermore, a nucleic acid sequence encoding the desired HSP70 protein or antigen binding domain, or any component of the fusion proteins of the invention, can be synthesized chemically. Such mixtures of conjugated proteins may have properties different from single fusion proteins.

Linkers (also known as "linker molecules" or "cross-linkers") may be used to conjugate the components of an fusion protein according to the invention. Linkers include chemicals able to react with a defined chemical group of several, usually two, molecules and thus conjugate them. The majority of known cross-linkers react with amine, carboxyl, and sulfhydryl groups. The choice of target chemical group is crucial if the group may be involved in the biological activity of the polypeptides to be conjugated. For example, maleimides, which react with sulfhydryl groups, may inactivate Cys-comprising peptides or proteins that require the Cys to bind to a target. Linkers may be homo-functional (comprising reactive groups of the same type), heterofunctional (comprising different reactive groups), or photoreactive (comprising groups that become reactive on illumination Linker molecules may be responsible for different properties of the conjugated compositions. The length of the linker should be considered in light of molecular flexibility during the conjugation step, and the availability of the conjugated molecule for its target (cell surface molecules and the like). Longer linkers may thus improve the biological activity of the compositions of the present invention, as well as the ease of preparation of them. The geometry of the linker may be used to orient a molecule for optimal reaction with a target. A linker with flexible geometry may allow the cross-linked polypeptides to conformationally adapt as they bind other polypeptides. The nature of the linker may be altered for other various purposes. For example, the aryl-structure of MBuS was found to be less immunogenic than the aromatic spacer of MBS. Furthermore, the hydrophobicity and functionality of the linker molecules may be controlled by the physical properties of component molecules. For example, the hydrophobicity of a polymeric linker may be controlled by the order of monomeric units along the polymer, e.g., a block polymer in which there is a block of hydrophobic monomers interspersed with a block of hydrophilic monomers.

A linker or cross-linker that is useful according to the invention can facilitate proper folding of the fusion protein, improve the biological activity of the fusion proteins of the invention, can facilitate preparation of the fusion proteins of the invention, etc.

A linker can also function to provide for proper folding of the heavy and light chain segments of the scFv. A "linker" according to the invention may also contribute to target recognition.

Any suitable amino acid linker that does not interfere with proper protein folding and function is useful according to the invention In one embodiment, a linker is a combination of nucleic acids that yields a series of neutral or slightly polar amino acids that facilitates proper folding of the fusion protein If an amino acid side chain cannot be ionized it is considered polar but neutral. For example, aspartate is polar and acidic because the carboxylic side chain can be ionized. Tyrosine is polar. The hydroxyl group on the phenyl ring is not easily ionized thus it is considered polar but neutral.

In one embodiment, a linker consists of nucleic acids encoding the following amino acid sequence: GGSSRSS (SEQ ID NO: 21). In another embodiment, the linker consists of nucleic acids encoding the following amino acid sequence: (GGGSGGG)X4 (SEQ ID NO: 22).

In another embodiment the linker sequence comprises the sequence GGGGSGGGGSGGGGS ((Gly$_4$Ser)$_3$) SEQ ID NO: 23). In another embodiment the linker sequence comprises the sequence GGSSRSSSSGGGGSGGGG (SEQ ID NO: 24) or GGSSESSSSGGGGSGGGG (SEQ ID NO: 25). It is preferable to include glycine in the linker sequence because it has an H-side chain whereas all other amino acids have bulkier side chains.

The chemistry of preparing and utilizing a wide variety of molecular linkers is well-known in the art and many premade linkers for use in conjugating molecules are commercially available from vendors such as Pierce Chemical Co., Roche Molecular Biochemicals, United States Biological, and the like.

A. Fusion Protein Production Embodiments

One aspect of the invention relates to an isolated nucleic acid encoding the fusion protein of the invention. In some embodiments, the nucleic acid encodes any of the fusion protein sequences disclosed above.

In certain embodiments, the isolated nucleic acid comprises, consists essentially of, or consists of a nucleic acid selected from:
- a) the nucleotide sequence of any one of SEQ ID NOS:2, 4, 6, 8, or 10;
- b) a nucleotide sequence that is at least about 80% identical to the nucleotide sequence of a);
- c) a nucleotide sequence complementary to (a) or (b);
- d) a nucleotide sequence that is the reverse complement of to (a) or (b); or
- e) any combination of (a) to (d).

```
                                                         (SEQ ID NO: 2)
CAAGTTCAAC TTCAACAATC TGGTCCTGGT CTTGTTACTC CTTCTCAAAC

TCTTTCTCTT ACTTGTGCTA TTTCTGGTGA TTCTGTTTCT TCTAATTCTG

CTACTTGGAA TTGGATTAGA CAATCTCCTT CTAGAGGTCT TGAATGGCTT

GGTAGAACTT ATTATAGATC TAAGTGGTAT AATGATTATG CTGTTTCTGT

TAAGTCTAGA ATGTCTATTA ATCCTGATAC TTCTAAGAAT CAATTTTCTC

TTCAACTTAA TTCTGTTACT CCTGAAGATA CTGCTGTTTA TTATTGTGCT

AGAGGTATGA TGACTTATTA TTATGGTATG GATGTTTGGG GTCAAGGTAC

TACTGTTACT GTTTCTTCTG GTATTCTTGG TTCTGGTGGA GGTGGATCTG

GTGGAGGTGG ATCAGGTGGA GGTGGTTCTC AACCTGTTCT TACTCAATCT

TCTTCTCTTT CTGCTTCTCC TGGTGCTTCT GCTTCTCTTA CTTGTACTCT

TAGATCTGGT ATTAATGTTG GTCCTTATAG AATTTATTGG TATCAACAAA

AGCCTGGTTC TCCTCCTCAA TATCTTCTTA ATTATAAGTC TGATTCTGAT

AAGCAACAAG GTTCTGGTGT TCCTTCTAGA TTTTCTGGTT CTAAGGATGC

TTCTGCTAAT GCTGGTGTTC TTCTTATTTC TGGTCTTAGA TCTGAAGATG

AAGCTGATTA TTATTGTATG ATTTGGCATT CTTCTGCTGC TGTTTTTGGT

GGTGGTACTC AACTTACTGT TCTTGGTGGA GGTGGATCTG GTGGAGGTGG

ATCAGGTGGA GGTGGTTCTG TGACCCCTTT GTCTTTGGGT ATTGAAACTA

AAGGAGGTTT TATGACTAGA CTTATTGAAC GTAATACCAC TATTCCTACG

AAGAGATCAG AGACATTTAC TACTGCTGAT GACAATCAAC CTAGTGTTCA

GATCCAAGTG TATCAAGGAG AGAGGGAAAT TGCTGCACAT AATAAGTTGC

TTGGCTCATT TGAACTTACT GGAATTCCAC CTGCTCCTAG AGGTATTCCA
```

-continued
```
CAAATAGAAG TGACATTTGA CATTGACGCA AATGGGATAG TTCATGTGAC

TGCTAAGGAT AAAGGAACTG GTAAAGAGAA TACTATTCGT ATTCAGGAAG

GTAGTGGACT GTCTAAGGAA GATATTGACA GAATGATAAA GGACGCAGAA
```

(SEQ ID NO: 4)
```
CAAGTTCAAC TTCAACAATC TGGTCCTGGT CTTGTTACTC CTTCTCAAAC

TCTTTCTCTT ACTTGTGCTA TTTCTGGTGA TTCTGTTTCT TCTAATTCTG

CTACTTGGAA TTGGATTAGA CAATCTCCTT CTAGAGGTCT TGAATGGCTT

GGTAGAACTT ATTATAGATC TAAGTGGTAT AATGATTATG CTGTTTCTGT

TAAGTCTAGA ATGTCTATTA ATCCTGATAC TTCAAGAAT CAATTTTCTC

TTCAACTTAA TTCTGTTACT CCTGAAGATA CTGCTGTTTA TTATTGTGCT

AGAGGTATGA TGACTTATTA TTATGGTATG GATGTTTGGG GTCAAGGTAC

TACTGTTACT GTTTCTTCTG GTATTCTTGG TTCTGGTGGA GGTGGATCTG

GTGGAGGTGG ATCAGGTGGA GGTGGTTCTC AACCTGTTCT TACTCAATCT

TCTTCTCTTT CTGCTTCTCC TGGTGCTTCT GCTTCTCTTA CTTGTACTCT

TAGATCTGGT ATTAATGTTG GTCCTTATAG AATTTATTGG TATCAACAAA

AGCCTGGTTC TCCTCCTCAA TATCTTCTTA ATTATAAGTC TGATTCTGAT

AAGCAACAAG GTTCTGGTGT TCCTTCTAGA TTTTCTGGTT CTAAGGATGC

TTCTGCTAAT GCTGGTGTTC TTCTTATTTC TGGTCTTAGA TCTGAAGATG

AAGCTGATTA TTATTGTATG ATTTGGCATT CTTCTGCTGC TGTTTTTGGT

GGTGGTACTC AACTTACTGT TCTTGGTGGA GGTGGATCTG GTGGAGGTGG

ATCAGGTGGA GGTGGTTCTG TGACCCCTTT GTCTTTGGGT ATTGAAACTA

AAGGAGGTTT TATGACTAGA CTTATTGAAC GTAATACCAC TATTCCTACG

AAGAGATCAG AGACATTTAC TACTGCTGAT GACAATCAAC CTAGTGTTCA

GATCCAAGTG TATCAAGGAG AGAGGGAAAT TACTAAGGAG AATAATCTTC

TTGGTAGATT TGAATTGTCT GGTATTCCAC CTGCTCCTAG AGGTATTCCA

CAAATAGAAG TGACATTTGA CATTGACGCA AATGGGATAG TTCATGTGAC

TGCTAAGGAT AAAGGAACTG GTAAAGAGAA TACTATTCGT ATTCAGGAAG

GTAGTGGACT GTCTAAGGAA GATATTGACA GAATGATAAA GGACGCAGAA
```

(SEQ ID NO: 6)
```
CAAGTTCAAC TTCAACAATC TGGTCCTGGT CTTGTTACTC CTTCTCAAAC

TCTTTCTCTT ACTTGTGCTA TTTCTGGTGA TTCTGTTTCT TCTAATTCTG

CTACTTGGAA TTGGATTAGA CAATCTCCTT CTAGAGGTCT TGAATGGCTT

GGTAGAACTT ATTATAGATC TAAGTGGTAT AATGATTATG CTGTTTCTGT

TAAGTCTAGA ATGTCTATTA ATCCTGATAC TTCAAGAAT CAATTTTCTC

TTCAACTTAA TTCTGTTACT CCTGAAGATA CTGCTGTTTA TTATTGTGCT

AGAGGTATGA TGACTTATTA TTATGGTATG GATGTTTGGG GTCAAGGTAC

TACTGTTACT GTTTCTTCTG GTATTCTTGG TTCTGGTGGA GGTGGATCTG

GTGGAGGTGG ATCAGGTGGA GGTGGTTCTC AACCTGTTCT TACTCAATCT

TCTTCTCTTT CTGCTTCTCC TGGTGCTTCT GCTTCTCTTA CTTGTACTCT

TAGATCTGGT ATTAATGTTG GTCCTTATAG AATTTATTGG TATCAACAAA

AGCCTGGTTC TCCTCCTCAA TATCTTCTTA ATTATAAGTC TGATTCTGAT

AAGCAACAAG GTTCTGGTGT TCCTTCTAGA TTTTCTGGTT CTAAGGATGC
```

-continued

```
TTCTGCTAAT GCTGGTGTTC TTCTTATTTC TGGTCTTAGA TCTGAAGATG

AAGCTGATTA TTATTGTATG ATTTGGCATT CTTCTGCTGC TGTTTTTGGT

GGTGGTACTC AACTTACTGT TCTTGGTGGA GGTGGATCTG GTGGAGGTGG

ATCAGGTGGA GGTGGTTCTG TGACCCCTTT GTCTTTGGGT ATTGAAACTA

AAGGAGGTTT TATGACTAGA CTTATTGAAC GTAATACCAC TATTCCTACG

AAGAGATCAG AGACATTTAC TACTGCTGAT GACAATCAAC CTAGTGTTCA

GATCCAAGTG TATCAAGGAGAGAGGGAAATT ACTAAGGATA ATAATCTTCT

TGGTAGATTT GAACTTTCTGG TATTCCACCT GCTCCTAGAG GTATTCCACA

AATAGAAGTG ACATTTGACA TTGACGCAAA TGGGATAGTT CATGTGACTG

CTAAGGATAA AGGAACTGGT AAAGAGAATA CTATTCGTAT TCAGGAAGGT

AGTGGACTGT CTAAGGAAGA TATTGACAGA ATGATAAAGG ACGCAGAA
```

(SEQ ID NO: 8)
```
CAAGTTCAAC TTCAACAATC TGGTCCTGGT CTTGTTACTC CTTCTCAAAC

TCTTTCTCTT ACTTGTGCTA TTTCTGGTGA TTCTGTTTCT TCTAATTCTG

CTACTTGGAA TTGGATTAGA CAATCTCCTT CTAGAGGTCT TGAATGGCTT

GGTAGAACTT ATTATAGATC TAAGTGGTAT AATGATTATG CTGTTTCTGT

TAAGTCTAGA ATGTCTATTA ATCCTGATAC TTCTAAGAAT CAATTTTCTC

TTCAACTTAA TTCTGTTACT CCTGAAGATA CTGCTGTTTA TTATTGTGCT

AGAGGTATGA TGACTTATTA TTATGGTATG GATGTTTGGG GTCAAGGTAC

TACTGTTACT GTTTCTTCTG GTATTCTTGG TTCTGGTGGA GGTGGATCTG

GTGGAGGTGG ATCAGGTGGA GGTGGTTCTC AACCTGTTCT TACTCAATCT

TCTTCTCTTT CTGCTTCTCC TGGTGCTTCT GCTTCTCTTA CTTGTACTCT

TAGATCTGGT ATTAATGTTG GTCCTTATAG AATTTATTGG TATCAACAAA

AGCCTGGTTC TCCTCCTCAA TATCTTCTTA ATTATAAGTC TGATTCTGAT

AAGCAACAAG GTTCTGGTGT TCCTTCTAGA TTTTCTGGTT CTAAGGATGC

TTCTGCTAAT GCTGGTGTTC TTCTTATTTC TGGTCTTAGA TCTGAAGATG

AAGCTGATTA TTATTGTATG ATTTGGCATT CTTCTGCTGC TGTTTTTGGT

GGTGGTACTC AACTTACTGT TCTTGGTGGA TCTTCAAGAT CTTCAAGTTC

TGGTGGAGGA GGTTCTGGTG GAGGTGGTGT GACCCCTTTG TCTTTGGGTA

TTGAAACTAA AGGAGGTTTT ATGACTAGAC TTATTGAACG TAATACCACT

ATTCCTACGA AGAGATCAGA GACATTTACT ACTGCTGATG ACAATCAACC

TAGTGTTCAG ATCCAAGTGT ATCAAGGAGA GAGGGAAATT ACTAAGGAGA

ATAATCTTCT TGGTAGATTT GAATTGTCTG GTATTCCACC TGCTCCTAGA

GGTATTCCAC AAATAGAAGT GACATTTGAC ATTGACGCAA ATGGGATAGT

TCATGTGACT GCTAAGGATA AAGGAACTGG TAAAGAGAAT ACTATTCGTA

TTCAGGAAGG TAGTGGACTG TCTAAGGAAG ATATTGACAG AATGATAAAG

GACGCAGAA
```

(SEQ ID NO: 10)
```
CAAGTTCAAC TTCAACAATC TGGTCCTGGT CTTGTTACTC CTTCTCAAAC

TCTTTCTCTT ACTTGTGCTA TTTCTGGTGA TTCTGTTTCT TCTAATTCTG

CTACTTGGAA TTGGATTAGA CAATCTCCTT CTAGAGGTCT TGAATGGCTT
```

```
                        -continued
GGTAGAACTT ATTATAGATC TAAGTGGTAT AATGATTATG CTGTTTCTGT

TAAGTCTAGA ATGTCTATTA ATCCTGATAC TTCTAAGAAT CAATTTTCTC

TTCAACTTAA TTCTGTTACT CCTGAAGATA CTGCTGTTTA TTATTGTGCT

AGAGGTATGA TGACTTATTA TTATGGTATG GATGTTTGGG GTCAAGGTAC

TACTGTTACT GTTTCTTCTG GTATTCTTGG TTCTGGTGGA GGTGGATCTG

GTGGAGGTGG ATCAGGTGGA GGTGGTTCTC AACCTGTTCT TACTCAATCT

TCTTCTCTTT CTGCTTCTCC TGGTGCTTCT GCTTCTCTTA CTTGTACTCT

TAGATCTGGT ATTAATGTTG GTCCTTATAG AATTTATTGG TATCAACAAA

AGCCTGGTTC TCCTCCTCAA TATCTTCTTA ATTATAAGTC TGATTCTGAT

AAGCAACAAG GTTCTGGTGT TCCTTCTAGA TTTTCTGGTT CTAAGGATGC

TTCTGCTAAT GCTGGTGTTC TTCTTATTTC TGGTCTTAGA TCTGAAGATG

AAGCTGATTA TTATTGTATG ATTTGGCATT CTTCTGCTGC TGTTTTTGGT

GGTGGTACTC AACTTACTGT TCTTGGTGGA TCTTCAGAAT CTTCAAGTTC

TGGTGGAGGA GGTTCTGGTG GAGGTGGTGT GACCCCTTTG TCTTTGGGTA

TTGAAACTAA AGGAGGTTTT ATGACTAGAC TTATTGAACG TAATACCACT

ATTCCTACGA AGAGATCAGA GACATTTACT ACTGCTGATG ACAATCAACC

TAGTGTTCAG ATCCAAGTGT ATCAAGGAGA GAGGGAAATT ACTAAGGAGA

ATAATCTTCT TGGTAGATTT GAATTGTCTG GTATTCCACC TGCTCCTAGA

GGTATTCCAC AAATAGAAGT GACATTTGAC ATTGACGCAA ATGGGATAGT

TCATGTGACT GCTAAGGATA AAGGAACTGG TAAAGAGAAT ACTATTCGTA

TTCAGGAAGG TAGTGGACTG TCTAAGGAAG ATATTGACAG AATGATAAAG

GACGCAGAA
```

In some embodiments, the isolated nucleic acid is at least about 80%, 85%, 90%, 91%, 92%, 93%, 94%, 95%, 96%, 97%, 98%, or 99% identical to the nucleotide sequence of any one of SEQ ID NOS:2, 4, 6, 8, or 10.

In certain embodiments, the isolated nucleic acid is codon-optimized for expression in a host cell, e.g., a bacterial cell, a mammalian cell, an insect cell, or a plant cell. In some embodiments, the isolated nucleic acid is codon optimized for expression in a plant cell, e.g., wherein the plant is Nicotiana benthamiana or Nicotiana tabacum.

The isolated nucleic acid may be operably linked to a promoter, e.g., a promoter that is suitable for expression in the host cell of interest. In some embodiments, the promoter is a plant promoter.

Another aspect of the invention relates to an expression vector comprising the nucleic acid of the invention.

The invention further relates to a cell comprising the isolated nucleic acid or the expression vector of the invention. The cell may be a bacterial cell, a mammalian cell, an insect cell, or a plant cell, e.g., a plant cell selected from *N benthamiana* and *N tabacum*.

An additional aspect of the invention relates to a transgenic plant cell, plant part, or plant comprising the isolated nucleic acid of the invention.

3. Methods of Using the Fusion Proteins

The fusion proteins described herein can be administered to a subject to enhance that subject's immune response, particularly a cell-mediated cytolytic response, against a cell expressing the antigen recognized by the antigen binding domain. The fusion protein may simply enhance the immune response (thus serving as an immunogenic composition), or confer protective immunity (thus serving as a vaccine).

Thus, the protein fusion polypeptides produced as described above may be purified to a suitable purity for use as a pharmaceutical composition. Generally, a purified composition will have one species that comprises more than about 85 percent of all species present in the composition, more than about 85%, 86%, 87%, 88%, 89%, 90%, 91%, 92%, 93%, 94%, 95%, 96%, 97%, 98%, 99% or more of all species present. The object species may be purified to essential homogeneity (contaminant species cannot be detected in the composition by conventional detection methods) wherein the composition consists essentially of a single species. A skilled artisan may purify a fusion protein using standard techniques for protein purification, for example, immunoaffinity chromatography, size exclusion chromatography, etc., in light of the teachings herein. Purity of a polypeptide may be determined by a number of methods known to those of skill in the art, including for example, amino-terminal amino acid sequence analysis, gel electrophoresis and mass-spectrometry analysis.

Accordingly, provided are pharmaceutical compositions comprising the above-described fusion proteins. In one aspect, provided are pharmaceutically acceptable compositions which comprise a therapeutically-effective amount of one or more of the compounds described above and below, formulated together with one or more pharmaceutically acceptable carriers (additives) and/or diluents. In another aspect, in certain embodiments, the compounds may be administered as such or in admixtures with pharmaceutically acceptable carriers and may also be administered in conjunction with other agents. Conjunctive (combination) therapy thus includes sequential, simultaneous and separate, or co-administration of the active compound in a way that the therapeutic effects of the first administered one has not entirely disappeared when the subsequent is administered.

The fusion proteins described herein can be administered to a subject in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the compositions described herein can contain and be administered together with other pharmacologically acceptable components such as biologically active agents (e.g., adjuvants such as alum), surfactants (e.g., glycerides), excipients (e.g., lactose), carriers, diluents and vehicles. Furthermore, the compositions can be used ex vivo as a means of stimulating white blood cells obtained from a subject to elicit, expand and propagate antigen-specific immune cells in vitro that are subsequently reintroduced into the subject.

Further, a fusion protein can be administered by in vivo expression of a nucleic acid encoding such protein sequences into a human subject. Expression of such a nucleic acid can also be achieved ex vivo as a means of stimulating white blood cells obtained from a subject to elicit, expand and propagate antigen-specific immune cells in vitro that are subsequently reintroduced into the subject. Expression vectors suitable for directing the expression of a fusion protein of interest can be selected from the large variety of vectors currently used in the field. Preferred will be vectors that are capable of producing high levels of expression as well as are effective in transducing a gene of interest. For example, recombinant adenovirus vector pJM17 (All et al., Gene Therapy 1:367-84 (1994); Berkner K L., Biotechniques 6:616-24 1988), second generation adenovirus vectors DEl/DE4 (Wang and Finer, Nature Medicine 2:714-6 (1996)), or adeno-associated viral vector AAV/Neo (Muro-Cacho et al., J. Immunotherapy 11:231-7 (1992)) can be used. Furthermore, recombinant retroviral vectors MFG (Jaffee et al., Cancer Res. 53:2221-6 (1993)) or LN, LNSX, LNCX, LXSN (Miller and Rosman, Biotechniques 7:980-9 (1989)) can be employed. Herpes simplex virus-based vectors such as pHSV1 (Geller et al., Proc. Nat'l Acad. Sci. 87:8950-4 (1990) or vaccinia viral vectors such as MVA (Sutter and Moss. Proc. Nat'l Acad. Sci. 89:10847-51 (1992)) can serve as alternatives.

Frequently used specific expression units including promoter and 3' sequences are those found in plasmid cDNA3 (Invitrogen), plasmid AH5, pRC/CMV (Invitrogen), pCMU II (Paabo et al., EMBO J. 5:1921-1927 (1986)), pZip-Neo SV (Cepko et al., Cell 37:1053-1062 (1984)) and pSRa (DNAX, Palo Alto, Calif.). The introduction of genes into expression units and/or vectors can be accomplished using genetic engineering techniques, as described in manuals like Molecular Cloning and Current Protocols in Molecular Biology (Sambrook, J., et al., Molecular Cloning, Cold Spring Harbor Press (1989); Ausubel, F. M. et al., Current Protocols in Molecular Biology, Greene Publishing Associates and Wiley-Interscience (1989)). A resulting expressible nucleic acid can be introduced into cells of a human subject by any method capable of placing the nucleic acid into cells in an expressible form, for example as part of a viral vector such as described above, as naked plasmid or other DNA, or encapsulated in targeted liposomes or in erythrocyte ghosts (Friedman, T., Science, 244:1275-1281 (1989); Rabinovich, N. R. et al. Science. 265:1401-1404 (1994)). Methods of transduction include direct injection into tissues and tumors, liposomal transfection (Fraley et al., Nature 370:111-117 (1980)), receptor-mediated endocytosis (Zatloukal et al., Ann. N.Y. Acad. Sci. 660:136-153 (1992)), and particle bombardment-mediated gene transfer (Eisenbraun et al., DNA & Cell. Biol. 12:791-797 (1993)).

The amount of fusion polypeptide (fused, conjugated or noncovalently joined as discussed before) in the compositions of the present invention is an amount which produces an effective immunostimulatory response in a subject as determined by the methods described herein. An effective amount is an amount such that when administered, it induces an immune response. In addition, the amount of fusion protein administered to the subject will vary depending on a variety of factors, including the engineered antibody and stress protein employed, the size, age, body weight, general health, sex, and diet of the subject as well as on the subject's general immunological responsiveness. Adjustment and manipulation of established dose ranges are well within the ability of those skilled in the art. For example, the amount of engineered fusion protein according to the invention, for example, mesothelin antibody-modified HSP70 fusion protein, can be from about 1 microgram to about 1 gram, preferably from about 100 microgram to about 1 gram, and from about 1 milligram to about 1 gram. An effective amount of a composition comprising an expression vector is an amount such that when administered, it induces an immune response against the antigen against which the antigen binding domain is directed. Furthermore, the amount of expression vector administered to the subject will vary depending on a variety of factors, including the antigen binding domain and HSP70 protein expressed, the size, age, body weight, general health, sex, and diet of the subject, as well as on the subject's general immunological responsiveness. Additional factors that need to be considered are the route of application and the type of vector used. For example, when prophylactic or therapeutic treatment is carried out with a viral vector containing a nucleic acid encoding an engineered fusion protein according to the invention, the effective amount will be in the range of $10^4$ to $10^{12}$ helper-free, replication-defective virus per kg body weight, preferably in the range of $10^5$ to $10^{11}$ virus per kg body weight and most preferably in the range of $10^6$ to $10^{10}$ virus per kg body weight.

An effective dose can be estimated initially from in vitro assays. For example, a dose can be formulated in animal models to achieve an induction of an immune response using techniques that are well known in the art. One having skill in the art could readily optimize administration to humans based on animal data. Dosage amount and interval may be adjusted individually. For example, when used as a vaccine, the proteins and/or strains of the invention may be administered in about 1 to 3 doses for a 1-36 week period. Preferably, 3 doses are administered, at intervals of about 3-4 months, and booster vaccinations may be given periodically thereafter. Alternate protocols may be appropriate for individual patients. A suitable dose is an amount of protein or strain that, when administered as described above, is capable of raising an immune response in an immunized patient sufficient to protect the patient from the condition or infection for at least 1-2 years.

The compositions may also include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, or Bortadella pertussis. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., 1997, Vaccine 15:1562-1567), SBAS7, Al(OH)$_3$ and CpG oligonucleotide (WO96/02555).

In the vaccines of the present invention, the adjuvant may induce a Th1 type immune response. Suitable adjuvant systems include, for example, a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and may comprise a formulation.

In particular embodiments of the invention, more than one administration (e.g., two, three, four, or more administrations) can be employed over a variety of time intervals (e.g., hourly, daily, weekly, monthly, etc.) to achieve therapeutic effects.

A. Method of Use Embodiments

One aspect of the invention relates to a method for inducing an immune response to an antigen in a subject, comprising administering to the subject the fusion protein of the invention that specifically binds the antigen, thereby inducing an immune response.

Another aspect of the invention relates to a method of treating a disease associated with an antigen in a subject in need thereof, comprising administering to the subject a therapeutically effective amount of the fusion protein of any one of claims 1-31 that specifically binds the antigen, thereby treating the disease.

In some embodiments, the antigen is a disease antigen. The antigen may be a viral antigen, bacterial antigen, pathogen antigen, or cancer antigen as described above. In some embodiments, the antigen is a cancer antigen, e.g., mesothelin.

In certain embodiments, the disease associated with an antigen is a pathogen infection, e.g., a viral infection. In some embodiments, the disease associated with an antigen is a cancer that expresses the antigen, e.g., mesothelin. In some embodiments, the mesothelin—expressing cancer is ovarian cancer, meningioma, glioma, metastases to the leptomininges, mesothelioma, adenocarcinoma of the uterus, malignant mesothelioma, pancreatic cancer, or lung adenocarcinoma.

In some embodiments, the methods of the invention further comprise administering to the subject an additional active agent. The additional active agent may be a therapeutic agent, e.g., an anti-pathogen agent or an anti-cancer agent.

Anti-cancer agents, include, without limitation, 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g. prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide). In another embodiment, the compounds of the invention are administered in conjunction with anti-angiogenesis agents, such as antibodies to VEGF (e.g., bevacizumab (AVASTIN), ranibizumab (LUCENTIS)) and other promoters of angiogenesis (e.g., bFGF, angiopoietin-1), antibodies to alpha-v/beta-3 vascular integrin (e.g., VITAXIN), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, PI-88, vatalanib, everolimus, suramin, sunitinib malate, XL184, ZD6474, ATN-161, cilenigtide, and celecoxib.

Suitable antiviral agents include, for example, virus-inactivating agents such as nonionic, anionic and cationic surfactants, and C31 G (amine oxide and alkyl betaine), polybiguanides, docosanol, acylcarnitine analogs, octyl glycerol, and antimicrobial peptides such as magainins, gramicidins, protegrins, and retrocyclins. Mild surfactants, e.g., sorbitan monolaurate, may advantageously be used as antiviral agents in the compositions described herein. Other antiviral agents that may advantageously be utilized in the compositions described herein include nucleotide or nucleoside analogs, such as tenofovir, acyclovir, amantadine, didanosine, foscarnet, ganciclovir, ribavirin, vidarabine, zalcitabine, and zidovudine. Further antiviral agents that may be used include non-nucleoside reverse transcriptase inhibitors, such as UC-781 (thiocarboxanilide), pyridinones, TIBO, nevaripine, delavirdine, calanolide A, capravirine and efavirenz. Other antiviral agents that may be used are those in the category of HIV entry blockers, such as cyanovirin-N, cyclodextrins, carregeenans, sulfated or sulfonated polymers, mandelic acid condensation polymers, monoclonal antibodies, chemokine receptor antagonists such as TAK-779, SCH-C/D, and AMD-3100, and fusion inhibitors such as T-20 and 1249.

Suitable antibacterial agents include antibiotics, such as aminoglycosides, cephalosporins, including first, second and third generation cephalosporins; macrolides, including erythromycins, penicillins, including natural penicillins, penicillinase-resistant penicillins, aminopenicillins, extended spectrum penicillins; sulfonamides, tetracyclines, fluoroquinolones, metronidazole and urinary tract antiseptics.

Suitable antifungal agents include amphotericin B, nystatin, griseofulvin, flucytosine, fluconazole, potassium iodide, intraconazole, clortrimazole, miconazole, ketoconazole, and tolnaftate.

Suitable antiprotozoal agents include antimalarial agents, such as chloroquine, primaquine, pyrimethamine, quinine, fansidar, and mefloquine; amebicides, such as dioloxamide, emetine, iodoquinol, metronidazole, paromomycine and quinacrine; pentamidine isethionate, atovaquone, and eflornithine.

The additional active agent may be an agent that treats or enhances the effect of a treatment against a symptom or side effect of a disease or treatment. In one embodiment, the additional active agent is an anti-inflammatory agent. Examples include, without limitation, H1-antihistamines (e.g., cetirizine), H2-antihistamines (e.g., ranitidine, famotidine), antileukotrienes (e.g., montelukast, zileuton), and nonsteroidal anti-inflammatory drugs.

The additional active agent may be an immunostimulatory agent and/or an immune checkpoint inhibitor that enhances the immunostimulatory effect of the fusion protein of the invention. Immunostimulatory agents include, without limitation, interleukin, interferon, cytokine, toll-like receptor (TLR) agonist, cytokine receptor agonist, CD40 agonist, Fc receptor agonist, CpG-containing immunostimulatory nucleic acid, complement receptor agonist, adjuvant, or CXCL12/CXCR4 axis inhibitors such as AMD3100, KRH-1636, T-20, T-22, T-140, TE-14011, T-14012, or TN14003, or an antibody that interferes with the dimerization of CXCR4. Immune checkpoint inhibitors include, without limitation, inhibitors of PD-1, PD-L1, CTLA4, B7-H3, B7-H4, BTLA, IDO, KIR, LAG3, A2AR, TIM-3, and VISTA, such as nivolumab, pembrolizumab, ipilimumab, durvalumab, or atezolizumab.

In some embodiments, the methods of the invention further comprise administering to the subject an additional therapy. The additional therapy may be any therapy known to be effective for treating a disease, e.g., therapies known to be effective for cancer treatment, e.g., surgery, radiotherapy, proton beam therapy, light-based therapy, etc.

4. Kits

The present invention provides kits for expressing an engineered fusion protein according to the invention. Such kits may be comprised of nucleic acids encoding an engineered fusion protein of the invention. The nucleic acids may be included in a plasmid or a vector, e.g., a bacterial plasmid or viral vector. Other kits comprise an engineered fusion polypeptide. Furthermore, the present invention provides kits for producing and/or purifying fusion polypeptides according to the invention The present invention provides kits for preventing or treating infectious, inflammatory, autoimmune or malignant disease in a patient. For example, a kit may comprise one or more pharmaceutical compositions as described above and optionally instructions for their use. In still other embodiments, the invention provides kits comprising one more pharmaceutical composition and one or more devices for accomplishing administration of such compositions.

Kit components may be packaged for either manual or partially or wholly automated practice of the foregoing methods. In other embodiments involving kits, instructions for their use may be provided.

The present invention is more particularly described in the following examples that are intended as illustrative only since numerous modifications and variations therein will be apparent to those skilled in the art.

EXAMPLE 1

Preparation and Therapeutic Activity of VIC-008

A novel fusion protein, VIC-007 (SEQ ID NO:28), consists of the broadly immune-activating *Mycobacterium tuberculosis*-derived heat shock protein 70 (MtbHsp70) and the tumor antigen targeting activity of a single-chain variable fragment (scFv) binding mesothelin (MSLN), a validated immunotherapy target (4-6). MSLN is highly overexpressed on the surface of common epithelial cancers including epithelial malignant mesothelioma and ovarian cancer, while expressed at relatively low levels only in mesothelial cells lining the pleura, pericardium, and peritoneum in healthy individuals (7-10). MtbHsp70 is well characterized and functions as a potent immune-activating adjuvant. It stimulates monocytes and dendritic cells (DCs) to produce CC-chemokines (11, 12), which attract antigen processing and presenting macrophages, DCs, and effector T and B cells (13). In theory, fusion of anti-MSLN scFv and MtbHsp70 takes advantage of the immune-activating action of MtbHsp70 and the tumor-targeting activity of the scFv, which will yield anti-tumor responses against the broadest profile of tumor antigens.

Although our previous studies showed that VIC-007 significantly enhanced survival of immune competent mice with ovarian or malignant mesothelioma tumors through the augmentation of tumor-specific cell-mediated immune responses (14), the fusion protein did not result in long-term remission. In this study a new version of the fusion protein, VIC-008 (SEQ ID NO:27), was reconstructed from VIC-007 to remove redundant amino acids and minimize the activity of the natural peptide-binding site of MtbHsp70. VIC-007 and VIC-008 were compared side by side in the same set of mice and it was found that VIC-008 conferred significantly improved antitumoral efficacy in a syngeneic, orthotopic and immune competent murine model of ovarian cancer.

Materials and Methods

Cells: The ID8 ovarian cancer cells, a kind gift from Kathy Roby (University of Kansas Medical Center, Kansas City, Kans.) (15), were transfected with luciferase lentiviral vector and stably expressed luciferase, here named Luc-ID8. Cells were maintained at 37° C. in DMEM with 2 mmol/L L-glutamine, 10 units/ml penicillin, 10 μg/ml streptomycin, and 10% fetal bovine serum in humidified atmosphere with 5% $CO_2$. Cells were cultured until 80% confluent, and harvested with Trypsin EDTA (Mediatech) for animal injections.

Animal model and treatment: Ovarian cancer was established by Intraperitoneal (i.p.) injection of syngeneic cancer cells Luc-ID8 ($5 \times 10^6$ cells per mouse) into 6-week-old female C57BL/6 mice. All mice were purchased from Jackson laboratories. Mice with ovarian tumors were treated 7 days after tumor cell inoculation with i.p. injections of VIC-007 (4 pg per mouse), VIC-008 (4 pg per mouse), or normal saline. This was followed by 3 further treatments at 7-day intervals. All studies were performed in a manner that was blinded to the observer under protocols that were approved by the Massachusetts General Hospital Subcommittee on Research Animal Care (SRAC).

In vivo imaging of tumor growth: Intraperitoneal tumor growth was monitored weekly after tumor cell inoculation using in vivo live imaging by IVIS Spectrum (PerkinElmer).

Mice were injected intraperitoneally with 150 mg/kg body weight of D-luciferin 10 min in advance and subsequently imaged by IVIS Spectrum.

Mouse survival: For survival studies, we observed the mice daily 1 week after inoculation of tumor cells. Tumor generations were consistently first evident via abdominal distension secondary to malignant ascites, and tumor-bearing mice were euthanized at the endpoint when there were signs of distress, including fur ruffling, rapid respiratory rate, hunched posture, reduced activity, and progressive ascites formation as previously described (16).

Statistical analysis: Statistical differences between three or more experimental groups were analyzed using Two-Way ANOVA, followed by Tukey's multiple comparison tests when mean of each group is compared with that of every other group. Survival was analyzed with the Log-rank test. Prism 6.0 software (GraphPad Software) was used for all the statistical analysis.

Results and Discussion

Reconstruction of the fusion protein scFv-MtbHsp70: The fusion protein scFv-MtbHsp70 was constructed with V Hand V L from anti-MSLN p4 scFv (17) fused to full length MtbHsp70 with a (G4S)3 linker in between, which has been shown in our previous study (14). The previous version of the fusion protein VIC-007 achieved significant control of tumor growth and prolongation of the survival of tumor-bearing mice, but the antitumoral efficacy of the treatment regimen used needed to be improved. Antigenic peptides linked to MtbHsp70 through both non-covalent binding and by genetic fusion can elicit both MHC class I-restricted CDS+ and MEW class II-restricted CD4+ T-cell responses (18-22). In this study a new version of the scFv-MtbHsp70 fusion protein was developed, VIC-008, which was modified from the original VIC-007 by the elimination of redundant amino acids and the introduction of a single amino acid mutation, valine (V) in place of phenylalanine (F), at position 381 of MtbHsp70 (FIG. 1). This change is designed to prevent peptide binding (23) while retaining the immune-stimulatory capacity of the protein, in order to reduce the possibility that MtbHsp70 might incidentally bind and deliver other antigens that could result in off target effects or the induction of tolerance or autoimmunity.

The fusion proteins were constructed and expressed by WuXi App Tech (Shanghai, China) in CHO cells and provided at a purity of above 95% by HPLC and an endotoxin level of less than 1.0 EU/mg.

Figure 2B:
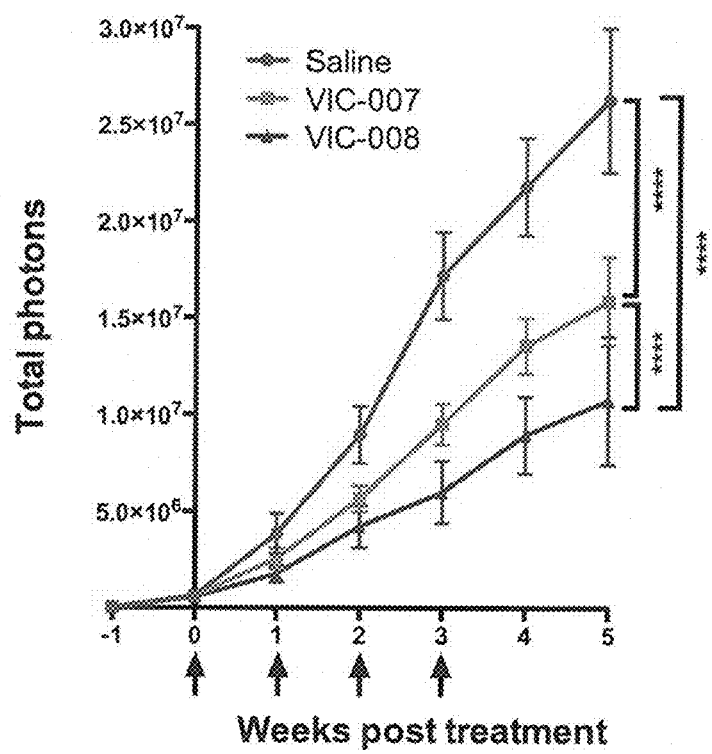

VIC-008 enhances the control of tumor growth: Murine ovarian cancer was established by i.p. injection of syngeneic cancer cells Luc-ID8 in immune competent C57BL/6 mice and treated with VIC-007 and VIC-008 as described in the section of materials and methods. As shown in FIG. 2, both VIC-007 and VIC-008 significantly slowed tumor growth as recorded by bioluminescence signals compared to saline ($p<0.0001$ and $p<0.0001$) while VIC-008 further significantly delayed tumor growth compared to VIC-007 ($p<0.0001$).

Figure 3:
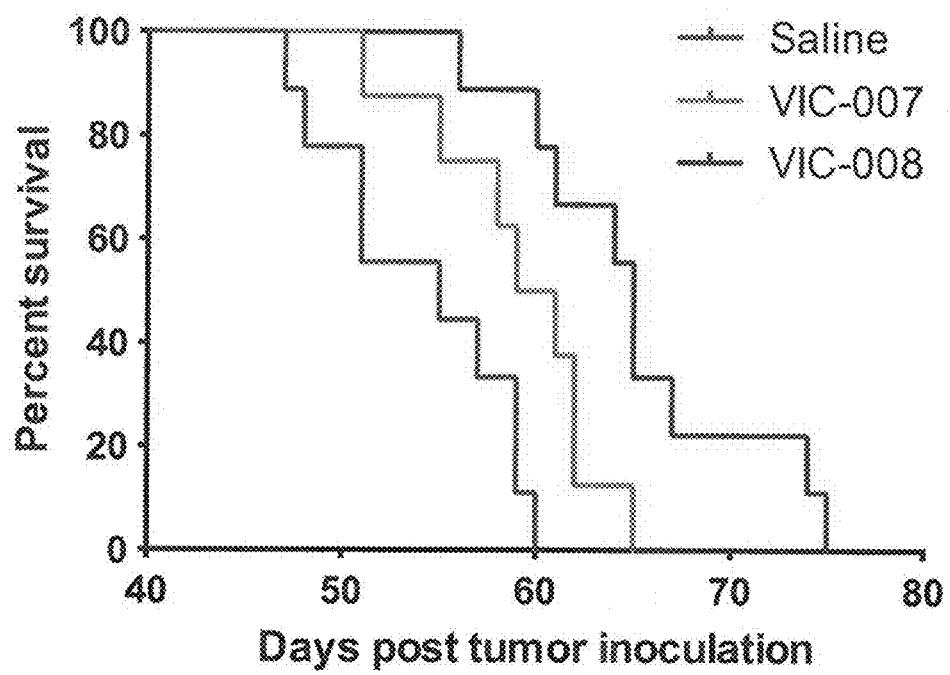

VIC-008 enhances the prolongation of mouse survival: The efficacy of VIC-007 and VIC-008 to prolong survival in the tumor-bearing mice was further evaluated. As shown in FIG. 3, both VIC-007 and VIC-008 significantly enhanced the survival of tumor-bearing mice compared to saline ($p=0.0253$ and $p=0.0002$) with increased median survival of 55 days from saline to 60 days from VIC-007 and further to 65 days from VIC-008. VIC-008 further significantly prolonged the survival of the tumor-bearing mice compared to VIC-007 ($p=0.0301$).

Taken together, these data showed that the new version of the fusion protein VIC-008 significantly delayed the tumor growth and prolonged the survival in a syngeneic murine model of ovarian cancer. Improved mouse survival of VIC-008 compared to VIC-007 is likely related to the changes made to the protein sequences. This study provides a definitive preclinical validation of the mesothelin targeted immune activating fusion protein as a therapeutic agent for ovarian cancer.

REFERENCES

1. Siegel R, DeSantis C, Virgo K, Stein K, Mariotto A, Smith T, et al. Cancer treatment and survivorship statistics, 2012. CA: a cancer journal for clinicians. 2012; 62(4):220-41. Epub 2012/06/16.
2. Bast R C, Jr., Hennessy B, Mills G B. The biology of ovarian cancer: new opportunities for translation. Nature reviews Cancer. 2009; 9(6):415-28. Epub 2009/05/23.
3. Mantia-Smaldone G M, Corr B, Chu C S. Immunotherapy in ovarian cancer. Human vaccines & immunotherapeutics. 2012; 8(9):1179-91. Epub 2012/08/22.
4. Hassan R, Cohen S J, Phillips M, Pastan I, Sharon E, Kelly R J, et al. Phase I clinical trial of the chimeric anti-mesothelin monoclonal antibody MORAb-009 in patients with mesothelin-expressing cancers. Clinical cancer research: an official journal of the American Association for Cancer Research. 2010; 16(24):6132-8. Epub 2010/11/03.
5. Hassan R, Ho M. Mesothelin targeted cancer immunotherapy. Eur J Cancer. 2008; 44(1):46-53. Epub 2007/10/20.
6. Kreitman R J, Hassan R, Fitzgerald D J, Pastan I. Phase I trial of continuous infusion anti-mesothelin recombinant immunotoxin SS1P. Clinical cancer research: an official journal of the American Association for Cancer Research. 2009; 15(16):5274-9. Epub 2009/08/13.
7. Chang K, Pastan I. Molecular cloning of mesothelin, a differentiation antigen present on mesothelium, mesotheliomas, and ovarian cancers. Proceedings of the National Academy of Sciences of the United States of America. 1996; 93(1):136-40. Epub 1996/01/09.
8. Argani P, Iacobuzio-Donahue C, Ryu B, Rosty C, Goggins M, Wilentz R E, et al. Mesothelin is overexpressed in the vast majority of ductal adenocarcinomas of the pancreas: identification of a new pancreatic cancer marker by serial analysis of gene expression (SAGE). Clinical cancer research: an official journal of the American Association for Cancer Research. 2001; 7(12):3862-8. Epub 2001/12/26.
9. Ho M, Bera T K, Willingham M C, Onda M, Hassan R, FitzGerald D, et al. Mesothelin expression in human lung cancer. Clinical cancer research: an official journal of the American Association for Cancer Research. 2007; 13(5):1571-5. Epub 2007/03/03.
10. Tang Z, Qian M, Ho M. The role of mesothelin in tumor progression and targeted therapy. Anti-cancer agents in medicinal chemistry. 2013; 13(2):276-80. Epub 2012/06/23.
11. Floto R A, MacAry P A, Boname J M, Mien T S, Kampmann B, Hair J R, et al. Dendritic cell stimulation by mycobacterial Hsp70 is mediated through CCR5. Science. 2006; 314(5798):454-8. Epub 2006/10/21.
12. Wang Y, Kelly C G, Karttunen J T, Whittall T, Lehner P J, Duncan L, et al. CD40 is a cellular receptor mediating mycobacterial heat shock protein 70 stimulation of CC-chemokines. Immunity. 2001; 15(6):971-83. Epub 2002/01/05.
13. Baggiolini M. Chemokines and leukocyte traffic. Nature. 1998; 392(6676):565-8. Epub 1998/04/29.
14. Yuan J, Kashiwagi S, Reeves P, Nezivar J, Yang Y, Arrifin N H, et al. A novel mycobacterial Hsp70-containing fusion protein targeting mesothelin augments antitumor immunity and prolongs survival in murine models of ovarian cancer and mesothelioma. Journal of hematology & oncology. 2014; 7:15. Epub 2014/02/26.
15. Roby K F, Taylor C C, Sweetwood J P, Cheng Y, Pace J L, Tawfik O, et al. Development of a syngeneic mouse model for events related to ovarian cancer. Carcinogenesis. 2000; 21(4):585-91. Epub 2000/04/07.
16. Righi E, Kashiwagi S, Yuan J, Santosuosso M, Leblanc P, Ingraham R, et al. CXCL12/CXCR4 blockade induces multimodal antitumor effects that prolong survival in an immunocompetent mouse model of ovarian cancer. Cancer research. 2011; 71(16):5522-34. Epub 2011/07/12.
17. Bergan L, Gross J A, Nevin B, Urban N, Scholler N. Development and in vitro validation of anti-mesothelin biobodies that prevent CA125/Mesothelin-dependent cell attachment. Cancer letters. 2007; 255(2):263-74. Epub 2007/06/15.
18. Udono H, Srivastava P K. Heat shock protein 70-associated peptides elicit specific cancer immunity. The Journal of experimental medicine. 1993; 178(4):1391-6. Epub 1993/10/01.
19. Suto R, Srivastava P K. A mechanism for the specific immunogenicity of heat shock protein-chaperoned peptides. Science. 1995; 269(5230):1585-8. Epub 1995/09/15.
20. Suzue K, Young R A. Adjuvant-free hsp70 fusion protein system elicits humoral and cellular immune responses to HIV-1 p24. J Immunol. 1996; 156(2):873-9. Epub 1996/01/15.
21. Huang Q, Richmond J F, Suzue K, Eisen H N, Young R A. In vivo cytotoxic T lymphocyte elicitation by mycobacterial heat shock protein 70 fusion proteins maps to a discrete domain and is CD4(+) T cell independent. The Journal of experimental medicine. 2000; 191(2):403-8. Epub 2000/01/19.
22. Ciupitu A-M T, Petersson M, O'Donnell C L, Williams K, Jindal S, Kiessling R, et al. Immunization with a Lymphocytic Choriomeningitis Virus Peptide Mixed with Heat Shock Protein 70 Results in Protective Antiviral Immunity and Specific Cytotoxic T Lymphocytes. The Journal of experimental medicine. 1998; 187(5):685-91.
23. MacAry P A, Javid B, Floto R A, Smith K G, Oehlmann W, Singh M, et al. HSP70 peptide binding mutants separate antigen delivery from dendritic cell stimulation. Immunity. 2004; 20(1):95-106. Epub 2004/01/24.

EXAMPLE 2

Additional Studies on VIC-008

Figure 4:
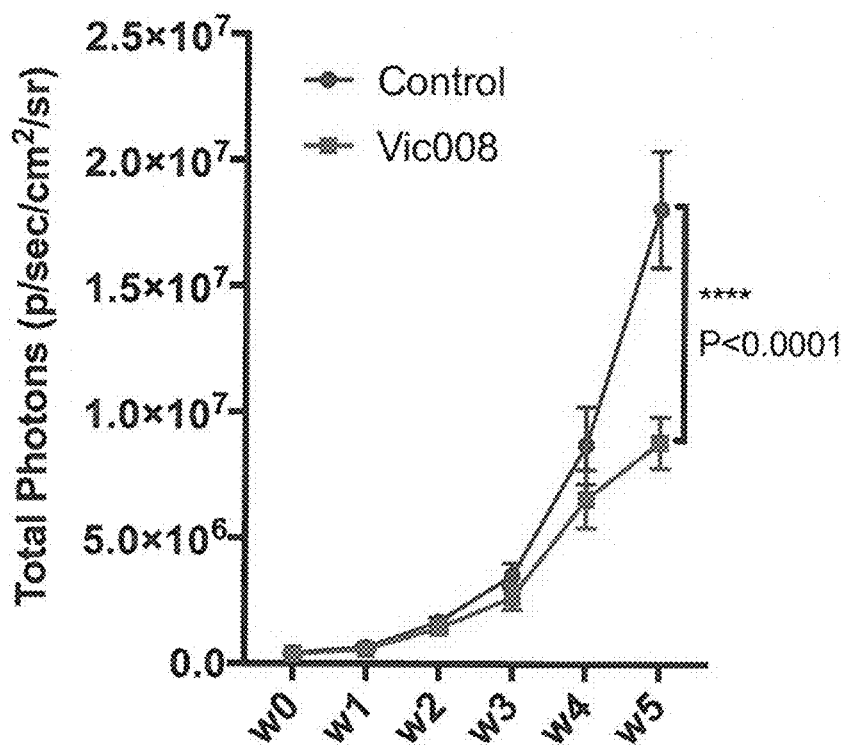
Figure 5:
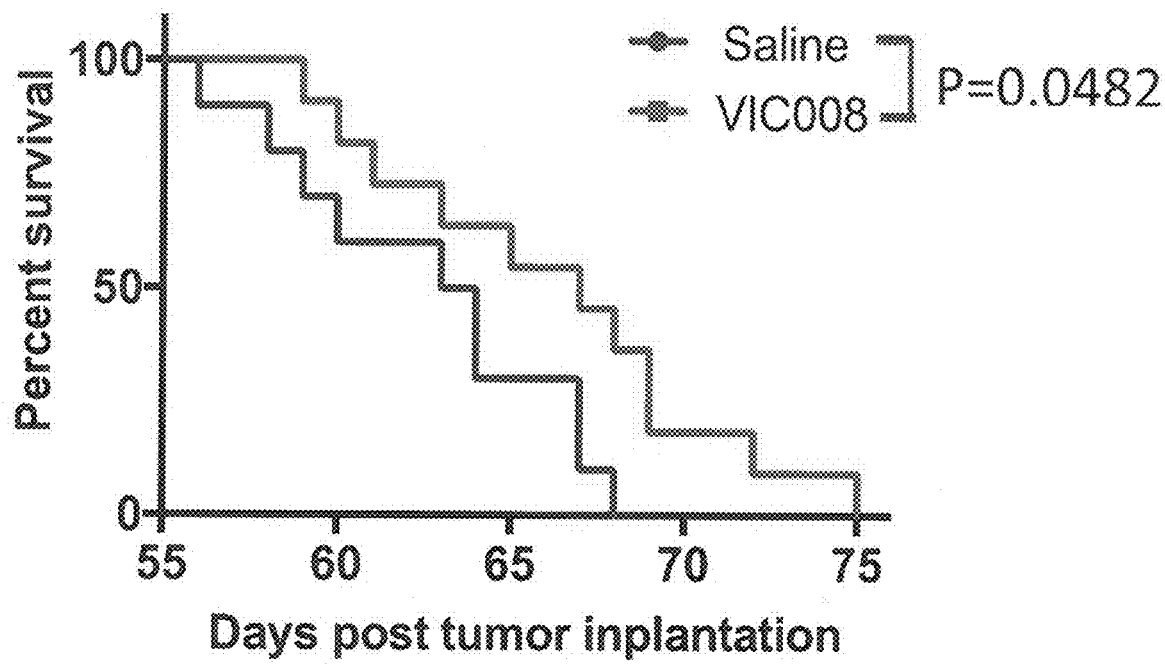

C57BL/6 mice were injected intraperitoneally injected with $5 \times 10^6$ luciferase-expressing ID8 mouse ovarian cancer cells. Mice received four weekly treatments of VIC-008 (20 μg) starting one week after tumor introduction. Results are shown in FIG. 4. The survival curve is shown in FIG. 5.

Figure 6:
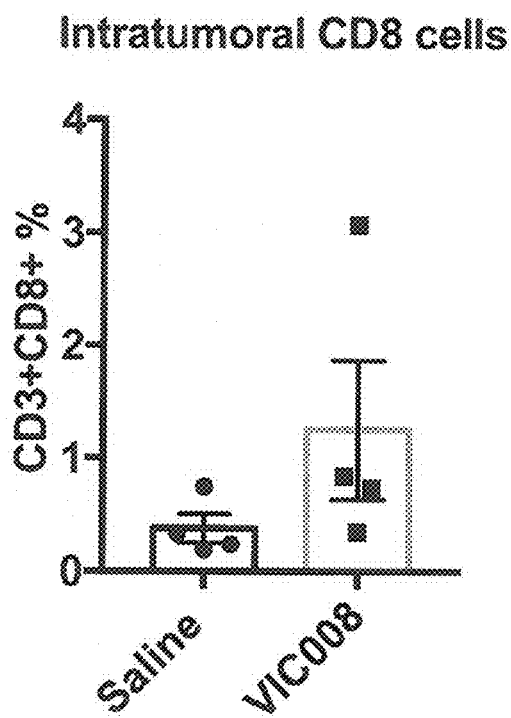

Tumor samples were collected two weeks after the fourth and final treatment of either saline or VIC-008. Tumor tissue was collected and immunoprofiled using flow cytometry to detect CD3+CD8+ T cells. Results are shown in FIG. 6.

Figure 7:
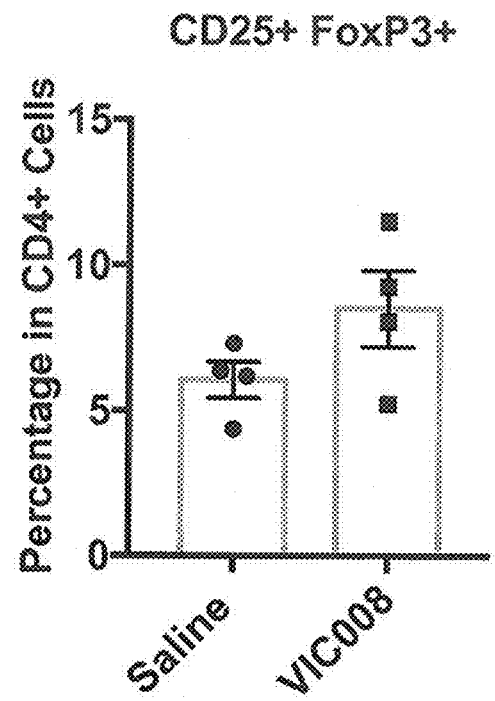

CD4+CD25+FoxP3+ T regulatory cells were detected by flow cytometry. T regulatory cells were counted as a percentage of all CD3+CD4+ cells. Results are shown in FIG. 7.

Figure 8:
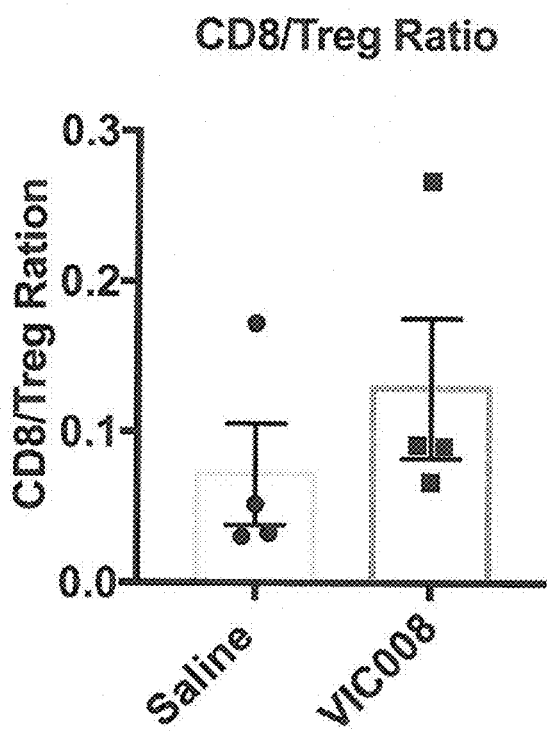

FIG. 8 shows the ratio of CD8+ T cells to T regulatory cells in the tumors. CD3+CD8+ T cells and CD4+CD25+FoxP3+ T regulatory cells were detected by flow cytometry. The ratio was calculated based on percentages of the observed population.

Figure 9:
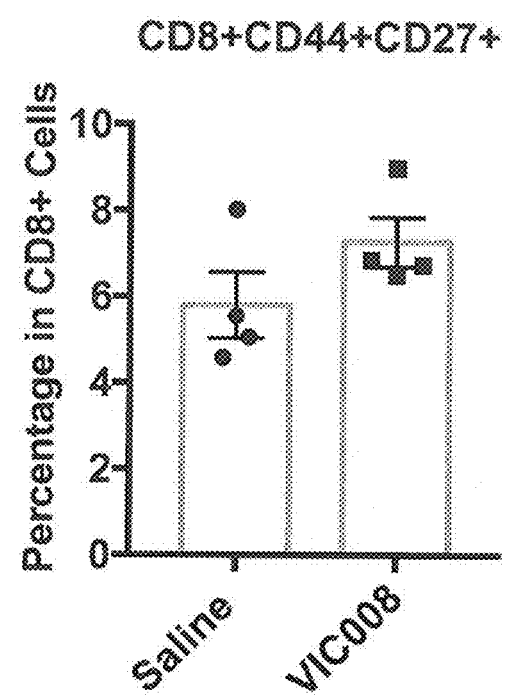

FIG. 9 shows intratumoral central memory CD8+ T cell infiltration. Flow cytometry was used to detect CD8+CD44+CD27+ central memory T cells. CD8+ central memory T cells were counted as a percentage of all CD3+CD8+ cells.

The foregoing is illustrative of the present invention, and is not to be construed as limiting thereof. The invention is defined by the following claims, with equivalents of the claims to be included therein.

That which is claimed is:

1. A fusion protein comprising an antibody or antigen-binding fragment thereof fused in frame to a fragment of *Mycobacterium tuberculosis* heat shock protein 70 (HSP70) of less than 200 amino acids, wherein the fragment of HSP70 comprises a minimal HSP70 sequence, wherein the fragment of HSP70 comprises a modified CD94 domain consisting of the amino acid sequence of

AAHNNLLGSFELTG; (SEQ ID NO: 16)

AAHNNLLGRFELTG; (SEQ ID NO: 17)

AAHNNLLGRFELSG; (SEQ ID NO: 18)

TKENNLLGRFELSG; (SEQ ID NO: 19)
[[or]]
and

TRDNNLLGRFELSG. (SEQ ID NO: 20)

and
wherein the fusion protein comprises the amino acid sequence of SEQ ID SEQ ID NO:9, SEQ ID NO:11, SEQ ID NO:12, SEQ ID NO:13, or SEQ ID NO:31.

2. The fusion protein of claim 1, further comprising a linker between the antibody or antigen-binding fragment thereof and the fragment of HSP70.

3. The fusion protein of claim 2, wherein said linker comprises an amino acid sequence selected from the group consisting of: GGSSRSS (SEQ ID NO: 21), (GGGSGGG)4 (SEQ ID NO: 22), GGGGSGGGGSGGGGS (SEQ ID NO: 23), GGSSRSSSSGGGGSGGGG (SEQ ID NO: 24), and GGSSESSSSGGGGSGGGG (SEQ ID NO: 25.

4. A pharmaceutical composition comprising an effective amount of the fusion protein of claim 1 and a pharmaceutically acceptable carrier.

5. An immunogenic composition comprising the fusion protein of claim 1.

6. A kit comprising the fusion protein of claim 1 and packaging means thereof.

7. A fusion protein comprising an antibody or antigen-binding fragment thereof fused in frame to a fragment of *Mycobacterium tuberculosis* heat shock protein 70 (HSP70) of less than 200 amino acids, wherein the fragment of HSP70 comprises a minimal HSP70 sequence, wherein the fragment of HSP70 comprises a modified CD94 domain consisting of the amino acid sequence of
TKDNNLLGRFELSG (SEQ ID NO:20); and
wherein the fusion protein comprises the amino acid sequence of SEQ ID NO:7.

* * * * *

SEQUENCE LISTING

<160> NUMBER OF SEQ ID NOS: 35

<210> SEQ ID NO 1
<211> LENGTH: 625
<212> TYPE: PRT
<213> ORGANISM: Mycobacterium tuberculosis

<400> SEQUENCE: 1

```
Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80
```

```
Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
            115                 120                 125

Ala Thr Lys Asp Ala Gly Gln Ile Ala Gly Leu Asn Val Leu Arg Ile
        130                 135                 140

Val Asn Glu Pro Thr Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
        290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
        355                 360                 365

Thr Pro Leu Ser Leu Gly Ile Glu Thr Lys Gly Gly Val Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
            420                 425                 430

Leu Thr Gly Ile Pro Pro Ala Pro Arg Gly Ile Pro Gln Ile Glu Val
        435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495
```

Ala Glu Glu Asp Arg Lys Arg Arg Glu Ala Asp Val Arg Asn Gln
            500                 505                 510

Ala Glu Thr Leu Val Tyr Gln Thr Glu Lys Phe Val Lys Glu Gln Arg
        515                 520                 525

Glu Ala Glu Gly Gly Ser Lys Val Pro Glu Asp Thr Leu Asn Lys Val
    530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
            565                 570                 575

Leu Gly Gln Ala Ile Tyr Glu Ala Ala Gln Ala Ser Gln Ala Thr
        580                 585                 590

Gly Ala Ala His Pro Gly Gly Glu Pro Gly Gly Ala His Pro Gly Ser
    595                 600                 605

Ala Asp Asp Val Val Asp Ala Glu Val Val Asp Gly Arg Glu Ala
    610                 615                 620

Lys
625

<210> SEQ ID NO 2
<211> LENGTH: 1200
<212> TYPE: DNA
<213> ORGANISM: Artificial
<220> FEATURE:
<223> OTHER INFORMATION: encodes fusion protein

<400> SEQUENCE: 2
caagttcaac ttcaacaatc tggtcctggt cttgttactc cttctcaaac tctttctctt      60
acttgtgcta tttctggtga ttctgttttct tctaattctg ctacttggaa ttggattaga    120
caatctcctt ctagaggtct tgaatggctt ggtagaactt attatagatc taagtggtat     180
aatgattatg ctgtttctgt taagtctaga atgtctatta tcctgatac ttctaagaat      240 caattttctc ttcaacttaa ttctgttact cctgaagata ctgctgttta ttattgtgct     300
agaggtatga tgacttatta ttatggtatg gatgtttggg gtcaaggtac tactgttact     360
gtttcttctg gtattcttgg ttctggtgga ggtggatctg gtggaggtgg atcaggtgga    420
ggtggttctc aacctgttct tactcaatct tcttctcttt ctgcttctcc tggtgcttct    480
gcttctctta cttgtactct tagatctggt attaatgttg gtccttatag aatttattgg     540
tatcaacaaa agcctggttc tcctcctcaa tatcttctta attataagtc tgattctgat    600
aagcaacaag ttctggtgt tccttctaga ttttctggtt ctaaggatgc ttctgctaat     660
gctggtgttc ttcttatttc tggtcttaga tctgaagatg aagctgatta ttattgtatg    720
atttggcatt cttctgctgc tgttttggt ggtggtactc aacttactgt tcttggtgga    780
ggtggatctg gtggaggtgg atcaggtgga ggtggttctg tgacccctttt gtctttgggt    840 attgaaacta aaggaggttt tatgactaga cttattgaac gtaataccac tattcctacg    900
aagagatcag agacatttac tactgctgat gacaatcaac ctagtgttca gatccaagtg    960
tatcaaggag agagggaaat tgctgcacat aataagttgc ttggctcatt tgaacttact    1020
ggaattccac ctgctcctag aggtattcca caaatagaag tgacatttga cattgacgca    1080
aatgggatag ttcatgtgac tgctaaggat aaaggaactg gtaaagagaa actattcgt    1140 attcaggaag gtagtggact gtctaaggaa gatattgaca gaatgataaa ggacgcagaa    1200

<210> SEQ ID NO 3

<211> LENGTH: 401
<212> TYPE: PRT
<213> ORGANISM: Artificial
<220> FEATURE:
<223> OTHER INFORMATION: fusion protein

<400> SEQUENCE: 3

```
Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
            115                 120                 125

Gly Gly Gly Gly Ser Gly Gly Gly Ser Gly Gly Gly Gly Ser Gln
            130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Gly Gly Gly Gly Ser Gly Gly Gly Gly Ser Gly Gly Gly Gly
            260                 265                 270

Ser Val Thr Pro Leu Ser Leu Gly Ile Glu Thr Lys Gly Gly Phe Met
            275                 280                 285

Thr Arg Leu Ile Glu Arg Asn Thr Thr Ile Pro Thr Lys Arg Ser Glu
    290                 295                 300

Thr Phe Thr Thr Ala Asp Asp Asn Gln Pro Ser Val Gln Ile Gln Val
305                 310                 315                 320

Tyr Gln Gly Glu Arg Glu Ile Ala Ala His Asn Lys Leu Leu Gly Ser
                325                 330                 335

Phe Glu Leu Thr Gly Ile Pro Pro Ala Pro Arg Gly Ile Pro Gln Ile
            340                 345                 350

Glu Val Thr Phe Asp Ile Asp Ala Asn Gly Ile Val His Val Thr Ala
            355                 360                 365

Lys Asp Lys Gly Thr Gly Lys Glu Asn Thr Ile Arg Ile Gln Glu Gly
        370                 375                 380
```

```
Ser Gly Leu Ser Lys Glu Asp Ile Asp Arg Met Ile Lys Asp Ala Glu
385                 390                 395                 400

Ala

<210> SEQ ID NO 4
<211> LENGTH: 1200
<212> TYPE: DNA
<213> ORGANISM: Artificial
<220> FEATURE:
<223> OTHER INFORMATION: encodes fusion protein

<400> SEQUENCE: 4
caagttcaac ttcaacaatc tggtcctggt cttgttactc cttctcaaac tctttctctt      60
acttgtgcta tttctggtga ttctgtttct tctaattctg ctacttggaa ttggattaga     120
caatctcctt ctagaggtct tgaatggctt ggtagaactt attatagatc taagtggtat     180
aatgattatg ctgtttctgt taagtctaga atgtctatta atcctgatac ttctaagaat     240
caattttctc ttcaacttaa ttctgttact cctgaagata ctgctgttta ttattgtgct     300
agaggtatga tgacttatta ttatggtatg gatgtttggg gtcaaggtac tactgttact     360
gtttcttctg gtattcttgg ttctggtgga ggtggatctg gtggaggtgg atcaggtgga     420
ggtggttctc aacctgttct tactcaatct tcttctcttt ctgcttctcc tggtgcttct     480
gcttctctta cttgtactct tagatctggt attaatgttg gtcctatag aatttattgg      540 tatcaacaaa agcctggttc tcctcctcaa tatcttctta attataagtc tgattctgat     600
aagcaacaag ttctggtgt tccttctaga ttttctggtt ctaaggatgc ttctgctaat     660
gctggtgttc ttcttatttc tggtcttaga tctgaagatg aagctgatta ttattgtatg     720
atttggcatt cttctgctgc tgttttggt ggtggtactc aacttactgt tcttggtgga     780
ggtggatctg gtggaggtgg atcaggtgga ggtggttctg tgacccctt gtctttgggt      840 attgaaacta aaggaggttt tatgactaga cttattgaac gtaataccac tattcctacg     900
aagagatcag agacatttac tactgctgat gacaatcaac tagtgttca gatccaagtg      960 tatcaaggag agagggaaat tactaaggag aataatcttc ttggtagatt tgaattgtct    1020
ggtattccac ctgctcctag aggtattcca caaatagaag tgacatttga cattgacgca    1080
aatgggatag ttcatgtgac tgctaaggat aaaggaactg gtaaagagaa tactattcgt    1140
attcaggaag gtagtggact gtctaaggaa gatattgaca gaatgataaa ggacgcagaa    1200

<210> SEQ ID NO 5
<211> LENGTH: 401
<212> TYPE: PRT
<213> ORGANISM: Artificial
<220> FEATURE:
<223> OTHER INFORMATION: fusion protein

<400> SEQUENCE: 5

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
```

```
                65                  70                  75                  80
            Gln Phe Ser Leu Gln Leu Asn Ser Val Thr Pro Glu Asp Thr Ala Val
                            85                  90                  95
            Tyr Tyr Cys Ala Arg Gly Met Met Thr Tyr Tyr Gly Met Asp Val
                        100                 105                 110
            Trp Gly Gln Gly Thr Thr Val Thr Val Ser Ser Gly Ile Leu Gly Ser
                        115                 120                 125
            Gly Gly Gly Gly Ser Gly Gly Gly Ser Gly Gly Gly Gly Ser Gln
                    130                 135                 140
            Pro Val Leu Thr Gln Ser Ser Leu Ser Ala Ser Pro Gly Ala Ser
            145                 150                 155                 160
            Ala Ser Leu Thr Cys Thr Leu Arg Ser Gly Ile Asn Val Gly Pro Tyr
                                165                 170                 175
            Arg Ile Tyr Trp Tyr Gln Gln Lys Pro Gly Ser Pro Gln Tyr Leu
                        180                 185                 190
            Leu Asn Tyr Lys Ser Asp Ser Asp Lys Gln Gln Gly Ser Gly Val Pro
                        195                 200                 205
            Ser Arg Phe Ser Gly Ser Lys Asp Ala Ser Ala Asn Ala Gly Val Leu
            210                 215                 220
            Leu Ile Ser Gly Leu Arg Ser Glu Asp Glu Ala Asp Tyr Tyr Cys Met
            225                 230                 235                 240
            Ile Trp His Ser Ser Ala Ala Val Phe Gly Gly Gly Thr Gln Leu Thr
                                245                 250                 255
            Val Leu Gly Gly Gly Gly Ser Gly Gly Gly Gly Ser Gly Gly Gly Gly
                            260                 265                 270
            Ser Val Thr Pro Leu Ser Leu Gly Ile Glu Thr Lys Gly Gly Phe Met
                    275                 280                 285
            Thr Arg Leu Ile Glu Arg Asn Thr Thr Ile Pro Thr Lys Arg Ser Glu
                        290                 295                 300
            Thr Phe Thr Thr Ala Asp Asp Asn Gln Pro Ser Val Gln Ile Gln Val
            305                 310                 315                 320
            Tyr Gln Gly Glu Arg Glu Ile Thr Lys Glu Asn Asn Leu Leu Gly Arg
                                325                 330                 335
            Phe Glu Leu Ser Gly Ile Pro Pro Ala Pro Arg Gly Ile Pro Gln Ile
                        340                 345                 350
            Glu Val Thr Phe Asp Ile Asp Ala Asn Gly Ile Val His Val Thr Ala
                        355                 360                 365
            Lys Asp Lys Gly Thr Gly Lys Glu Asn Thr Ile Arg Ile Gln Glu Gly
            370                 375                 380
            Ser Gly Leu Ser Lys Glu Asp Ile Asp Arg Met Ile Lys Asp Ala Glu
            385                 390                 395                 400
            Ala

<210> SEQ ID NO 6
<211> LENGTH: 1200
<212> TYPE: DNA
<213> ORGANISM: Artificial
<220> FEATURE:
<223> OTHER INFORMATION: encodes fusion protein

<400> SEQUENCE: 6
caagttcaac ttcaacaatc tggtcctggt cttgttactc cttctcaaac tctttctctt      60
acttgtgcta tttctggtga ttctgtttct tctaattctg ctacttggaa ttggattaga     120
caatctcctt ctagaggtct tgaatggctt ggtagaactt attatagatc taagtggtat     180
```

-continued

```
aatgattatg ctgtttctgt taagtctaga atgtctatta atcctgatac ttctaagaat    240
caattttctc ttcaacttaa ttctgttact cctgaagata ctgctgttta ttattgtgct    300
agaggtatga tgacttatta ttatggtatg gatgtttggg gtcaaggtac tactgttact    360
gtttcttctg gtattcttgg ttctggtgga ggtggatctg gtggaggtgg atcaggtgga    420
ggtggttctc aacctgttct tactcaatct tcttctcttt ctgcttctcc tggtgcttct    480
gcttctctta cttgtactct tagatctggt attaatgttg gtccttatag aatttattgg    540
tatcaacaaa agcctggttc tcctcctcaa tatcttctta attataagtc tgattctgat    600
aagcaacaag gttctggtgt tccttctaga ttttctggtt ctaaggatgc ttctgctaat    660
gctggtgttc ttcttatttc tggtcttaga tctgaagatg aagctgatta ttattgtatg    720
atttggcatt cttctgctgc tgtttttggt ggtggtactc aacttactgt tcttggtgga    780
ggtggatctg gtggaggtgg atcaggtgga ggtggttctg tgaccccttt gtctttgggt    840
attgaaacta aaggaggttt tatgactaga cttattgaac gtaataccac tattcctacg    900
aagagatcag agacatttac tactgctgat gacaatcaac tagtgttca gatccaagtg    960 tatcaaggag agagggaaat tactaaggat aataatcttc ttggtagatt tgaactttct    1020
ggtattccac ctgctcctag aggtattcca caaatagaag tgacatttga cattgacgca    1080
aatgggatag ttcatgtgac tgctaaggat aaaggaactg gtaaagagaa tactattcgt    1140
attcaggaag gtagtggact gtctaaggaa gatattgaca gaatgataaa ggacgcagaa    1200
```

<210> SEQ ID NO 7
<211> LENGTH: 401
<212> TYPE: PRT
<213> ORGANISM: Artificial
<220> FEATURE:
<223> OTHER INFORMATION: fusion protein

<400> SEQUENCE: 7

```
Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Ser Gln
    130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
```

```
                    180                 185                 190
Leu Asn Tyr Lys Ser Asp Ser Asp Lys Gln Gln Gly Ser Gly Val Pro
                195                 200                 205

Ser Arg Phe Ser Gly Ser Lys Asp Ala Ser Ala Asn Ala Gly Val Leu
            210                 215                 220

Leu Ile Ser Gly Leu Arg Ser Glu Asp Glu Ala Asp Tyr Tyr Cys Met
225                 230                 235                 240

Ile Trp His Ser Ala Ala Val Phe Gly Gly Gly Thr Gln Leu Thr
                245                 250                 255

Val Leu Gly Gly Gly Gly Ser Gly Gly Gly Gly Ser Gly Gly Gly Gly
            260                 265                 270

Ser Val Thr Pro Leu Ser Leu Gly Ile Glu Thr Lys Gly Gly Phe Met
                275                 280                 285

Thr Arg Leu Ile Glu Arg Asn Thr Thr Ile Pro Thr Lys Arg Ser Glu
            290                 295                 300

Thr Phe Thr Thr Ala Asp Asp Asn Gln Pro Ser Val Gln Ile Gln Val
305                 310                 315                 320

Tyr Gln Gly Glu Arg Glu Ile Thr Lys Asp Asn Asn Leu Leu Gly Arg
                325                 330                 335

Phe Glu Leu Ser Gly Ile Pro Pro Ala Pro Arg Gly Ile Pro Gln Ile
            340                 345                 350

Glu Val Thr Phe Asp Ile Asp Ala Asn Gly Ile Val His Val Thr Ala
355                 360                 365

Lys Asp Lys Gly Thr Gly Lys Glu Asn Thr Ile Arg Ile Gln Glu Gly
        370                 375                 380

Ser Gly Leu Ser Lys Glu Asp Ile Asp Arg Met Ile Lys Asp Ala Glu
385                 390                 395                 400

Ala
```

<210> SEQ ID NO 8
<211> LENGTH: 1209
<212> TYPE: DNA
<213> ORGANISM: Artificial
<220> FEATURE:
<223> OTHER INFORMATION: encodes fusion protein

<400> SEQUENCE: 8

```
caagttcaac ttcaacaatc tggtcctggt cttgttactc cttctcaaac tctttctctt      60
acttgtgcta tttctggtga ttctgtttct tctaattctg ctacttggaa ttggattaga     120
caatctcctt ctagaggtct tgaatggctt ggtagaactt attatagatc taagtggtat     180
aatgattatg ctgtttctgt taagtctaga atgtctatta atcctgatac ttctaagaat     240
caattttctc ttcaacttaa ttctgttact cctgaagata ctgctgttta ttattgtgct     300
agaggtatga tgacttatta ttatggtatg gatgtttggg gtcaaggtac tactgttact     360
gtttcttctg gtattcttgg ttctggtgga ggtggatctg gtggaggtgg atcaggtgga     420
ggtggttctc aacctgttct tactcaatct tcttctcttt ctgcttctcc tggtgcttct     480
gcttctctta cttgtactct tagatctggt attaatgttg gtccttatag aatttattgg     540
tatcaacaaa agcctggttc tcctcctcaa atcttcttta attataagtc tgattctgat     600
aagcaacaag ttctggtgt tccttctaga ttttctggtt ctaaggatgc ttctgctaat     660
gctggtgttc ttcttattc tggtcttaga tctgaagatg aagctgatta ttattgtatg     720
atttggcatt cttctgctgc tgttttttggt ggtggtactc aacttactgt tcttggtgga     780
```

```
tcttcaagat cttcaagttc tggtggagga ggttctggtg gaggtggtgt gacccctttg    840
tctttgggta ttgaaactaa aggaggtttt atgactagac ttattgaacg taataccact    900
attcctacga agagatcaga gacatttact actgctgatg acaatcaacc tagtgttcag    960
atccaagtgt atcaaggaga gagggaaatt actaaggaga ataatcttct tggtagattt   1020
gaattgtctg gtattccacc tgctcctaga ggtattccac aaatagaagt gacatttgac   1080
attgacgcaa atgggatagt tcatgtgact gctaaggata aaggaactgg taaagagaat   1140
actattcgta ttcaggaagg tagtggactg tctaaggaag atattgacag aatgataaag   1200
gacgcagaa                                                            1209
```

<210> SEQ ID NO 9
<211> LENGTH: 404
<212> TYPE: PRT
<213> ORGANISM: Artificial
<220> FEATURE:
<223> OTHER INFORMATION: fusion protein

<400> SEQUENCE: 9

```
Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Gly Ser Gly Gly Gly Gly Ser Gln
    130                 135                 140

Pro Val Leu Thr Gln Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Gly Gly Ser Ser Arg Ser Ser Ser Gly Gly Gly Ser
            260                 265                 270

Gly Gly Gly Gly Val Thr Pro Leu Ser Leu Gly Ile Glu Thr Lys Gly
        275                 280                 285
```

Gly Phe Met Thr Arg Leu Ile Glu Arg Asn Thr Thr Ile Pro Thr Lys
        290                 295                 300

Arg Ser Glu Thr Phe Thr Thr Ala Asp Asp Asn Gln Pro Ser Val Gln
305                 310                 315                 320

Ile Gln Val Tyr Gln Gly Glu Arg Glu Ile Thr Lys Glu Asn Asn Leu
                325                 330                 335

Leu Gly Arg Phe Glu Leu Ser Gly Ile Pro Pro Ala Pro Arg Gly Ile
            340                 345                 350

Pro Gln Ile Glu Val Thr Phe Asp Ile Asp Ala Asn Gly Ile Val His
        355                 360                 365

Val Thr Ala Lys Asp Lys Gly Thr Gly Lys Glu Asn Thr Ile Arg Ile
    370                 375                 380

Gln Glu Gly Ser Gly Leu Ser Lys Glu Asp Ile Asp Arg Met Ile Lys
385                 390                 395                 400

Asp Ala Glu Ala

<210> SEQ ID NO 10
<211> LENGTH: 1209
<212> TYPE: DNA
<213> ORGANISM: Artificial
<220> FEATURE:
<223> OTHER INFORMATION: encodes fusion protein

<400> SEQUENCE: 10

```
caagttcaac ttcaacaatc tggtcctggt cttgttactc cttctcaaac tctttctctt      60
acttgtgcta tttctggtga ttctgtttct tctaattctg ctacttggaa ttggattaga     120
caatctcctt ctagaggtct tgaatggctt ggtagaactt attatagatc taagtggtat     180
aatgattatg ctgtttctgt taagtctaga atgtctatta atcctgatac ttctaagaat     240
caattttctc ttcaacttaa ttctgttact cctgaagata ctgctgttta ttattgtgct     300
agaggtatga tgacttatta ttatggtatg gatgtttggg gtcaaggtac tactgttact     360
gtttcttctg gtattcttgg ttctggtgga ggtggatctg gtggaggtgg atcaggtgga     420
ggtggttctc aacctgttct tactcaatct tcttctcttt ctgcttctcc tggtgcttct     480
gcttctctta cttgtactct tagatctggt attaatgttg gtccttatag aatttattgg     540
tatcaacaaa agcctggttc tcctcctcaa tatcttctta attataagtc tgattctgat     600
aagcaacaag gttctggtgt tccttctaga ttttctggtt ctaaggatgc ttctgctaat     660
gctggtgttc ttcttatttc tggtcttaga tctgaagatg aagctgatta ttattgtatg     720
atttggcatt cttctgctgc tgttttttggt ggtggtactc aacttactgt tcttggtgga     780
tcttcagaat cttcaagttc tggtggagga ggttctggtg gaggtggtgt gaccccttttg    840
tctttgggta ttgaaactaa aggaggtttt atgactagac ttattgaacg taataccact     900
attcctacga agagatcaga gacatttact actgctgatg acaatcaacc tagtgttcag     960
atccaagtgt atcaaggaga gagggaaatt actaaggaga ataatcttct tggtagattt    1020
gaattgtctg gtattccacc tgctcctaga ggtattccac aaatagaagt gacatttgac    1080
attgacgcaa atgggatagt tcatgtgact gctaaggata aggaactgga taaagagaat    1140
actattcgta ttcaggaagg tagtggactg tctaaggaag atattgacag aatgataaag    1200
gacgcagaa                                                            1209
```

<210> SEQ ID NO 11
<211> LENGTH: 404

```
<212> TYPE: PRT
<213> ORGANISM: Artificial
<220> FEATURE:
<223> OTHER INFORMATION: fusion protein

<400> SEQUENCE: 11

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
    115                 120                 125

Gly Gly Gly Gly Ser Gly Gly Gly Ser Gly Gly Gly Gly Ser Gln
130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
            165                 170                 175

Arg Ile Tyr Trp Tyr Gln Gln Lys Pro Gly Ser Pro Pro Gln Tyr Leu
        180                 185                 190

Leu Asn Tyr Lys Ser Asp Ser Asp Lys Gln Gln Gly Ser Gly Val Pro
    195                 200                 205

Ser Arg Phe Ser Gly Ser Lys Asp Ala Ser Ala Asn Ala Gly Val Leu
210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Gly Gly Ser Ser Glu Ser Ser Ser Gly Gly Gly Gly Ser
            260                 265                 270

Gly Gly Gly Gly Val Thr Pro Leu Ser Leu Gly Ile Glu Thr Lys Gly
        275                 280                 285

Gly Phe Met Thr Arg Leu Ile Glu Arg Asn Thr Thr Ile Pro Thr Lys
    290                 295                 300

Arg Ser Glu Thr Phe Thr Thr Ala Asp Asp Asn Gln Pro Ser Val Gln
305                 310                 315                 320

Ile Gln Val Tyr Gln Gly Glu Arg Glu Ile Thr Lys Glu Asn Asn Leu
                325                 330                 335

Leu Gly Arg Phe Glu Leu Ser Gly Ile Pro Pro Ala Pro Arg Gly Ile
            340                 345                 350

Pro Gln Ile Glu Val Thr Phe Asp Ile Asp Ala Asn Gly Ile Val His
        355                 360                 365

Val Thr Ala Lys Asp Lys Gly Thr Gly Lys Glu Asn Thr Ile Arg Ile
    370                 375                 380
```

-continued

```
Gln Glu Gly Ser Gly Leu Ser Lys Glu Asp Ile Asp Arg Met Ile Lys
385                 390                 395                 400

Asp Ala Glu Ala

<210> SEQ ID NO 12
<211> LENGTH: 771
<212> TYPE: PRT
<213> ORGANISM: Artificial
<220> FEATURE:
<223> OTHER INFORMATION: fusion protein

<400> SEQUENCE: 12

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
            115                 120                 125

Gly Gly Gly Gly Ser Gly Gly Gly Ser Gly Gly Gly Ser Gln
130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Thr Gln Leu Thr
                245                 250                 255

Val Leu Gly Gly Ser Ser Arg Ser Ser Ser Gly Gly Gly Gly Ser
            260                 265                 270

Gly Gly Gly Gly Met Ala Arg Ala Val Gly Ile Asp Leu Gly Thr Thr
            275                 280                 285

Asn Ser Val Val Ser Val Leu Glu Gly Gly Asp Pro Val Val Val Ala
        290                 295                 300

Asn Ser Glu Gly Ser Arg Thr Thr Pro Ser Ile Val Ala Phe Ala Arg
305                 310                 315                 320

Asn Gly Glu Val Leu Val Gly Gln Pro Ala Lys Asn Gln Ala Val Thr
                325                 330                 335

Asn Val Asp Arg Thr Val Arg Ser Val Lys Arg His Met Gly Ser Asp
```

-continued

```
                340                 345                 350
Trp Ser Ile Glu Ile Asp Gly Lys Lys Tyr Thr Ala Pro Glu Ile Ser
        355                 360                 365

Ala Arg Ile Leu Met Lys Leu Lys Arg Asp Ala Glu Ala Tyr Leu Gly
    370                 375                 380

Glu Asp Ile Thr Asp Ala Val Ile Thr Thr Pro Ala Tyr Phe Asn Asp
385                 390                 395                 400

Ala Gln Arg Gln Ala Thr Lys Asp Ala Gly Gln Ile Ala Gly Leu Asn
                405                 410                 415

Val Leu Arg Ile Val Asn Glu Pro Thr Ala Ala Leu Ala Tyr Gly
            420                 425                 430

Leu Asp Lys Gly Glu Lys Glu Gln Arg Ile Leu Val Phe Asp Leu Gly
        435                 440                 445

Gly Gly Thr Phe Asp Val Ser Leu Leu Glu Ile Gly Glu Gly Val Val
    450                 455                 460

Glu Val Arg Ala Thr Ser Gly Asp Asn His Leu Gly Gly Asp Asp Trp
465                 470                 475                 480

Asp Gln Arg Val Val Asp Trp Leu Val Asp Lys Phe Lys Gly Thr Ser
                485                 490                 495

Gly Ile Asp Leu Thr Lys Asp Lys Met Ala Met Gln Arg Leu Arg Glu
            500                 505                 510

Ala Ala Glu Lys Ala Lys Ile Glu Leu Ser Ser Gln Ser Thr Ser
        515                 520                 525

Ile Asn Leu Pro Tyr Ile Thr Val Asp Ala Asp Lys Asn Pro Leu Phe
    530                 535                 540

Leu Asp Glu Gln Leu Thr Arg Ala Glu Phe Gln Arg Ile Thr Gln Asp
545                 550                 555                 560

Leu Leu Asp Arg Thr Arg Lys Pro Phe Gln Ser Val Ile Ala Asp Thr
                565                 570                 575

Gly Ile Ser Val Ser Glu Ile Asp His Val Val Leu Val Gly Gly Ser
            580                 585                 590

Thr Ala Met Pro Ala Val Thr Asp Leu Val Lys Glu Leu Thr Gly Gly
        595                 600                 605

Lys Glu Pro Asn Lys Gly Val Asn Pro Asp Glu Val Val Ala Val Gly
    610                 615                 620

Ala Ala Leu Gln Ala Gly Val Leu Lys Gly Glu Val Lys Asp Val Leu
625                 630                 635                 640

Leu Leu Asp Val Thr Pro Leu Ser Leu Gly Ile Glu Thr Lys Gly Gly
                645                 650                 655

Phe Met Thr Arg Leu Ile Glu Arg Asn Thr Thr Ile Pro Thr Lys Arg
            660                 665                 670

Ser Glu Thr Phe Thr Thr Ala Asp Asp Asn Gln Pro Ser Val Gln Ile
        675                 680                 685

Gln Val Tyr Gln Gly Glu Arg Glu Ile Thr Lys Glu Asn Asn Leu Leu
    690                 695                 700

Gly Arg Phe Glu Leu Ser Gly Ile Pro Pro Ala Pro Arg Gly Ile Pro
705                 710                 715                 720

Gln Ile Glu Val Thr Phe Asp Ile Asp Ala Asn Gly Ile Val His Val
                725                 730                 735

Thr Ala Lys Asp Lys Gly Thr Gly Lys Glu Asn Thr Ile Arg Ile Gln
            740                 745                 750

Glu Gly Ser Gly Leu Ser Lys Glu Asp Ile Asp Arg Met Ile Lys Asp
        755                 760                 765
```

Ala Glu Ala
    770

<210> SEQ ID NO 13
<211> LENGTH: 771
<212> TYPE: PRT
<213> ORGANISM: Artificial
<220> FEATURE:
<223> OTHER INFORMATION: fusion protein

<400> SEQUENCE: 13

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
    115                 120                 125

Gly Gly Gly Gly Ser Gly Gly Gly Ser Gly Gly Gly Ser Gln
130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Thr Gln Leu Thr
                245                 250                 255

Val Leu Gly Gly Ser Ser Glu Ser Ser Ser Gly Gly Gly Ser
            260                 265                 270

Gly Gly Gly Gly Met Ala Arg Ala Val Gly Ile Asp Leu Gly Thr Thr
        275                 280                 285

Asn Ser Val Val Ser Val Leu Glu Gly Gly Asp Pro Val Val Val Ala
    290                 295                 300

Asn Ser Glu Gly Ser Arg Thr Thr Pro Ser Ile Val Ala Phe Ala Arg
305                 310                 315                 320

Asn Gly Glu Val Leu Val Gly Gln Pro Ala Lys Asn Gln Ala Val Thr
                325                 330                 335

Asn Val Asp Arg Thr Val Arg Ser Val Lys Arg His Met Gly Ser Asp
            340                 345                 350

```
Trp Ser Ile Glu Ile Asp Gly Lys Lys Tyr Thr Ala Pro Glu Ile Ser
            355                 360                 365

Ala Arg Ile Leu Met Lys Leu Lys Arg Asp Ala Glu Ala Tyr Leu Gly
        370                 375                 380

Glu Asp Ile Thr Asp Ala Val Ile Thr Thr Pro Ala Tyr Phe Asn Asp
385                 390                 395                 400

Ala Gln Arg Gln Ala Thr Lys Asp Ala Gly Gln Ile Ala Gly Leu Asn
                405                 410                 415

Val Leu Arg Ile Val Asn Glu Pro Thr Ala Ala Leu Ala Tyr Gly
            420                 425                 430

Leu Asp Lys Gly Glu Lys Glu Gln Arg Ile Leu Val Phe Asp Leu Gly
            435                 440                 445

Gly Gly Thr Phe Asp Val Ser Leu Leu Glu Ile Gly Glu Gly Val Val
            450                 455                 460

Glu Val Arg Ala Thr Ser Gly Asp Asn His Leu Gly Gly Asp Asp Trp
465                 470                 475                 480

Asp Gln Arg Val Val Asp Trp Leu Val Asp Lys Phe Lys Gly Thr Ser
                485                 490                 495

Gly Ile Asp Leu Thr Lys Asp Lys Met Ala Met Gln Arg Leu Arg Glu
            500                 505                 510

Ala Ala Glu Lys Ala Lys Ile Glu Leu Ser Ser Ser Gln Ser Thr Ser
            515                 520                 525

Ile Asn Leu Pro Tyr Ile Thr Val Asp Ala Asp Lys Asn Pro Leu Phe
            530                 535                 540

Leu Asp Glu Gln Leu Thr Arg Ala Glu Phe Gln Arg Ile Thr Gln Asp
545                 550                 555                 560

Leu Leu Asp Arg Thr Arg Lys Pro Phe Gln Ser Val Ile Ala Asp Thr
                565                 570                 575

Gly Ile Ser Val Ser Glu Ile Asp His Val Val Leu Val Gly Gly Ser
            580                 585                 590

Thr Ala Met Pro Ala Val Thr Asp Leu Val Lys Glu Leu Thr Gly Gly
            595                 600                 605

Lys Glu Pro Asn Lys Gly Val Asn Pro Asp Glu Val Val Ala Val Gly
            610                 615                 620

Ala Ala Leu Gln Ala Gly Val Leu Lys Gly Glu Val Lys Asp Val Leu
625                 630                 635                 640

Leu Leu Asp Val Thr Pro Leu Ser Leu Gly Ile Glu Thr Lys Gly Gly
                645                 650                 655

Phe Met Thr Arg Leu Ile Glu Arg Asn Thr Thr Ile Pro Thr Lys Arg
            660                 665                 670

Ser Glu Thr Phe Thr Thr Ala Asp Asp Asn Gln Pro Ser Val Gln Ile
            675                 680                 685

Gln Val Tyr Gln Gly Glu Arg Glu Ile Thr Lys Glu Asn Asn Leu Leu
            690                 695                 700

Gly Arg Phe Glu Leu Ser Gly Ile Pro Pro Ala Pro Arg Gly Ile Pro
705                 710                 715                 720

Gln Ile Glu Val Thr Phe Asp Ile Asp Ala Asn Gly Ile Val His Val
                725                 730                 735

Thr Ala Lys Asp Lys Gly Thr Gly Lys Glu Asn Thr Ile Arg Ile Gln
            740                 745                 750

Glu Gly Ser Gly Leu Ser Lys Glu Asp Ile Asp Arg Met Ile Lys Asp
            755                 760                 765
```

Ala Glu Ala
    770

<210> SEQ ID NO 14
<211> LENGTH: 4
<212> TYPE: PRT
<213> ORGANISM: Mycobacterium tuberculosis

<400> SEQUENCE: 14

Lys Asp Glu Leu
1

<210> SEQ ID NO 15
<211> LENGTH: 14
<212> TYPE: PRT
<213> ORGANISM: Mycobacterium tuberculosis

<400> SEQUENCE: 15

Ala Ala His Asn Lys Leu Leu Gly Ser Phe Glu Leu Thr Gly
1               5                   10

<210> SEQ ID NO 16
<211> LENGTH: 14
<212> TYPE: PRT
<213> ORGANISM: Artificial
<220> FEATURE:
<223> OTHER INFORMATION: modified CD94 domain

<400> SEQUENCE: 16

Ala Ala His Asn Asn Leu Leu Gly Ser Phe Glu Leu Thr Gly
1               5                   10

<210> SEQ ID NO 17
<211> LENGTH: 14
<212> TYPE: PRT
<213> ORGANISM: Artificial
<220> FEATURE:
<223> OTHER INFORMATION: modified CD94 domain

<400> SEQUENCE: 17

Ala Ala His Asn Asn Leu Leu Gly Arg Phe Glu Leu Thr Gly
1               5                   10

<210> SEQ ID NO 18
<211> LENGTH: 14
<212> TYPE: PRT
<213> ORGANISM: Artificial
<220> FEATURE:
<223> OTHER INFORMATION: modified CD94 domain

<400> SEQUENCE: 18

Ala Ala His Asn Asn Leu Leu Gly Arg Phe Glu Leu Ser Gly
1               5                   10

<210> SEQ ID NO 19
<211> LENGTH: 14
<212> TYPE: PRT
<213> ORGANISM: Artificial
<220> FEATURE:
<223> OTHER INFORMATION: modified CD94 domain

<400> SEQUENCE: 19

Thr Lys Glu Asn Asn Leu Leu Gly Arg Phe Glu Leu Ser Gly
1               5                   10

<210> SEQ ID NO 20

```
<211> LENGTH: 14
<212> TYPE: PRT
<213> ORGANISM: Artificial
<220> FEATURE:
<223> OTHER INFORMATION: modified CD94 domain

<400> SEQUENCE: 20

Thr Lys Asp Asn Asn Leu Leu Gly Arg Phe Glu Leu Ser Gly
1               5                   10

<210> SEQ ID NO 21
<211> LENGTH: 7
<212> TYPE: PRT
<213> ORGANISM: Artificial
<220> FEATURE:
<223> OTHER INFORMATION: linker

<400> SEQUENCE: 21

Gly Gly Ser Ser Arg Ser Ser
1               5

<210> SEQ ID NO 22
<211> LENGTH: 28
<212> TYPE: PRT
<213> ORGANISM: Artificial
<220> FEATURE:
<223> OTHER INFORMATION: linker

<400> SEQUENCE: 22

Gly Gly Gly Ser Gly Gly Gly Gly Ser Gly Gly Gly Gly
1               5                   10                  15
Gly Ser Gly Gly Gly Gly Gly Ser Gly Gly Gly
            20                  25

<210> SEQ ID NO 23
<211> LENGTH: 15
<212> TYPE: PRT
<213> ORGANISM: Artificial
<220> FEATURE:
<223> OTHER INFORMATION: linker

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 18
<212> TYPE: PRT
<213> ORGANISM: Artificial
<220> FEATURE:
<223> OTHER INFORMATION: linker

<400> SEQUENCE: 24

Gly Gly Ser Ser Arg Ser Ser Ser Gly Gly Gly Ser Gly Gly
1               5                   10                  15
Gly Gly

<210> SEQ ID NO 25
<211> LENGTH: 18
<212> TYPE: PRT
<213> ORGANISM: Artificial
<220> FEATURE:
<223> OTHER INFORMATION: linker

<400> SEQUENCE: 25

Gly Gly Ser Ser Glu Ser Ser Ser Ser Gly Gly Gly Gly Ser Gly Gly
```

1               5                    10                   15

Gly Gly

<210> SEQ ID NO 26
<211> LENGTH: 625
<212> TYPE: PRT
<213> ORGANISM: Artificial
<220> FEATURE:
<223> OTHER INFORMATION: fusion protein

<400> SEQUENCE: 26

Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
                20                  25                  30

Ser Arg Thr Thr Pro Ser Ile Val Ala Phe Ala Arg Asn Gly Glu Val
                35                  40                  45

Leu Val Gly Gln Pro Ala Lys Asn Gln Ala Val Thr Asn Val Asp Arg
        50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
                100                 105                 110

Asp Ala Val Ile Thr Thr Pro Ala Tyr Phe Asn Asp Ala Gln Arg Gln
                115                 120                 125

Ala Thr Lys Asp Ala Gly Gln Ile Ala Gly Leu Asn Val Leu Arg Ile
        130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
                180                 185                 190

Thr Ser Gly Asp Asn His Leu Gly Gly Asp Trp Asp Gln Arg Val
        195                 200                 205

Val Asp Trp Leu Val Asp Lys Phe Lys Gly Thr Ser Gly Ile Asp Leu
        210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
                260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
        290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
                340                 345                 350

```
Ala Gly Val Leu Lys Gly Glu Val Lys Asp Val Leu Leu Asp Val
        355                 360                 365

Thr Pro Leu Ser Leu Gly Ile Glu Thr Lys Gly Gly Phe Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
            420                 425                 430

Leu Thr Gly Ile Pro Pro Ala Pro Arg Gly Ile Pro Gln Ile Glu Val
        435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Arg Glu Glu Ala Asp Val Arg Asn Gln
            500                 505                 510

Ala Glu Thr Leu Val Tyr Gln Thr Glu Lys Phe Val Lys Glu Gln Arg
        515                 520                 525

Glu Ala Glu Gly Gly Ser Lys Val Pro Glu Asp Thr Leu Asn Lys Val
530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
            580                 585                 590

Gly Ala Ala His Pro Gly Gly Glu Pro Gly Gly Ala His Pro Gly Ser
        595                 600                 605

Ala Asp Asp Val Val Asp Ala Glu Val Val Asp Gly Arg Glu Ala
    610                 615                 620

Lys
625

<210> SEQ ID NO 27
<211> LENGTH: 898
<212> TYPE: PRT
<213> ORGANISM: Artificial
<220> FEATURE:
<223> OTHER INFORMATION: fusion protein

<400> SEQUENCE: 27

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80
```

```
Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Gly Ser Gln
130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Gly Gly Gly Gly Ser Gly Gly Gly Gly Ser Gly Gly Gly Gly
            260                 265                 270

Ser Met Ala Arg Ala Val Gly Ile Asp Leu Gly Thr Thr Asn Ser Val
        275                 280                 285

Val Ser Val Leu Glu Gly Gly Asp Pro Val Val Val Ala Asn Ser Glu
    290                 295                 300

Gly Ser Arg Thr Thr Pro Ser Ile Val Ala Phe Ala Arg Asn Gly Glu
305                 310                 315                 320

Val Leu Val Gly Gln Pro Ala Lys Asn Gln Ala Val Thr Asn Val Asp
                325                 330                 335

Arg Thr Val Arg Ser Val Lys Arg His Met Gly Ser Asp Trp Ser Ile
            340                 345                 350

Glu Ile Asp Gly Lys Lys Tyr Thr Ala Pro Glu Ile Ser Ala Arg Ile
        355                 360                 365

Leu Met Lys Leu Lys Arg Asp Ala Glu Ala Tyr Leu Gly Glu Asp Ile
    370                 375                 380

Thr Asp Ala Val Ile Thr Thr Pro Ala Tyr Phe Asn Asp Ala Gln Arg
385                 390                 395                 400

Gln Ala Thr Lys Asp Ala Gly Gln Ile Ala Gly Leu Asn Val Leu Arg
                405                 410                 415

Ile Val Asn Glu Pro Thr Ala Ala Ala Leu Ala Tyr Gly Leu Asp Lys
            420                 425                 430

Gly Glu Lys Glu Gln Arg Ile Leu Val Phe Asp Leu Gly Gly Gly Thr
        435                 440                 445

Phe Asp Val Ser Leu Leu Glu Ile Gly Glu Gly Val Val Glu Val Arg
    450                 455                 460

Ala Thr Ser Gly Asp Asn His Leu Gly Gly Asp Asp Trp Asp Gln Arg
465                 470                 475                 480

Val Val Asp Trp Leu Val Asp Lys Phe Lys Gly Thr Ser Gly Ile Asp
                485                 490                 495
```

```
Leu Thr Lys Asp Lys Met Ala Met Gln Arg Leu Arg Glu Ala Ala Glu
            500                 505                 510

Lys Ala Lys Ile Glu Leu Ser Ser Ser Gln Ser Thr Ser Ile Asn Leu
            515                 520                 525

Pro Tyr Ile Thr Val Asp Ala Asp Lys Asn Pro Leu Phe Leu Asp Glu
            530                 535                 540

Gln Leu Thr Arg Ala Glu Phe Gln Arg Ile Thr Gln Asp Leu Leu Asp
545                 550                 555                 560

Arg Thr Arg Lys Pro Phe Gln Ser Val Ile Ala Asp Thr Gly Ile Ser
                565                 570                 575

Val Ser Glu Ile Asp His Val Val Leu Val Gly Gly Ser Thr Arg Met
            580                 585                 590

Pro Ala Val Thr Asp Leu Val Lys Glu Leu Thr Gly Gly Lys Glu Pro
            595                 600                 605

Asn Lys Gly Val Asn Pro Asp Glu Val Val Ala Val Gly Ala Ala Leu
            610                 615                 620

Gln Ala Gly Val Leu Lys Gly Glu Val Lys Asp Val Leu Leu Leu Asp
625                 630                 635                 640

Val Thr Pro Leu Ser Leu Gly Ile Glu Thr Lys Gly Gly Phe Met Thr
                645                 650                 655

Arg Leu Ile Glu Arg Asn Thr Thr Ile Pro Thr Lys Arg Ser Glu Thr
            660                 665                 670

Phe Thr Thr Ala Asp Asp Asn Gln Pro Ser Val Gln Ile Gln Val Tyr
            675                 680                 685

Gln Gly Glu Arg Glu Ile Ala Ala His Asn Lys Leu Leu Gly Ser Phe
690                 695                 700

Glu Leu Thr Gly Ile Pro Pro Ala Pro Arg Gly Ile Pro Gln Ile Glu
705                 710                 715                 720

Val Thr Phe Asp Ile Asp Ala Asn Gly Ile Val His Val Thr Ala Lys
                725                 730                 735

Asp Lys Gly Thr Gly Lys Glu Asn Thr Ile Arg Ile Gln Glu Gly Ser
            740                 745                 750

Gly Leu Ser Lys Glu Asp Ile Asp Arg Met Ile Lys Asp Ala Glu Ala
            755                 760                 765

His Ala Glu Glu Asp Arg Lys Arg Arg Glu Glu Ala Asp Val Arg Asn
            770                 775                 780

Gln Ala Glu Thr Leu Val Tyr Gln Thr Glu Lys Phe Val Lys Glu Gln
785                 790                 795                 800

Arg Glu Ala Glu Gly Gly Ser Lys Val Pro Glu Asp Thr Leu Asn Lys
                805                 810                 815

Val Asp Ala Ala Val Ala Glu Ala Lys Ala Ala Leu Gly Gly Ser Asp
            820                 825                 830

Ile Ser Ala Ile Lys Ser Ala Met Glu Lys Leu Gly Gln Glu Ser Gln
            835                 840                 845

Ala Leu Gly Gln Ala Ile Tyr Glu Ala Ala Gln Ala Ala Ser Gln Ala
            850                 855                 860

Thr Gly Ala Ala His Pro Gly Gly Glu Pro Gly Gly Ala His Pro Gly
865                 870                 875                 880

Ser Ala Asp Asp Val Val Asp Ala Glu Val Val Asp Asp Gly Arg Glu
                885                 890                 895

Ala Lys

<210> SEQ ID NO 28
```

<211> LENGTH: 930
<212> TYPE: PRT
<213> ORGANISM: Artificial
<220> FEATURE:
<223> OTHER INFORMATION: fusion protein

<400> SEQUENCE: 28

```
Gly Ser Ser Gln Val Gln Leu Gln Gln Ser Gly Pro Gly Leu Val Thr
1               5                   10                  15

Pro Ser Gln Thr Leu Ser Leu Thr Cys Ala Ile Ser Gly Asp Ser Val
            20                  25                  30

Ser Ser Asn Ser Ala Thr Trp Asn Trp Ile Arg Gln Ser Pro Ser Arg
        35                  40                  45

Gly Leu Glu Trp Leu Gly Arg Thr Tyr Tyr Arg Ser Lys Trp Tyr Asn
    50                  55                  60

Asp Tyr Ala Val Ser Val Lys Ser Arg Met Ser Ile Asn Pro Asp Thr
65                  70                  75                  80

Ser Lys Asn Gln Phe Ser Leu Gln Leu Asn Ser Val Thr Pro Glu Asp
                85                  90                  95

Thr Ala Val Tyr Tyr Cys Ala Arg Gly Met Met Thr Tyr Tyr Tyr Gly
            100                 105                 110

Met Asp Val Trp Gly Gln Gly Thr Thr Val Thr Val Ser Ser Gly Ile
        115                 120                 125

Leu Gly Ser Gly Gly Gly Ser Gly Gly Gly Ser Gly Gly Gly
    130                 135                 140

Gly Ser Gln Pro Val Leu Thr Gln Ser Ser Ser Leu Ser Ala Ser Pro
145                 150                 155                 160

Gly Ala Ser Ala Ser Leu Thr Cys Thr Leu Arg Ser Gly Ile Asn Val
                165                 170                 175

Gly Pro Tyr Arg Ile Tyr Trp Tyr Gln Gln Lys Pro Gly Ser Pro Pro
            180                 185                 190

Gln Tyr Leu Leu Asn Tyr Lys Ser Asp Ser Asp Lys Gln Gln Gly Ser
        195                 200                 205

Gly Val Pro Ser Arg Phe Ser Gly Ser Lys Asp Ala Ser Ala Asn Ala
    210                 215                 220

Gly Val Leu Leu Ile Ser Gly Leu Arg Ser Glu Asp Glu Ala Asp Tyr
225                 230                 235                 240

Tyr Cys Met Ile Trp His Ser Ser Ala Ala Val Phe Gly Gly Gly Thr
                245                 250                 255

Gln Leu Thr Val Leu Ser Gly Ile Leu Glu Gln Gln Gly Gly Gly Gly
            260                 265                 270

Gly Ser Gly Gly Gly Ser Gly Gly Gly Ser Ala Ala Ala Met
    275                 280                 285

Arg Ser Met Ala Arg Ala Val Gly Ile Asp Leu Gly Thr Thr Asn Ser
    290                 295                 300

Val Val Ser Val Leu Glu Gly Gly Asp Pro Val Val Ala Asn Ser
305                 310                 315                 320

Glu Gly Ser Arg Thr Thr Pro Ser Ile Val Ala Phe Ala Arg Asn Gly
                325                 330                 335

Glu Val Leu Val Gly Gln Pro Ala Lys Asn Gln Ala Val Thr Asn Val
            340                 345                 350

Asp Arg Thr Val Arg Ser Val Lys Arg His Met Gly Ser Asp Trp Ser
        355                 360                 365

Ile Glu Ile Asp Gly Lys Lys Tyr Thr Ala Pro Glu Ile Ser Ala Arg
    370                 375                 380
```

```
Ile Leu Met Lys Leu Lys Arg Asp Ala Glu Ala Tyr Leu Gly Glu Asp
385                 390                 395                 400

Ile Thr Asp Ala Val Ile Thr Thr Pro Ala Tyr Phe Asn Asp Ala Gln
            405                 410                 415

Arg Gln Ala Thr Lys Asp Ala Gly Gln Ile Ala Gly Leu Asn Val Leu
        420                 425                 430

Arg Ile Val Asn Glu Pro Thr Ala Ala Leu Ala Tyr Gly Leu Asp
        435                 440                 445

Lys Gly Glu Lys Glu Gln Arg Ile Leu Val Phe Asp Leu Gly Gly Gly
    450                 455                 460

Thr Phe Asp Val Ser Leu Leu Glu Ile Gly Gly Val Val Glu Val
465                 470                 475                 480

Arg Ala Thr Ser Gly Asp Asn His Leu Gly Gly Asp Asp Trp Asp Gln
                485                 490                 495

Arg Val Val Asp Trp Leu Val Asp Lys Phe Lys Gly Thr Ser Gly Ile
                500                 505                 510

Asp Leu Thr Lys Asp Lys Met Ala Met Gln Arg Leu Arg Glu Ala Ala
            515                 520                 525

Glu Lys Ala Lys Ile Glu Leu Ser Ser Ser Gln Ser Thr Ser Ile Asn
530                 535                 540

Leu Pro Tyr Ile Thr Val Asp Ala Asp Lys Asn Pro Leu Phe Leu Asp
545                 550                 555                 560

Glu Gln Leu Thr Arg Ala Glu Phe Gln Arg Ile Thr Gln Asp Leu Leu
                565                 570                 575

Asp Arg Thr Arg Lys Pro Phe Gln Ser Val Ile Ala Asp Thr Gly Ile
                580                 585                 590

Ser Val Ser Glu Ile Asp His Val Val Leu Val Gly Gly Ser Thr Arg
            595                 600                 605

Met Pro Ala Val Thr Asp Leu Val Lys Glu Leu Thr Gly Gly Lys Glu
    610                 615                 620

Pro Asn Lys Gly Val Asn Pro Asp Glu Val Val Ala Val Gly Ala Ala
625                 630                 635                 640

Leu Gln Ala Gly Val Leu Lys Gly Glu Val Lys Asp Val Leu Leu Leu
                645                 650                 655

Asp Val Thr Pro Leu Ser Leu Gly Ile Glu Thr Lys Gly Gly Val Met
                660                 665                 670

Thr Arg Leu Ile Glu Arg Asn Thr Thr Ile Pro Thr Lys Arg Ser Glu
            675                 680                 685

Thr Phe Thr Thr Ala Asp Asp Asn Gln Pro Ser Val Gln Ile Gln Val
    690                 695                 700

Tyr Gln Gly Glu Arg Glu Ile Ala Ala His Asn Lys Leu Leu Gly Ser
705                 710                 715                 720

Phe Glu Leu Thr Gly Ile Pro Pro Ala Pro Arg Gly Ile Pro Gln Ile
                725                 730                 735

Glu Val Thr Phe Asp Ile Asp Ala Asn Gly Ile Val His Val Thr Ala
                740                 745                 750

Lys Asp Lys Gly Thr Gly Lys Glu Asn Thr Ile Arg Ile Gln Glu Gly
            755                 760                 765

Ser Gly Leu Ser Lys Glu Asp Ile Asp Arg Met Ile Lys Asp Ala Glu
    770                 775                 780

Ala His Ala Glu Glu Asp Arg Lys Arg Arg Glu Glu Ala Asp Val Arg
785                 790                 795                 800
```

```
Asn Gln Ala Glu Thr Leu Val Tyr Gln Thr Glu Lys Phe Val Lys Glu
                805                 810                 815

Gln Arg Glu Ala Glu Gly Gly Ser Lys Val Pro Glu Asp Thr Leu Asn
            820                 825                 830

Lys Val Asp Ala Ala Val Ala Glu Ala Lys Ala Ala Leu Gly Gly Ser
        835                 840                 845

Asp Ile Ser Ala Ile Lys Ser Ala Met Glu Lys Leu Gly Gln Glu Ser
    850                 855                 860

Gln Ala Leu Gly Gln Ala Ile Tyr Glu Ala Ala Gln Ala Ala Ser Gln
865                 870                 875                 880

Ala Thr Gly Ala Ala His Pro Gly Gly Glu Pro Gly Gly Ala His Pro
                885                 890                 895

Gly Ser Ala Asp Asp Val Val Asp Ala Glu Val Val Asp Asp Gly Arg
            900                 905                 910

Glu Ala Lys Asp Val Val Asp Ala Glu Val Val Asp Asp Gly Arg Glu
        915                 920                 925

Ala Lys
    930

<210> SEQ ID NO 29
<211> LENGTH: 641
<212> TYPE: PRT
<213> ORGANISM: Artificial
<220> FEATURE:
<223> OTHER INFORMATION: fusion protein

<400> SEQUENCE: 29

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Asp Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220
```

```
Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
            245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp
```

<210> SEQ ID NO 30
<211> LENGTH: 258
<212> TYPE: PRT
<213> ORGANISM: Artificial
<220> FEATURE:
<223> OTHER INFORMATION: fusion protein

<400> SEQUENCE: 30

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
    115                 120                 125

Gly Gly Gly Gly Ser Gly Gly Gly Ser Gly Gly Gly Gly Ser Gln
130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
            165                 170                 175

Arg Ile Tyr Trp Tyr Gln Gln Lys Pro Gly Ser Pro Pro Gln Tyr Leu
        180                 185                 190

Leu Asn Tyr Lys Ser Asp Ser Asp Lys Gln Gln Gly Ser Gly Val Pro
    195                 200                 205

Ser Arg Phe Ser Gly Ser Lys Asp Ala Ser Ala Asn Ala Gly Val Leu
210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu

<210> SEQ ID NO 31
<211> LENGTH: 771
<212> TYPE: PRT
<213> ORGANISM: Artificial
<220> FEATURE:
<223> OTHER INFORMATION: fusion protein

<400> SEQUENCE: 31

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

-continued

Trp Leu Gly Arg Thr Tyr Tyr Arg Ser Lys Trp Tyr Asn Asp Tyr Ala
 50                  55                  60

Val Ser Val Lys Ser Arg Met Ser Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Met Met Thr Tyr Tyr Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Gly Ser Gln
130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gly Ser Gly Val Pro
        195                 200                 205

Ser Arg Phe Ser Gly Ser Lys Asp Ala Ser Ala Asn Ala Gly Val Leu
210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Gly Gly Ser Ser Glu Ser Ser Ser Gly Gly Gly Gly Ser
            260                 265                 270

Gly Gly Gly Gly Met Ala Arg Ala Val Gly Ile Asp Leu Gly Thr Thr
        275                 280                 285

Asn Ser Val Val Ser Val Leu Glu Gly Gly Asp Pro Val Val Val Ala
290                 295                 300

Asn Ser Glu Gly Ser Arg Thr Thr Pro Ser Ile Val Ala Phe Ala Arg
305                 310                 315                 320

Asn Gly Glu Val Leu Val Gly Gln Pro Ala Lys Asn Gln Ala Val Thr
                325                 330                 335

Asn Val Asp Arg Thr Val Arg Ser Val Lys Arg His Met Gly Ser Asp
            340                 345                 350

Trp Ser Ile Glu Ile Asp Gly Lys Lys Tyr Thr Ala Pro Glu Ile Ser
        355                 360                 365

Ala Arg Ile Leu Met Lys Leu Lys Arg Asp Ala Glu Ala Tyr Leu Gly
370                 375                 380

Glu Asp Ile Thr Asp Ala Val Ile Thr Thr Pro Ala Tyr Phe Asn Asp
385                 390                 395                 400

Ala Gln Arg Gln Ala Thr Lys Asp Ala Gly Gln Ile Ala Gly Leu Asn
                405                 410                 415

Val Leu Arg Ile Val Asn Glu Pro Thr Ala Ala Ala Leu Ala Tyr Gly
            420                 425                 430

Leu Asp Lys Gly Glu Lys Glu Gln Arg Ile Leu Val Phe Asp Leu Gly
        435                 440                 445

Gly Gly Thr Phe Asp Val Ser Leu Leu Glu Ile Gly Glu Gly Val Val
450                 455                 460

```
Glu Val Arg Ala Thr Ser Gly Asp Asn His Leu Gly Gly Asp Asp Trp
465                 470                 475                 480

Asp Gln Arg Val Val Asp Trp Leu Val Asp Lys Phe Lys Gly Thr Ser
            485                 490                 495

Gly Ile Asp Leu Thr Lys Asp Lys Met Ala Met Gln Arg Leu Arg Glu
        500                 505                 510

Ala Ala Glu Lys Ala Lys Ile Glu Leu Ser Ser Ser Gln Ser Thr Ser
    515                 520                 525

Ile Asn Leu Pro Tyr Ile Thr Val Asp Ala Asp Lys Asn Pro Leu Phe
530                 535                 540

Leu Asp Glu Gln Leu Thr Arg Ala Glu Phe Gln Arg Ile Thr Gln Asp
545                 550                 555                 560

Leu Leu Asp Arg Thr Arg Lys Pro Phe Gln Ser Val Ile Ala Asp Thr
            565                 570                 575

Gly Ile Ser Val Ser Glu Ile Asp His Val Val Leu Val Gly Gly Ser
        580                 585                 590

Thr Ala Met Pro Ala Val Thr Asp Leu Val Lys Glu Leu Thr Gly Gly
    595                 600                 605

Lys Glu Pro Asn Lys Gly Val Asn Pro Asp Glu Val Val Ala Val Gly
610                 615                 620

Ala Ala Leu Gln Ala Gly Val Leu Lys Gly Glu Val Lys Asp Val Leu
625                 630                 635                 640

Leu Leu Asp Val Thr Pro Leu Ser Leu Gly Ile Glu Thr Lys Gly Gly
            645                 650                 655

Phe Met Thr Arg Leu Ile Glu Arg Asn Thr Thr Ile Pro Thr Lys Arg
        660                 665                 670

Ser Glu Thr Phe Thr Thr Ala Asp Asp Asn Gln Pro Ser Val Gln Ile
    675                 680                 685

Gln Val Tyr Gln Gly Glu Arg Glu Ile Thr Lys Glu Asn Asn Leu Leu
690                 695                 700

Gly Arg Phe Glu Leu Ser Gly Ile Pro Pro Ala Pro Arg Gly Ile Pro
705                 710                 715                 720

Gln Ile Glu Val Thr Phe Asp Ile Asp Ala Asn Gly Ile Val His Val
            725                 730                 735

Thr Ala Lys Asp Lys Gly Thr Gly Lys Glu Asn Thr Ile Arg Ile Gln
        740                 745                 750

Glu Gly Ser Gly Leu Ser Lys Glu Asp Ile Asp Arg Met Ile Lys Asp
    755                 760                 765

Ala Glu Ala
    770

<210> SEQ ID NO 32
<211> LENGTH: 15
<212> TYPE: PRT
<213> ORGANISM: Artificial
<220> FEATURE:
<223> OTHER INFORMATION: modified Treg domain

<400> SEQUENCE: 32

Val Leu Arg Ile Val Asn Glu Pro Met Ala Ala Ala Leu Ala Tyr
1               5                   10                  15

<210> SEQ ID NO 33
<211> LENGTH: 15
<212> TYPE: PRT
<213> ORGANISM: Artificial
<220> FEATURE:
```

```
<223> OTHER INFORMATION: modified Treg domain

<400> SEQUENCE: 33

Val Leu Arg Ile Val Asn Glu Pro Thr Ala Ala Ala Leu Ala Phe
1               5                   10                  15

<210> SEQ ID NO 34
<211> LENGTH: 15
<212> TYPE: PRT
<213> ORGANISM: Artificial
<220> FEATURE:
<223> OTHER INFORMATION: modified Treg domain

<400> SEQUENCE: 34

Val Leu Arg Ile Val Asn Glu Pro Met Ala Ala Ala Leu Ala Phe
1               5                   10                  15

<210> SEQ ID NO 35
<211> LENGTH: 14
<212> TYPE: PRT
<213> ORGANISM: Artificial
<220> FEATURE:
<223> OTHER INFORMATION: modified CD94 domain

<400> SEQUENCE: 35

Thr Lys Asp Asn Asn Leu Leu Gly Arg Phe Glu Leu Ser Gly
1               5                   10
```